United States Patent
Watkins et al.

(12) 
(10) Patent No.: US 6,689,782 B2
(45) Date of Patent: Feb. 10, 2004

(54) FUNGAL EFFLUX PUMP INHIBITORS

(75) Inventors: William J. Watkins, Sunnyvale, CA (US); Remy Lemoine, San Francisco, CA (US); Aesop Cho, Mountain View, CA (US); Monica Palme, San Jose, CA (US)

(73) Assignee: Essential Therapeutics, Inc., Waltham, MA (US)

( * ) Notice: Subject to any disclaimer, the term of this patent is extended or adjusted under 35 U.S.C. 154(b) by 0 days.

(21) Appl. No.: 10/334,755

(22) Filed: Dec. 30, 2002

(65) Prior Publication Data

US 2003/0229097 A1 Dec. 11, 2003

Related U.S. Application Data

(63) Continuation-in-part of application No. 10/243,074, filed on Sep. 12, 2002, which is a continuation-in-part of application No. 09/906,864, filed on Jul. 16, 2001, now Pat. No. 6,596,723.

(51) Int. Cl.[7] .................. A61K 31/495; A61K 31/33; A61K 31/517; C07D 239/72; C07D 403/00

(52) U.S. Cl. ............... 514/252.17; 514/183; 514/266.1; 514/266.2; 514/266.3; 544/287; 544/322; 544/253; 544/283; 544/358; 544/359

(58) Field of Search .................... 514/183, 252.17, 514/266.1, 266.2, 266.3; 544/287, 322, 253, 358, 359

(56) References Cited

FOREIGN PATENT DOCUMENTS

| DE | 3721855 A1 | 9/1988 |
|----|------------|--------|
| JP | 62198670 | * 7/1987 |
| WO | WO 2001081346 A2 | 11/2001 |

OTHER PUBLICATIONS

Debnath et al(J. Med. Chem. 42/17, 3203–9(1999), also cited as Chemical Abstract 131:266552.*

Kokosi, J., et al., "Nitrogen bridged compounds, Part 90," *Heterocycles,* (1998); 48/9, 1851–66, database Caplus on STN, AN 1998: 663413; also cited as Chemical Abstract DN 130: 38348. See compounds with CAS RN #172420–42–7, and compounds of Formula II.

* cited by examiner

*Primary Examiner*—Mukund J. Shah
*Assistant Examiner*—Sudhaker B. Patel
(74) *Attorney, Agent, or Firm*—Bernard F. Rose; Bingham McCutchen LLP

(57) ABSTRACT

This invention relates to compounds that are efflux pump inhibitors and therefore are useful as potentiators of antifungal agents for the treatment of infections caused by fungi that employ an efflux pump resistance mechanism.

37 Claims, No Drawings

FUNGAL EFFLUX PUMP INHIBITORS

RELATED APPLICATIONS

This application is a continuation-in-part of application Ser. No. 09/906,864, filed Jul. 16, 2001 U.S. Pat. No. 6,596,723, and application Ser. No. 10/243,074, filed Sep. 12, 2002, each of which is incorporated by reference as if fully set forth herein.

FIELD OF THE INVENTION

The present invention relates to the fields of organic chemistry, biochemistry, medicinal chemistry, microbiology and medicine. In particular, it relates to organic compounds that are fungal efflux pump inhibitors.

BACKGROUND OF THE INVENTION

The information provided and the references cited herein are not admitted, nor should they be construed, to be prior art to the present invention; rather, they are provided solely to assist the reader in understanding the present invention.

Fungal infections are relatively rare in immuno-competent patients. In fact, a number of Candida species are often present as benign commensal organisms in the digestive system of healthy individuals (Shepherd, et al., *Ann. Rev. Microbiol.*, 1985, 39:579–614). Fungal infections, however, can be life threatening for immuno-compromised patients. There are three major groups of immuno-compromised individuals that are at risk: (1) cancer patients undergoing chemotherapy, (2) organ transplant patients being treated with immuno-suppressants, and (3) AIDS patients. Data from the National Nosocomial Infections Surveillance System conducted in the United States showed a 487 percent increase in Candida bloodstream infections between 1980 and 1989 (Rinaldi, et al., *Antimicrob. Ag. Chemother.*, 1995, 39:1–8). Oropharyngeal candidiasis is the most common fungal infection complication associated with AIDS with up to 90% of AIDS patients having had at least one episode of the infection (Powderly, *AIDS research and Human Retroviruses*, 1994, 10:925–929).

There are relatively few clinically useful anti-fungal agents. Among those available are amphotericin B, flucytosine, fluconazole, itraconazole and ketoconazole (Odds, *J. Antimicrob. Chemother.*, 1993, 31: 463–471). However, resistance to all of these drugs is developing rapidly. Take, for example, fluconazole.

Fluconazole is currently the most extensively used anti-fungal agent for the treatment of patients with severe candidiasis. It has higher water solubility and a longer plasma half-life than other azole fungicides and has relatively low toxicity. Between 1988 and 1993, fluconazole was used to treat over 15 million patients, including at least 250,000 AIDS patients (Hitchcock, *Biochem. Soc. Trans.*, 1993, 21:1039–1047). Given such wide-spread use, it comes as no surprise that fluconazole-resistant Candida strains have been reported (Rex, et al., *Antimicrob. Ag. Chemother.*, 1995, 39:1–8; Vanden Bossche, et al., 1994, supra). In some cases the resistance was found to be due to mutations in *C. albicans* itself while in other cases *C. albicans* was simply displaced by Candida species less susceptible to fluconazole, namely, *C. glabrata* and *C. krusei* (Odds, 1993, supra).

The mechanism of resistance to fluconazole appears to be multifaceted. In one study, amplification of the CYP51 gene (encoding the fluconazole target P-450 protein C14 demethylase) was implicated (Vanden Bossche, et al., *Antimicrob. Agents and Chemother.*, 1994, 36: 2602–2610). In another study, resistance was correlated with the appearance of an altered P-450 target protein with decreased affinity for fluconazole (Hitchcock, *Biochem Soc. Trans.*, 1993, 21:1039–1047). However, fluconazole resistance appears to be primarily due to decreased accumulation of the drug in resistant cells (Vanden Bossche, et al., 1994; Odds, 1993, supra). Species intrinsically resistant to fluconazole such as *C. glabrata*, *C. krusei* and *Aspergillus fumigatus* have also been shown to accumulate less fluconazole (Vanden Bossche, et al., 1994, supra). *C. glabrata* and *C. krusei*, on the other hand, have been shown to accumulate itraconazole and to be susceptible to that compound (Marichal et al., *Mycoses*, 1995, 38:111–117). Thus, it appears that both intrinsic and acquired resistance may be due to decreased drug accumulation in the cell. There are several ways in which a cell can manipulate the intracellular concentration of a compound. One is preventing the compound from gaining access to the interior of the cell in the first place. Another is metabolic decomposition of the compound once it is in the cell. A further means is simply excreting the intact compound before it can have any effect on the cell. This latter approach is called efflux and the cell components involved in efflux, i.e., membrane transporter proteins, are called efflux pumps.

Efflux pumps are ubiquitous in all types of cells, from bacterial to mammalian (Higgins, *Ann. Rev. Cell Biol.*, 1992, 8:67–113). Efflux is driven either by the energy of ATP hydrolysis (ABC-transporter superfamily) or by proton transfer (Major Facilitator superfamily). Efflux pumps exhibit differing degrees of specificity.

Some efflux pumps are extremely specific, such as the TetA pump in gram-negative bacteria, which effluxes tetracycline only. Others are less specific; e.g., the MsrA protein in *Staphyloccus aureus* effluxes not only erythromycin but related macrolides as well. There are also efflux pumps that are quite general in their efflux capability, excreting a variety of structurally unrelated compounds from a cell. Many efflux pumps are clinically significant.

Resistance to chemotherapeutics in some mammalian cancer cells has been attributed to a multi-drug resistant efflux pump known as P-glycoprotein (Pgp) (Gottesman, et al., *Ann. Rev. Biochem.*, 1993, 62:385–427). *Pseudomonas aeruginosa*, which causes respiratory infections, adventitious infection in burn patients, etc., uses Mex efflux pumps to eliminate quinolones, as well as other structurally unrelated antibiotics (Nikaido, *Science*, 1994, 264:382–388). Multiple-drug resistant (MDR) efflux pumps have been implicated in fluconazole resistance in *C. albicans* and *C. glabrata* (Parkinson, et al., *Antimicrob. Agents Chemother.*, 1995, 39:1696–1699; Sanglard, et al., *Antimicrob. Agents Chemother.*, 1995, 39:2378–2386; Albertson, et al., *Antimicrob. Agents Chemother.*, 1996, 40:2835–2841).

Based on the above, it would clearly be desirable to be able to inhibit the activity of fungal efflux pumps so that anti-fungal agents can accumulate in fungal cells in sufficient quantity to exert their effect. The present invention provides compounds that achieve this goal.

SUMMARY OF THE INVENTION

The present invention relates to compounds that are fungal efflux pump inhibitors. When administered to a patient suffering from an infection caused by a fungal species that employs efflux pump(s) as a resistance mechanism, the compounds inhibit the activity of the pump(s) allowing a co-administered anti-fungal agent to accumulate in sufficient concentration to inhibit fungal cells and treat the infection.

Thus, in one aspect the present invention relates to a compound having the chemical formula:

or a pharmaceutically acceptable salt thereof, wherein:

$A_1$ is carbon or nitrogen, provided that when $A_1$ is nitrogen, $R^5$ does not exist;

$R^2$ and $R^3$ are independently selected from the group consisting of hydrogen, halo and —O(1C–4C)alkyl;

$R^4$ and $R^6$ are independently selected from the group consisting of hydrogen, halo, —O(1C–4C)alkyl, —OCF$_3$, and O—CH$_2$(3C–6C)cycloalkyl;

$R^5$ is selected from the group consisting of hydrogen and $R^7$ and $R^8$ are independently selected from the group consisting of hydrogen, halo, —C≡N, —O(1C–4C)alkyl, —OCHF$_2$, —OCF$_3$ and, taken together, —OCH$_2$O—;

$R^1$ is selected from the group consisting of —(1C–4C)alkyl, -(3C–6C)cycloalkyl, wherein:

$A_4$ is selected from the group consisting of —NH, oxygen and sulfur;

$A_2$, $A_3$ and $A_5$ are independently selected from the group consisting of carbon and nitrogen provided that no more than two of $A_2$, $A_3$ and $A_5$ are nitrogen at the same time;

or, $R_1$ is —C(O)(CH$_2$)$_n$(R$^{22}$)R$^9$, wherein, n is 0, 1, 2 or 3;

$R^9$ is selected from the group consisting of hydrogen, —OH, —(1C–4C)alkyl, -(3C–6C)cycloalkyl, —CH$_2$(3C–6C)cycloalkyl, wherein:

$A_6$, $A_7$ and $A_8$ are independently selected from the group consisting of carbon, oxygen, sulfur and NR$^{15}$;

$A_9$, $A_{10}$ and $A_{11}$ are independently selected from the group consisting of carbon and nitrogen;

$R^{10}$ and $R^{11}$ are independently selected from the group consisting of hydrogen, -(1C–4C)alkyl, —SO$_2$R$^{16}$, —C(O)R$^{16}$ and —C(O)OR$^{16}$, wherein:

$R^{16}$ is selected from the group consisting of hydrogen and -(1C–4C)alkyl wherein the alkyl group may be substituted with 1, 2, 3, or 4 fluorines;

$R^{12}$ is selected from the group consisting of hydrogen, -(1C–4C)alkyl, -(3C–6C)cycloalkyl, —CH$_2$(3C–6C)cycloalkyl, —C(O)O-(1C–4C)alkyl, —SO$_2$R$^{17}$ and —SO$_2$NR$^{18}$R$^{19}$, wherein, $R^{17}$, $R^{18}$ and $R^{19}$ are independently selected from the group consisting of hydrogen and -(1C–4C)alkyl;

$R^{14}$ and $R^{15}$ are independently selected from the group consisting of hydrogen, -(1C–4C)alky and —NR$^{10}$R$^{11}$;

$R^{22}$ is selected from the group consisting of hydrogen and (1C–4C)alkyl;

or, $R^9$ is —C(R$^{16}$)(R$^{20}$)(CH$_2$)$_p$NR$^{10}$OR$^{11}$, wherein:

p is 0, 1 or 2;

$R^{20}$ is selected from the group consisting of hydrogen and -(1C–4C)alkyl, the alkyl group being optionally substituted with an entity selected from the group consisting of —OH, —O(1C–4C)alkyl, —C≡N, —SO$_2$(1C–4C)alkyl and

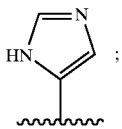

and, the compound comprises a racemic mixture, a pure enantiomer or a pure atropisomer of either the racemic mixture or the pure enantiomer.

In an aspect of this invention, the compound is in the S absolute configuration at the starred carbon.

In an aspect of this invention, in the above compounds, $A_1$ is carbon and $R^{22}$ is selected from the group consisting of hydrogen and —CH$_3$.

In an aspect of this invention, in the above compounds, $A_1$ is nitrogen.

In an aspect of this invention, in the above compounds, $R^4$ and $R^6$ are independently selected from the group consisting of —O(1C–4Calkyl) and —OCH$_2$(3C–6C)cycloalkyl.

In an aspect of this invention, in the above compounds, $R^4$ and $R^6$ are OCH$_3$.

In an aspect of this invention, in the above compounds, $R^7$ is selected from the group consisting of hydrogen and halogen and $R^8$ is hydrogen.

In an aspect of this invention, in the above compounds, $R^7$ is fluorine.

In an aspect of this invention, in the above compounds, $R^6$ is selected from the group consisting of —OCH$_3$ and

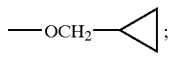

and,
$R^7$ is F.

In an aspect of this invention, in the above compounds, $R^6$ is selected from the group consisting of —OCH$_3$ and

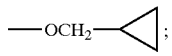

and,
$R^5$ is —C(O)CH$_3$.

In an aspect of this invention, in the above compounds, $R^4$ and $R^6$ are

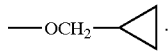

In an aspect of this invention, in the above compounds, $R^{21}$ is —NHSO$_2$CH$_3$.

In an aspect of this invention, in the above compounds, $R^5$ is

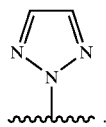

An aspect of this invention is a method for inhibiting a fungal cell that employs an efflux pump resistance mechanism, comprising contacting the cell with an anti-fungal agent and any one of the above compounds.

In an aspect of this invention, in the above method, the anti-fungal agent is an azole anti-fungal agent.

In an aspect of this invention, in the above method, the azole fungicide is selected from the group consisting of fluconazole and posaconazole.

In an aspect of this invention, in the above method, the fungal cell is first contacted with the compound and then with the anti-fungal agent.

In an aspect of this invention, in the above method, the fungal cell is contacted with the compound and the anti-fungal agent simultaneously.

In an aspect of this invention, in the above method, the fungal cell is a genus Candida cell.

In an aspect of this invention, in the above method, the fungal cell is a genus Aspergillus cell.

An aspect of this invention is a method for treating an infection caused by a fungus that employs an efflux pump resistance mechanism, comprising administering to a patient in need thereof a therapeutically effective amount of an anti-fungal agent and an one of the above compounds.

In an aspect of this invention, in the above method, the infection is caused by a genus Candida fungus.

In an aspect of this invention, in the above methods, the Candida fungus is *C albicans, C. krusei, C. tropicalis, C. parapsilosis* or *C. glabrata.*

In an aspect of this invention, in the above methods, the infection is caused by a genus Aspergillus fungus.

In an aspect of this invention, in the above methods, the genus Aspergillus fungus is *Aspergillus fumigatus.*

In an aspect of this invention, in the above method, the compound and the anti-fungal agent are contacted with the fungal cell or administered to the patient simultaneously.

In an aspect of this invention, in the above method, the compound is contacted with the fungal cell or administered to the patient first followed by contact with or administration of the anti-fungal agent.

An aspect of this invention is a pharmaceutical composition comprising a pharmaceutically acceptable carrier or excipient and any of the above compounds.

In an aspect of this invention, the above pharmaceutical composition further comprises a therapeutically effective amount of an anti-fungal agent.

In an aspect of this invention, in the above pharmaceutical composition, the anti-fungal agent is an azole anti-fungal agent.

In an aspect of this invention, in the above pharmaceutical composition, the azole anti-fungal agent is fluconazole or posaconazole.

DETAILED DESCRIPTION OF THE INVENTION

Brief Description of the Tables

Table 1 shows representative racemic N-methylpiperazine compounds of this invention.

Table 2 shows representative racemic compounds of this invention other than N-methylpiperazines.

Table 3 shows representative S-absolute configuration compounds of this invention.

Table 4 provides data regarding the potentiation, by representative compounds of this invention, of fluconazole against a *Candida albicans* strain over-expressing CDR1 and CDR2 efflux pumps.

Table 5 provides data regarding the potentiation, by representative compounds of this invention, of fluconazole against a *Candida glabrata* strain over-expressing $C_gCDR1$ and $C_gCDR2$ efflux pumps.

Definitions

As used herein, the term "alkyl" refers to a straight or branched chain saturated aliphatic hydrocarbon. Preferably, the alkyl group consists of 1 to 20 carbon atoms (whenever a numerical range such as "1–20" or "1 to 20" is provided herein, it means that the group may consist of 1 carbon atom, 2 carbon atoms, 3 carbon atoms, etc., up to and including 20 carbon atoms). More preferably, an alkyl group of this invention is a medium size alkyl having 1 to 10 carbon atoms. Most preferably, it is a lower alkyl having 1 to 4 carbon atoms. The size of an alkyl may be indicated by the formula $(C_a-C_b)$alkyl where a and b are integers from 1 to 20 and indicate how may carbons are in the alkyl chain. For example, a $(C_1-C_4)$alkyl refers to a straight or branched chain alkyl consisting of 1, 2, 3 or 4 carbon atoms. An alkyl group may be substituted or unsubstituted. When substituted, the substituent group(s) is preferably one or more independently selected from the group consisting of $(C_3-C_6)$cycloalkyl, halo, hydroxy, alkoxy, acyloxy, amino, acylamino, amido, carboxy, carbonyl, alkylcarbonyl, alkoxycarbonyl, cyano and nitro.

A "cycloalkyl" group refers to a 3 to 8 member all-carbon monocyclic ring. The designation $(C_3-C_6)$cycloalkyl, for example, refers to a 3-, 4-, 5- or 6-member all-carbon ring. A cycloalkyl group may contain one or more double bonds but it does not contain a fully conjugated pi-electron system; i.e., it is not aromatic. Examples, without limitation, of cycloalkyl groups are cyclopropane, cyclobutane, cyclopentane, cyclopentene, cyclohexane, cyclohexadiene, adamantane, cycloheptane and, cycloheptatriene. A cycloalkyl group may be substituted or unsubstituted. When substituted, the substituent group(s) is preferably one or more independently selected from the group consisting of unsubstituted $(C_1-C_4)$alkyl, halo, hydroxy, alkoxy, acyloxy, amino, acylamino, amido, carboxy, carbonyl, alkylcarbonyl, alkoxycarbonyl, cyano and nitro.

An "alkenyl" group refers to an alkyl group, as defined herein, having at least two carbon atoms and at least one carbon-carbon double bond. As used herein, $(C_2-C_4)$ alkenyl, for example, refers to a 2, 3, or 4 carbon alkenyl group.

An "aryl" group refers to an all-carbon monocyclic or a fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group may be substituted or unsubstituted. When substituted, the substituted group(s) is preferably one or more independently selected from the group consisting of alkyl, halo, (halo)$_3$C-, hydroxy, alkoxy, acyloxy, amino, acylamino, amido, carboxy, carbonyl, alkylcarbonyl, alkoxycarbonyl, cyano and nitro.

As used herein, a "heteroaryl" group refers to a monocyclic or fused ring in which one or more of the rings contains one or more atoms selected from the group consisting of nitrogen, oxygen and sulfur and, in addition, sufficient double bonds to establish a fully conjugated pi-electron system. Examples, without limitation, of heteroaryl groups are pyrrole, furan, thiophene, imidazole, oxazole, thiazole, pyrazole, pyridine, pyrimidine, quinoline, isoquinoline, purine and carbazole. A heteroaryl group may be substituted or unsubstituted. When substituted, the substituted group(s) is preferably one or more independently selected from the group consisting of alkyl, halo, (halo)$_3$C-, hydroxy, alkoxy, acyloxy, amino, acylamino, amido, carboxy, carbonyl, alkylcarbonyl, alkoxycarbonyl, cyano and nitro.

A "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. The heteroalicyclic ring may be substituted or unsubstituted. When substituted, the substituted group(s) is preferably one or more independently selected from the group consisting of alkyl, halo, (halo)$_3$C-, hydroxy, alkoxy, acyloxy, amino, acylamino, amido, carboxy, carbonyl, alkylcarbonyl, alkoxycarbonyl, cyano and nitro.

An "halo" group refers to fluorine, chlorine, bromine or iodine.

An "hydroxy" group refers to an —OH group.

An "alkoxy" group refers to an —O(alkyl) group.

An "acyloxy" group refers to an —OC(O)(alkyl) group.

An "amino" group refers to an —NRR' group wherein R and R' are independently selected from the group consisting of hydrogen and alkyl, wherein the alkyl group is not further substituted.

An "acylamino" group refers to a —NRC(O)(alkyl) group wherein R is selected from the group consisting of hydrogen and unsubstituted alkyl.

An "amido" group refers to a —C(O)NRR' group wherein R and R' are independently selected from the groups consisting of hydrogen and alkyl, the alkyl group being not further substituted.

A "carboxy" group refers to a —C(O)OH group.

A "carbonyl" group refers to a —C(O)H group.

An "alkylcarbonyl" group refers to a —C(O)(alkyl) group.

An "alkoxycarbonyl" group refers to a —C(O)O(alkyl) group wherein the alkyl group is not further substituted.

A "cyano" group refers to a —C≡N group.

A "nitro" group refers to a —NO$_2$ group.

"t-Boc" refers to a t-butoxycarbonyl group; i.e., (CH$_3$)$_3$COC(=O)—.

The term "efflux pump" refers to a protein assembly which exports molecules from the cytoplasm or periplasm of a cell to the external environment in an energy dependent fashion.

An "efflux pump inhibitor" is a compound which interferes with the ability of an efflux pump to export molecules from a cell. In particular, the efflux pump inhibitors of this invention interfere with a pump's ability to excrete therapeutic anti-fungal agents from fungal cells.

By a fungus that "employs an efflux pump resistance mechanism" is meant that the fungal cells are known or are shown to excrete anti-fungal agents from their cytoplasm or periplasm to the external environment and thereby reduce the concentration of the anti-fungal agent in the cells to below that necessary to inhibit the growth and/or proliferation of the cells.

In the context of cell growth, the term "inhibit" means that the rate of growth and/or proliferation of a cellular population is decreased, preferably stopped. By "stopped" is preferably meant permanently; that is, the cells are killed. Inhibition can be monitored by, for example, comparing the difference in turbidity of liquid cultures, or the difference in plaque size for cultures on solid media, in the presence and absence of an inhibitory agent.

As used herein, the term "overproduces" refers to the presence in a fungal strain of a significantly greater amount of a functional efflux pump or pumps than that found in most naturally-occurring (usually non-nosocomial) isolates of that strain. A strain that overproduces an efflux pump would, of course, be expected to more efficiently export substrate molecules. In contrast, a "wild-type" strain will produce an efflux pump or pumps at a level that is typical of natural isolates of a particular fungal species.

As used herein, the term "anti-fungal agent" refers to a compound that is either fungicidal or fungistatic. A fungicide kills fungal cells while a fungistat slows or stops cell growth and/or proliferation so long as the compound is present. The efflux pump inhibitors of this invention may be somewhat fungicidal or fungistatic in their own right, but their primary utility resides in their ability to potentiate other anti-fungal agents by inhibiting efflux pump activity in resistant fungal strains.

An "azole" anti-fungal agent refers to any member of those classes of anti-fungal agents characterized by one or more imidazole or triazole rings in their chemical structure. Examples, without limitation, of anti-fungal azole compounds are butoconazole, clotrimazole, fenticonazole, ketoconazole, sulfconazole, fluconazole, itraconazole, terconazole, posaconazole, triticonazole, imibenconazole, voriconazole, and metaconazole.

By "potentiation" of an anti-fungal agent is meant that a compound of this invention counteracts the efflux resistance mechanism in a fungal strain sufficiently for an anti-fungal agent to inhibit the growth and/or proliferation of fungal cells at a lower concentration than in the absence of the compound. In cases where resistance is essentially complete, i.e., an anti-fungal compound has no effect on the fungal cells, potentiation means that, in the presence of a compound of this invention, the anti-fungal agent inhibits the fungus and thereby treats the infection at a pharmaceutically acceptable dosage.

A "sub-inhibitory concentration" of an anti-fungal agent refers to a concentration that is less than that required to inhibit a majority of the cells in a population of a fungal species. Generally, a sub-inhibitory concentration refers to a concentration that is less than the Minimum Inhibitory Concentration (MIC), which is defined, unless specifically stated to be otherwise, as the concentration required to produce an 80% reduction in the growth or proliferation of a target fungus.

As used herein, the term "treat," treatment," or "treating" refers to the administration of a therapeutically or prophylactically effective amount of a composition comprising a compound of this invention together with an anti-fungal agent to a patient in need of such treatment.

As used herein, "infect," or "infection" refers to the establishment in a patient of a population of a fungus that results in a deleterious effect on the health or well-being of the patient and/or gives rise to discernable symptoms associated with the particular fungus.

A "pharmaceutical composition" refers to a mixture of one or more of the compounds described herein, or physiologically acceptable salts or prodrugs thereof, with other chemical components, such as pharmaceutically acceptable carriers and excipients. The purpose of a pharmaceutical composition is to facilitate administration of a compound to a patient.

A "pharmaceutically acceptable salt" of a compound of this invention refers to the compound in a charged form together with a counter-ion. In general, a compound of this invention will be a positively charged species, usually in the form of an ammonium cation. In such case, the negatively charged counter-ion is a pharmaceutically acceptable anion such as, without limitation, chloride, bromide, iodide, nitrate, phosphate, sulfate, acetate, trifluoroacetate, propionate, butyrate, maleate, fumarate, methanesulfonate, ethanesulfonate, 2-hydroxyethyl-sulfonate, n-propylsulfonate isopropylsulfonate, lactate, malate or citrate. Pharmaceutically acceptable salts in which the compound of this invention forms the positively-charged species are obtained by reacting the compound with the appropriate acid. For example, to make an ammonium chloride salt of a compound of this invention, the compound would be reacted with hydrochloric acid.

A "prodrug" refers to a compound, which is converted into the parent drug in vivo. Prodrugs are often useful because they may be easier to administer than the parent drug. They may, for instance, be bioavailable by oral administration whereas the parent drug is not. A prodrug may also have improved solubility in pharmaceutical compositions over the parent drug. An example, without limitation, of a prodrug would be a compound which is administered as an ester (the "prodrug") to facilitate transmittal across a hydrophobic cell membrane where water solubility is detrimental. The ester is then metabolically hydrolyzed in the cell to the carboxylic acid, which is the active entity.

A further example of a prodrug would be a short polypeptide such as, without limitation, a 2 to 10 amino acid polypeptide, which is bonded through a terminal amino group to a carboxy group of a compound of this invention. The polypeptide may also bond through a terminal carboxy group with an amino group of a compound herein. The polypeptide hydrolyzes or is metabolized in vivo to release the active molecule.

As used herein, a "pharmaceutically acceptable carrier" refers to a carrier or diluent that does not cause significant irritation to a patient and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the terms "prevent", "preventing" and "prevention" refer to a method for barring a patient from acquiring a fungal infection in the first place.

As used herein, the terms "treat", "treating" and "treatment" refer to a method of alleviating or abrogating a fungal infection and/or its attendant symptoms once a patient has been infected.

As used herein, "administer," administering," or "administration" refers to the delivery to a patient of a compound, salt or prodrug of the present invention or of a pharmaceutical composition containing a compound, salt or prodrug of this invention to a patient for the purpose of inhibiting a fungal efflux pump. It also refers to the delivery of a composition comprising a compound, salt or prodrug of this invention in combination with an anti-fungal agent, in which case the purpose is the treatment or prevention of a fungal infection.

The term "patient" refers to any living entity capable of being infected by a fungus. In particular, a "patient" refers to a mammal such as a dog, cat, horse, cow, pig, rabbit, goat or sheep. Most particularly, a patient refers to a human being.

The term "therapeutically effective amount," as used herein, refers to that amount of a compound of this invention that, together with an anti-fungal agent, will relieve to some extent one or more of the symptoms of a fungal infection. In particular, a therapeutically effective amount refers to that amount of a compound of this invention that, together with an anti-fungal agent: (1) reduces, preferably eliminates, the population of fungal cells in the patient's body, (2) inhibits (i.e., slows, preferably stops) proliferation of the fungal cells, (3) inhibits (i.e., slows, preferably stops) spread of the infection, and/or, (4) relieves (preferably, eliminates) one or more symptoms associated with the infection.

The term "prophylactically effective amount" refers to that amount of a compound of this invention and an anti-fungal agent that has the effect of (1) maintaining a reduced level of a population of fungal cells achieved by a previously administered therapeutically effective amount of the compounds; (2) maintaining the level of inhibition of proliferation of fungal cells achieved by administration of a therapeutically effective amount; (3) maintaining the degree of inhibition of spread of the infection achieved by a therapeutically effective amount; and/or (4) maintaining the level of relief of one or more symptoms or, or if symptoms were eliminated, maintaining the non-existence of symptoms associated with a fungal infection achieved by administration of a therapeutically effective amount of the compound of this invention. A prophylactically effective amount also refers to that amount of a composition comprising a compound of this invention and an anti-fungal agent that will prohibit a fungus from accumulating in a susceptible organism in sufficient amount to cause an infection. An example of a susceptible organism would be an immunocompromised patient such as someone who has undergone transplant surgery and therefore is being treated with immuno-suppressants, or a person suffering from AIDS.

"In vitro" refers to procedures performed in an artificial environment such as, e.g., without limitation, a test tube or culture medium.

"in vivo" refers to procedures performed within a living organism such as, without limitation, a mouse, rat or rabbit.

A "racemic mixture" refers to a 1:1 mixture of two optical isomers.

The letters "R" and "S" are used to designate the absolute stereochemistry at an asymmetric carbon. Whether a particular asymmetric carbon atom is R or S is determined by application of the Cahn-lngold-Prelog (C-I-P) rules (*Angew. Chem.*, 1966, 78:413–447). The rules are so well known to those skilled in the art that they need not be described in detail herein.

Relative stereochemistry refers to the configuration of any asymmetric carbon with respect to any other asymmetric carbon in the same molecule. Unlike absolute configuration, relative configuration is reflection-invariant, that is, it does not affect optical isomerism.

The term "atropisomer" refers to a subclass of conformers (stereoisomers that can be interconverted by rotation about a single bond) that arise as the result of restricted rotation about the single bond. Each conformer represents a potential energy minimum. Thus, each conformer can be isolated as separate chemical species. Reference herein to "a pure atropisomer" refers to a compound wherein greater than 90%, preferably greater than 95%, most preferably greater than 98% of the molecules comprise a single restricted rotation conformer.

A "pure enantiomer" refers to a compound that is greater than 90%, preferably greater than 95% and, most preferably, greater than 98% a single optical isomer.

Discussion

The present invention relates to the inhibition of efflux pump activity in fungal species and the concurrent potentiation of anti-fungal agents. The identification and use of efflux pump inhibitors is described in Chamberland et al., Internat. Patent Appl. No. PCT/US96/05469, WO96/33285, entitled "Efflux Pump Inhibitors." The following is a description of several efflux pumps that confer resistance to fluconazole on Candida Spp. The description is exemplary only and is not intended to limit the scope of this invention in any manner whatsoever.

Three MDR pumps have been demonstrated to confer resistance to fluconazole in clinical isolates of *C. albicans* (Sanglard et al., 1996, *Antimicrob. Ag. Chemother.* 40:2300–2305). These pumps are CDR1 (ABC-family, Prasad et al., 1995, *Curr. Genet.*, 27:320–329), CDR2 (ABC-family, Sanglard et al, 1996, supra) and BenR (MF-family, Benyaakov et al., 1994). The genes which encode CDR1 and CDR2, i.e., cdr1 and cdr2, have been shown to be over-expressed in several *C. albicans* isolates from AIDS patients with whom fluconazole therapy has failed. Strains that over-express these genes have also been shown to be resistant to ketoconazole and itraconazole. Over-expression of benR, on the other hand, conferred resistance to fluconazole only. To further explore the resistance mechanism, *C. albicans* strains were prepared in which the genes expressing individual pumps were deleted. Strains were also produced having multiple gene deletions to further study specificity of the pumps and their role in intrinsic resistance to azole anti-fungals. CDR1 was shown to play a significant role in the intrinsic resistance of *C. albicans* to azoles in that deletion of the cdr1 gene rendered the strain more susceptible. Deletion of the CDR2 and BenR genes also contributed to intrinsic resistance, but only when cdr1 was also deleted. A *C. albicans* mutant which was deprived of all known efflux pumps was 30-fold more susceptible to azole anti-fungal agents than the parent strain.

In another study, two homologs of cdr1 and benR, cgcdr and cgben, were cloned from resistant *C. glabrata* suggesting that a similar resistance mechanism was at work in that species. An active efflux pump in azole-resistant *Aspergillus nidulans* has also been identified (Waard and van Nistelrooy, 1980, *Pesticide Biochem. Physiol.* 13:255–266).

Thus, it appears that, in general, strains that are cross-resistant to several anti-fungal azoles tend to over-express CDR1-type broad-spectrum pumps while strains that are resistant only to fluconazole over-express the narrow-spectrum BenR-type pump.

Compounds of this invention are capable of effectively inhibiting several of the above efflux pumps. They may be used to combat both intrinsic and acquired resistance and may in fact expand the spectrum of activity of anti-fungal agents against previously non-susceptible species.

The compounds of this invention are particularly effect in overcoming efflux pump-mediated resistance to azole anti-fungals, especially fluconazole and posaconazole.

Synthesis

The following are General Methods (GM) for the synthesis of the racemic and the enatiomerically enhanced compounds of this invention. Neither the syntheses nor any of the compounds described below are intended, nor are they to be construed, as limiting the scope of this invention in any manner whatsoever. Other approaches to the synthesis of the compounds will become apparent to those skilled in the art based on the disclosures herein and are within the scope of this invention.

The compounds of this invention were characterized by mass spectrometry and their relative retention times (RT) under the following chromatographic protocol:

System: HP1100
Column: Zorbax XDB C18 150 × 3 mm, 3.5u
Flow rate: 0.4 ml/min
UV detn: 240,254 nm
Buffer: 0.1M ammonium acetate, pH 6.0
Organic: acetonitrile
Gradient:

| Time(min) | % buffer | % organic |
|---|---|---|
| 0 | 90 | 10 |
| 2 | 90 | 10 |
| 42 | 20 | 80 |
| 47 | 20 | 80 |
| 50 | 90 | 10 |
| 58 | 90 | 10 | compounds that were purified by HPLC, the following protocol was used:

For column—Polaris C18, 100×21.2 mm
Flow rate—20 mL per minute
Gradient—0–5 min 10% acetonitrile; 5–20 min 10% acetonitrile to 100% acetonitrile; 20–22 min 100% acetonitrile.

GM for N-methyl Piperazines (Racemic)

Compound 213

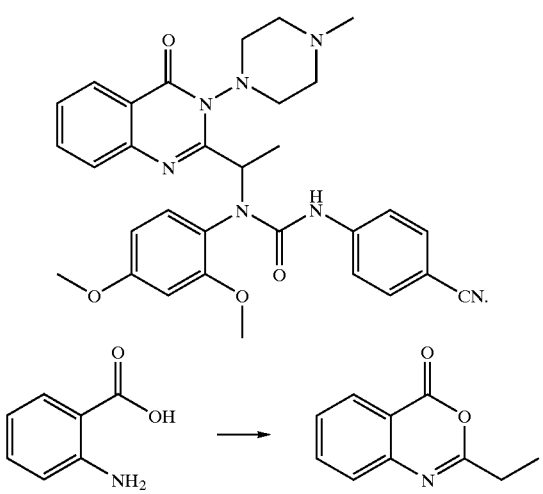

A solution of anthranilic acid (15 g, 109.4 mmol) in 21 mL (164.1 mmol) of propionic anhydride was stirred at 100° C. for 1.5 hours. The excess propionic anhydride was evaporated (15 torr, 80° C. water bath). The crude mass was co-evaporated three times with toluene to give 18.72 g of A.

$^1$H-NMR (300 MHz, DMSO-d$_6$) δ: 1.23 (t, J=7.8 Hz, 3H), 2.67 (q, J=7.8 Hz, 2H), 7.50–7.65 (m, 2H), 7.89 (dt, J=7.6, 1.8 Hz, 1H), 8.07 (dd, J=7.6, 1.8 Hz, 1H).

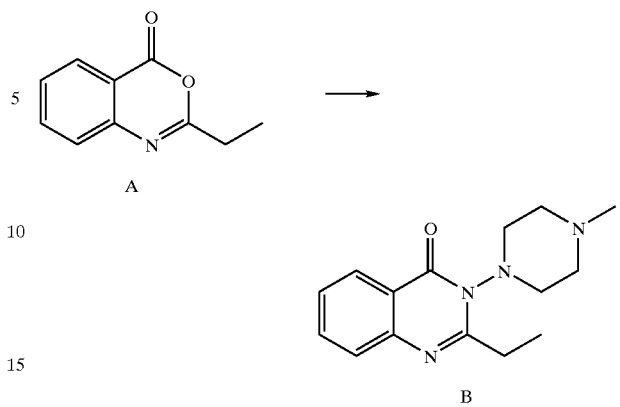

To a suspension of A (18.72 g 107.0 mmol) in 28 mL of acetic acid was dropwise added 1-amino-4-methylpiperazine (13.48 mL, 112.0 mmol). The mixture was stirred at 90° C. for 14 hours before being evaporated and co-evaporated three times with toluene. The residue was dissolved in water and the pH of the solution was adjusted to 3 by addition of 1M aqueous hydrochloric acid. The aqueous layer was extracted three times with ethyl ether and the combined organic layers were discarded. The aqueous layer was basified to pH 11 by addition of 2M aqueous sodium hydroxide. After saturation by addition of solid sodium chloride and three extractions with ethyl acetate, the combined organic layers were washed with water, dried over sodium sulfate, filtered through cotton and evaporated in vacuo to give 20.71 g of B.

$^1$H-NMR (300 MHz, DMSO-d$_6$) δ: 1.23 (t, J=7.3 Hz, 3H), 2.15 (m, 2H), 2.21 (s, 3H), 2.76 (m, 2H), 2.80–2.95 (m, 4H), 3.96 (m, 2H), 7.45 (dt, J=8.1, 1.5 Hz, 1H), 7.58 (dd, J=8.1, 1.5 Hz, 1H), 7.76 (dt, J=8.1, 1.5 Hz, 1H), 8.06 (dd, J=8.1, 1.5 Hz, 1H).

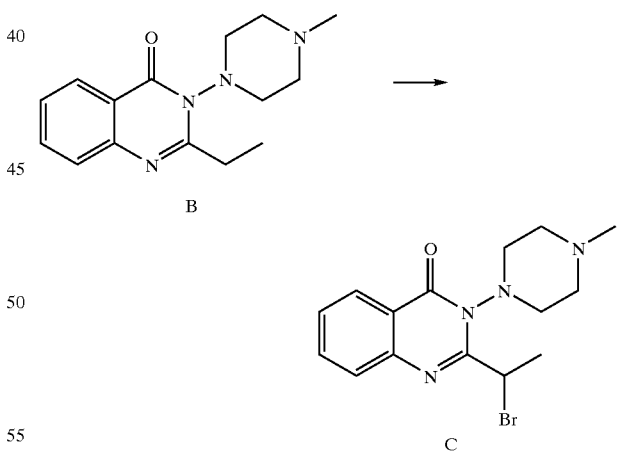

To a solution of B (5 g, 18.4 mmol) and sodium acetate (3.4 g, 41 mmol) in 30 mL of acetic acid was added pyridinium tribromide (11.8 g, 37 mmol). The resulting mixture was stirred at 50° C. for two hours before being cooled to 0° C. The precipitate was filtered off and washed with acetic acid and hexanes. The resulting powder was suspended in water and the pH was adjusted to 9 by addition at 0° C. of a saturated solution of aqueous potassium carbonate. The white solid was filtered, rinsed with water and dried in vacuo to give 4.2 g of C.

¹H-NMR (300 MHz, DMSO-d₆) δ: 2.01 (d, J=6.6 Hz, 3H), 2.28 (s, 3H), 2.34 (m, 2H), 2.85 (m, 2H), 3.04 (m, 2H), 3.94–4.03 (m, 2H), 5.72 (q, J=6.6 Hz, 1H), 7.55 (dt, J=8.1, 1.5 Hz, 1H), 7.68 (dd, J=8.1 Hz, 1.5 Hz, 1H), 7.84 (dt, J=8.1, 1.5 Hz, 1H), 8.12 (dd, J=8.1, 1.5 Hz, 1H). MS (ES+) m/z 351/353 (M⁺+H).

1H), 6.34 (dd, J=8.7, 2.5 Hz, 1H), 6.44 (d, J=2.5 Hz, 1H), 6.61 (d, J=8.7 Hz, 1H), 7.40 (dt, J=8.1, 1.5 Hz, 1H), 7.58–7.74 (m, 2H), 8.20 (dd, J=8.1, 1.5 Hz, 1H). MS (ES+) m/z 424 (M⁺+H).

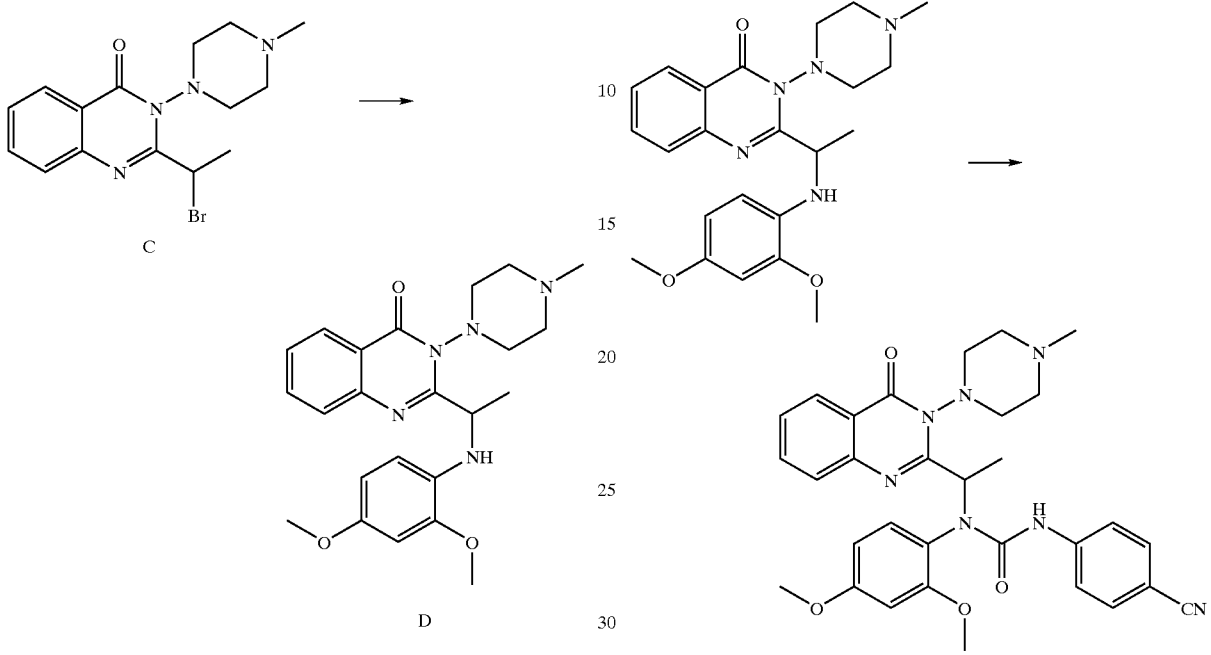

A suspension of C (1.5 g, 4.27 mmol), 2,4-dimethoxyaniline (0.785 g, 5.12 mmol) and potassium carbonate (0.708 g, 5.12 mmol) in 11 mL of anhydrous dimethylformamide was heated at 85° C. for 4.5 hours. The resulting mixture was diluted with water and extracted three times with a 3/1 (v/v) mixture of ethyl acetate and hexanes. The combined organic layers were washed with water, dried over anhydrous sodium sulfate, filtered, and evaporated to give a dark brown oil which was purified by flash chromatography on silica gel (ethyl acetate/methanol 100/0 to 97.5/2.5 to 95/5 to 90/10) to give 1.688 g of D.

¹H-NMR (300 MHz, CDCl₃) δ: 1.59 (d, J=6.6 Hz, 3H), 2.26–2.50 (m, 2H), 2.39 (s, 3H), 2.78–3.00 (m, 4H), 3.71 (s, 3H), 3.86 (s, 3H), 4.27, 4.34 (2 m, 2H), 5.20 (q, J=6.6 Hz,

To a solution of D (15 mg, 0.035 mmol) in 1 mL of anhydrous 1,2-dichloroethane was added 4-cyanophenylisocyanate (10 mg, 0.07 mmol). The resulting mixture was heated at 60° C. for 12 hours. Upon removal of solvent, the crude material was purified by HPLC to give 7.0 mg of product. MS (ES+) m/z 469 (M⁺+H); relative retention time 28.0 min.

Table 1 shows additional N-methyl piperazines that were synthesized using the above procedures. The starting materials used to get the different products are shown in the last column.

TABLE 1

| Cmpd | Structure | MS | RT (min) | Starting materials |
|------|-----------|-----|----------|--------------------|
| 214 | 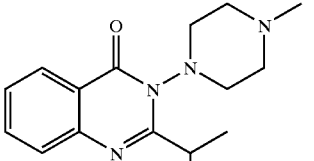 | 610 (M + H) | 29.1 | 4-(difluoromethoxy)phenyl isocyanate |

TABLE 1-continued

| Cmpd | Structure | MS | RT (min) | Starting materials |
|---|---|---|---|---|
| 215 | 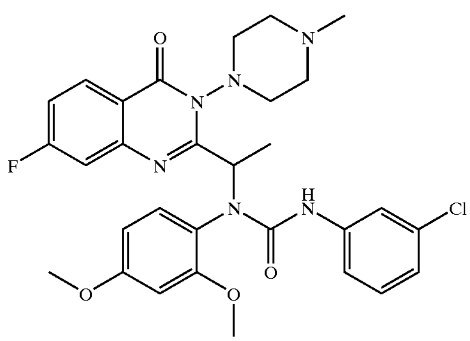 | 595/7 (M + H) | 34.0 | 2-amino-4-fluoro-benzoic acid, 3-chlorophenyl isocyanate |
| 216 | 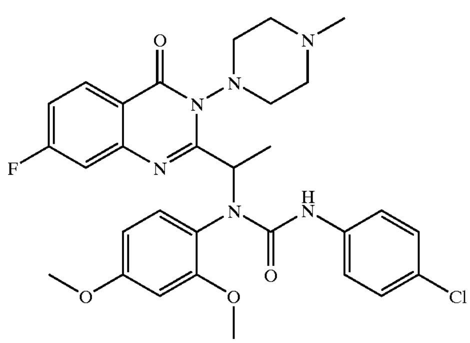 | 595/7 (M + H) | 33.5 | 2-amino-4-fluoro-benzoic acid, 4-chlorophenyl isocyanate |
| 217 | 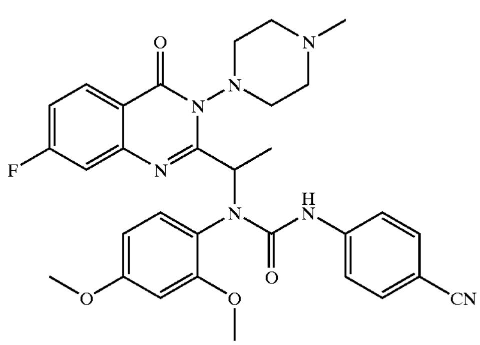 | 587 (M + H) | 30.2 | 2-amino-4-fluoro-benzoic acid |
| 218 | 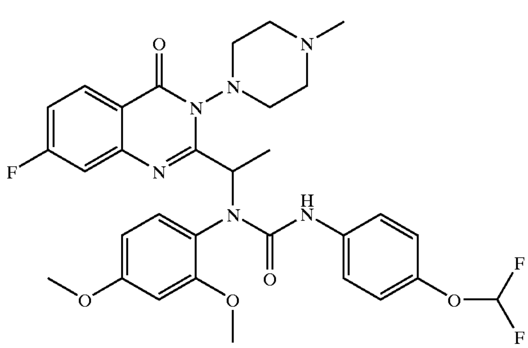 | 628 (M + H) | 31.5 | 2-amino-4-fluoro-benzoic acid, 4-(difluoromethoxy)phenyl isocyanate |

TABLE 1-continued

| Cmpd | Structure | MS | RT (min) | Starting materials |
|---|---|---|---|---|
| 219 | 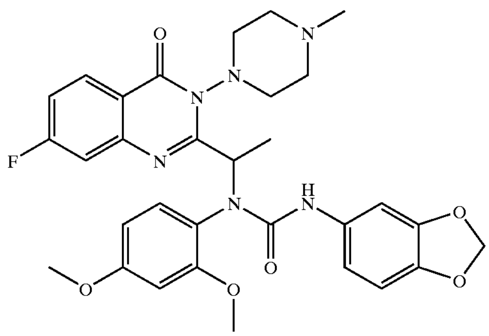 | 606 (M + H) | 28.2 | 2-amino-4-fluoro-benzoic acid, 5-isocyanato-benzo[1,3]dioxole |
| 220 | 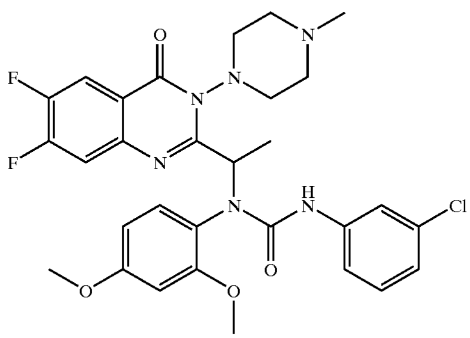 | 613/5 (M + H) | 35.7 | 2-amino-4,5-difluoro-benzoic acid, 3-chlorophenyl isocyanate |
| 221 | 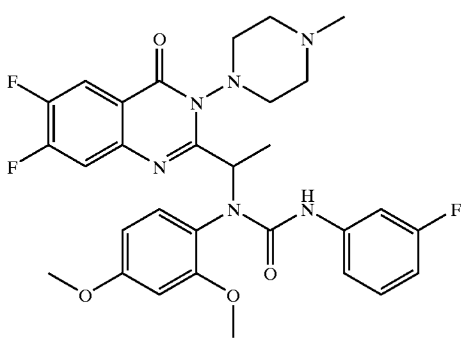 | 598 (M + H) | 33.4 | 2-amino-4,5-difluoro-benzoic acid, 3-fluorophenyl isocyanate |
| 222 | 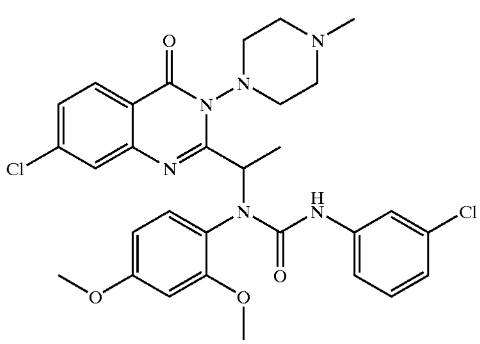 | 612 | 37.6 | 2-amino-4-chloro-benzoic acid, 3-chlorophenyl isocyanate |

TABLE 1-continued

| Cmpd | Structure | MS | RT (min) | Starting materials |
|---|---|---|---|---|
| 223 | 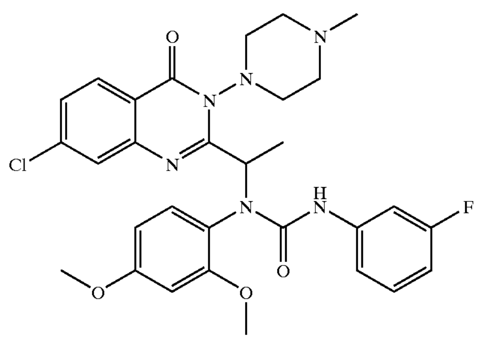 | 595 | 34.9 | 2-amino-4-chloro-benzoic acid, 3-fluorophenyl isocyanate |
| 224 | 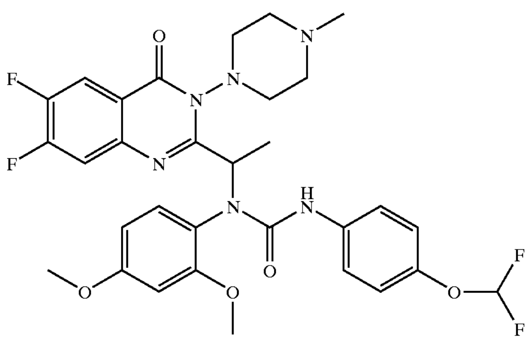 | 645 | 33.4 | 2-amino-4,5-difluoro-benzoic acid, 4-(difluoromethoxy)phenyl isocyanate |
| 225 | 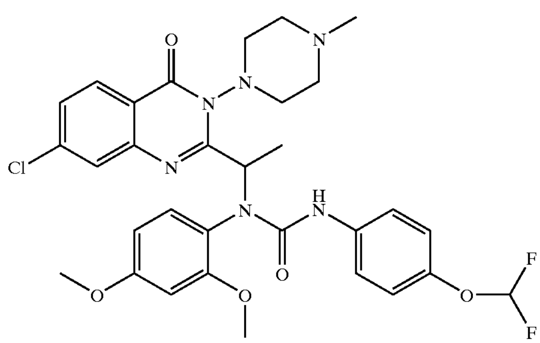 | 643/5 (M + H) | 34.7 | 2-amino-4-chloro-benzoic acid, 4-(difluoromethoxy)phenyl isocyanate |
| 226 | 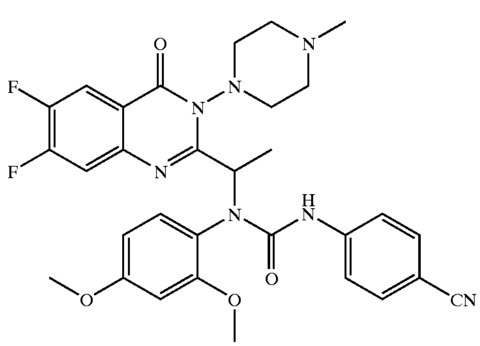 | 605 (M + H) | 31.6 | 2-amino-4,5-difluoro-benzoic acid |

TABLE 1-continued

| Cmpd | Structure | MS | RT (min) | Starting materials |
|---|---|---|---|---|
| 227 | 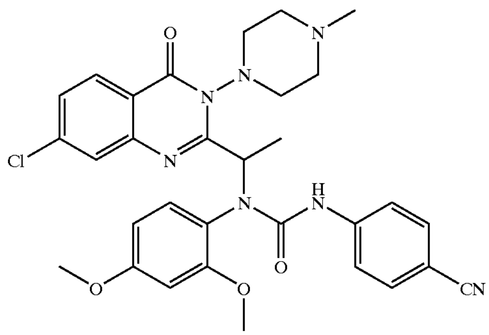 | 602/4 (M + H) | 33.3 | 2-amino-4-chloro-benzoic acid |
| 228 | 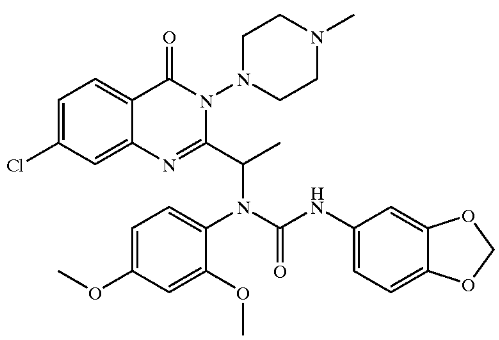 | 621/3 (M + H) | 31.1 | 2-amino-4-chloro-benzoic acid, 5-isocyanato-benzo[1,3]dioxole |

GM for Other Substituted Piperazines (Racemic)

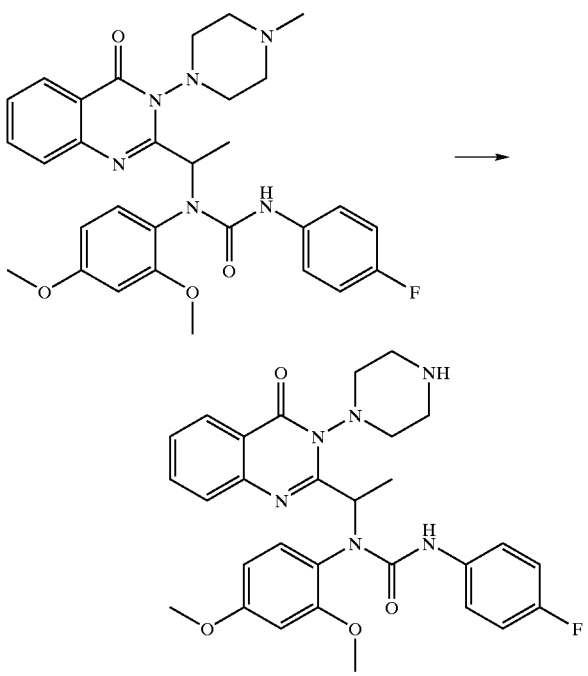

The appropriate N-methyl piperazine compound (1 eq) was dissolved in anhydrous toluene at about 0.1M, and α-chloroethyl chloroformate (2.5 eq) was added. Heating at 100° C. was continued until the reaction was complete (more chloroformate was added if needed, monitoring consumption of starting material by TLC). The solvent was removed in vacuo, and the crude chloroethyl carbamate was dissolved in methanol at a concentration of about 0.1M. Aqueous HCl (1N; 1/10 of the volume of methanol) was added and the solution was stirred at room temperature for 1 hour (monitoring by TLC). When no intermediate carbamate remained, the solvent was partially removed in vacuo. The residue was partitioned between ethyl acetate and dilute aq. NaOH (pH<8.5). The organic phase was washed with brine and dried over anhydrous sodium sulfate to give the free piperazine (MS 547 (M+H); RT 26.7 min).

The free piperazine was then reacted with the compounds shown in the last column of Table 2 to give the compounds indicated.

TABLE 2

| Cmpd | Structure | MS | RT (min) | Reagents, starting materials |
|------|-----------|----|----|------|
| 229 | 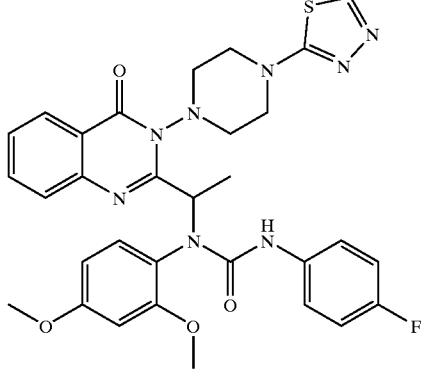 | 632 (M + H) | 33.0 | 4-fluorophenyl isocyanate; from free piperazine:<br>1. 1,1'-thiocarbonyldiimidazole, hydrazine, DMF, RT;<br>2. trimethylorthoformate, 90° C. |
| 230 | 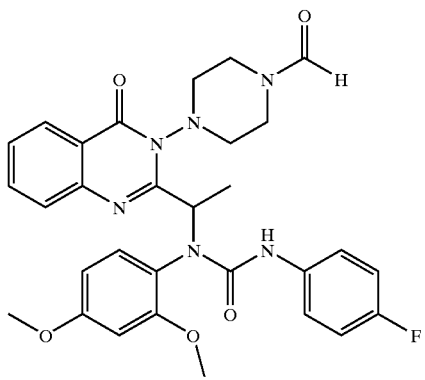 | 576 (M + H) | 30.7 | 4-fluorophenyl isocyanate; formic acid + acetic anhydride |
| 231 | 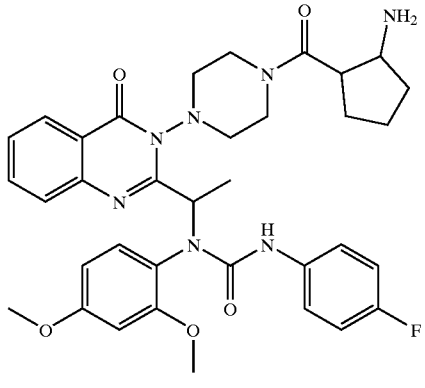 | 659 (M + H) | 27.1 | 4-fluorophenyl isocyanate; from free piperazine:<br>1. 2-(tert-butoxycarbonylamino)-1-cyclopentanecaboxylic acid, EDC, HOBT, DMF, RT;<br>2. TFA, dichloromethane |

TABLE 2-continued

| Cmpd | Structure | MS | RT (min) | Reagents, starting materials |
|---|---|---|---|---|
| 232 | 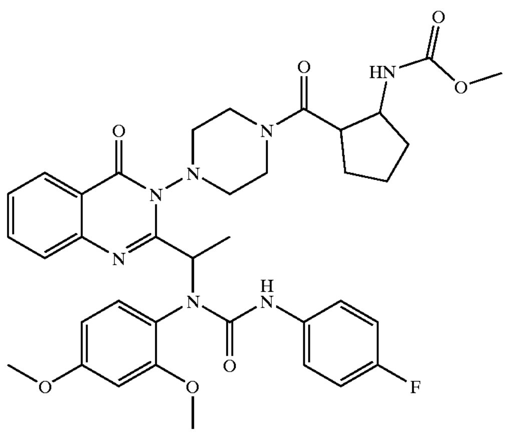 | 717 (M + H) | 34.8 | From compound with 231, acylating with methyl chloroformate |
| 233 | 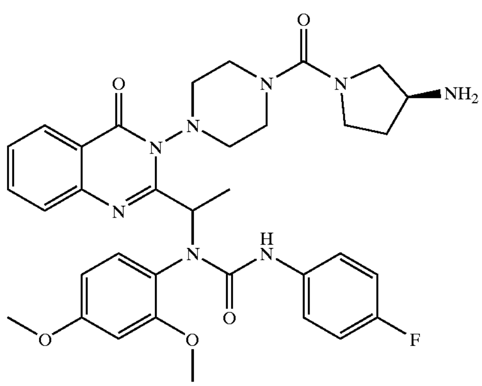 | 660 (M + H) | 24.7 | 4-fluorophenyl isocyanate; from free piperazine:<br>1. triphosgene, triethylamine, 1,2-dichloroethane, RT;<br>2. (S)-3-(t-butoxycarbonylamino)pyrrolidine;<br>3. TFA, dichloromethane |
| 234 | 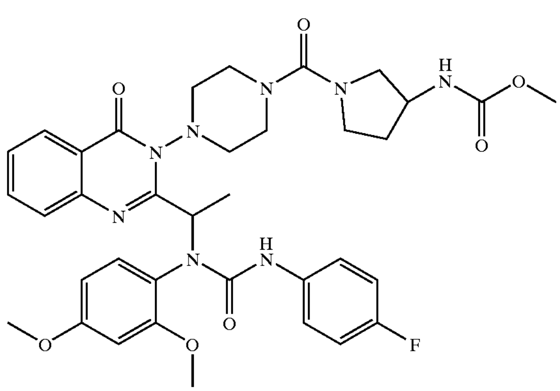 | 718 (M + H) | 31.3 | 4-fluorophenyl isocyanate; from free piperazine:<br>1. triphosgene, triethylamine, 1,2-dichloroethane, RT;<br>2. (3-(t-butoxycarbonylamino)pyrrolidine;<br>3. TFA, dichloromethane<br>4. Methyl chloroformate |

TABLE 2-continued

| Cmpd | Structure | MS | RT (min) | Reagents, starting materials |
|---|---|---|---|---|
| 235 | 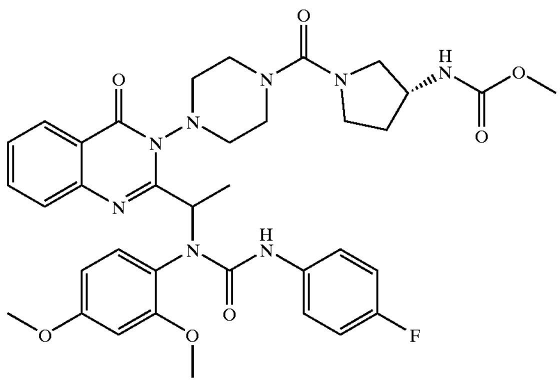 | 718 (M + H) | 31.2 | 4-fluorophenyl isocyanate; from free piperazine:<br>1. triphosgene, triethylamine, 1,2-dichloroethane, RT;<br>2. (R)-3-(t-butoxycarbonylamino)pyrrolidine;<br>3. TFA, dichloromethane<br>4. Methyl chloroformate |
| 236 | 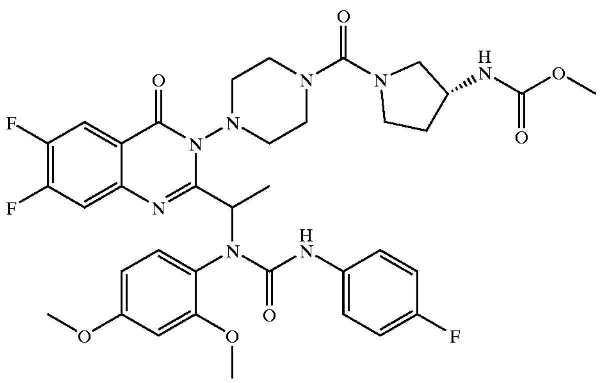 | 754 (M + H) | 34.0 | As compound 235, starting from 2-amino-4,5-difluorobenzoic acid |
| 237 | 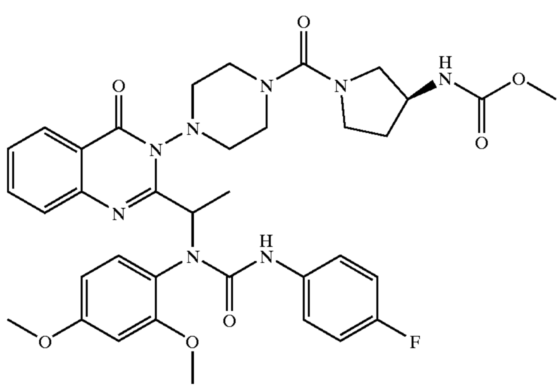 | 718 (M + H) | 31.2 | 4-fluorophenyl isocyanate; from free piperazine:<br>1. triphosgene, triethylamine, 1,2-dichloroethane, RT;<br>2. (S)-3-(t-butoxycarbonylamino)pyrrolidine;<br>3. TFA, dichloromethane<br>4. Methyl chloroformate |
| 238 | 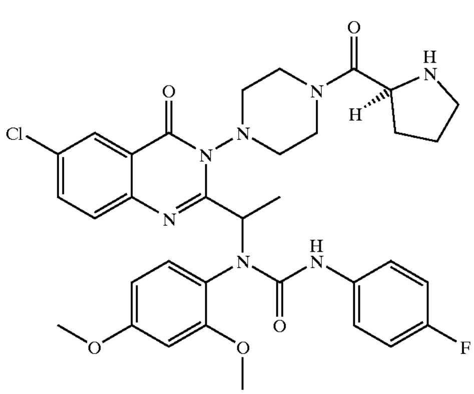 | 678/80 (M + H) | 28.9 | 2-amino-5-chloro-benzoic acid; 4-fluorophenyl isocyanate; from free piperazine:<br>1. BOC-L-proline N-hydroxysuccinimide ester;<br>2. 2.TFA |

TABLE 2-continued

| Cmpd | Structure | MS | RT (min) | Reagents, starting materials |
|---|---|---|---|---|
| 239 | 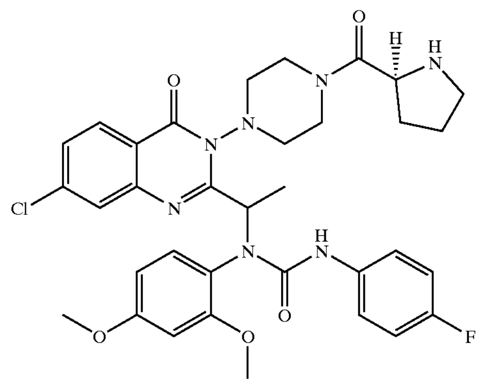 | 678/80 (M + H) | 29.5 | As compound 238, but starting from 2-amino-4-chloro-benzoic acid |
| 240 | 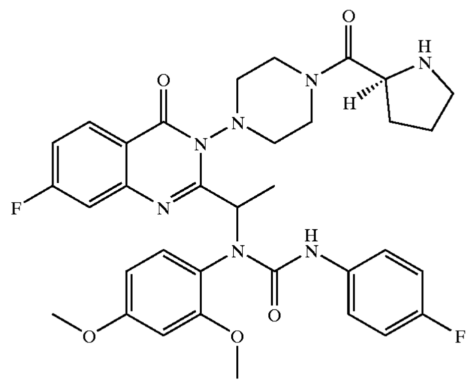 | 679 (M + H) | 29.5 | As compound 238, but starting from 2-amino-4-fluoro-benzoic acid |
| 241 | 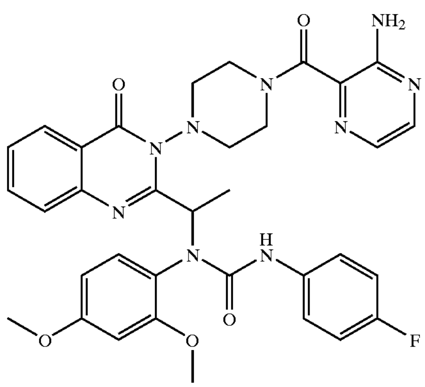 | 669 (M + H) | 31.5 | 4-fluorophenyl isocyanate; free piperazine acylated with 3-amino-pyrazine-2-carboxylic acid/EDC/DMF |
| 242 | 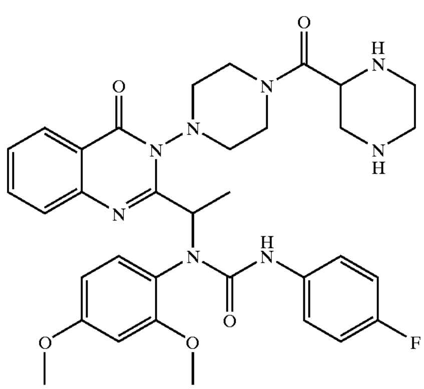 | 660 (M + H) | 24.5 | 4-fluorophenyl isocyanate; from free piperazine:<br>1. Piperazine-1,2,4-tricarboxylic acid, 1,4-di-tert-butyl ester, EDC, DMF<br>2. TFA/dichloromethane |

TABLE 2-continued

| Cmpd | Structure | MS | RT (min) | Reagents, starting materials |
|---|---|---|---|---|
| 243 | 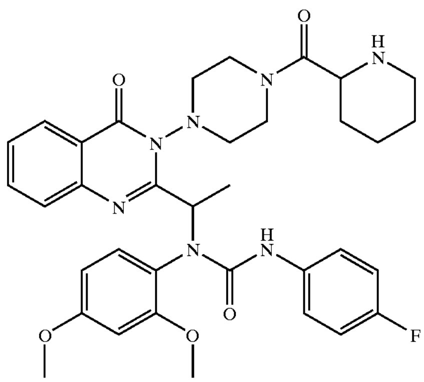 | 659 (M + H) | 26.5 | 4-fluorophenyl isocyanate; from free piperazine:<br>1. Piperidine-1,2-dicarboxylic acid 1-tert-butyl ester, EDC, DMF<br>2. TFA/dichloromethane |
| 244 | 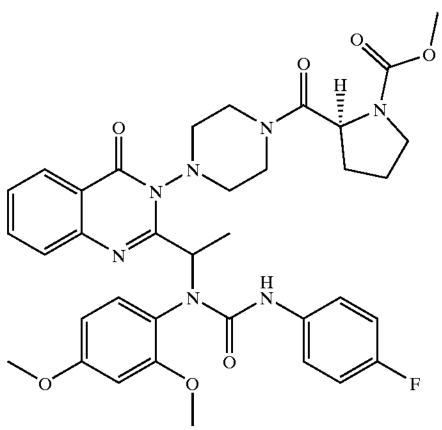 | 701 (M + H) | 32.2 | As compound 238, but starting from 2-aminobenzoic acid; pyrrolidine acylated with methyl chloroformate |
| 245 | 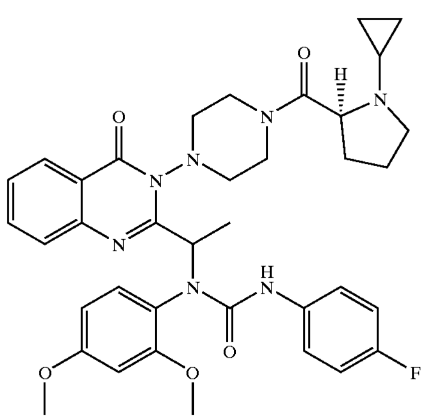 | 685 (M + H) | 33.3 | As compound 238, but starting from 2-aminobenzoic acid; pyrrolidine subjected to reductive amination with [(1-ethoxycyclopropyl) oxy]trimethylsilane and sodium cyanoborohydride |

TABLE 2-continued

| Cmpd | Structure | MS | RT (min) | Reagents, starting materials |
|---|---|---|---|---|
| 246 | 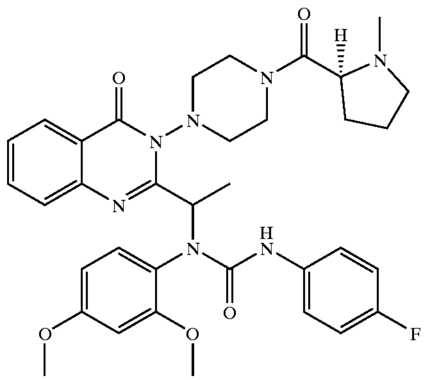 | 659 (M + H) | 27.0 | As compound 238, but starting from 2-aminobenzoic acid; pyrrolidine subjected to reductive amination with paraformaldehyde and sodium triacetoxyborohydride |
| 247 | 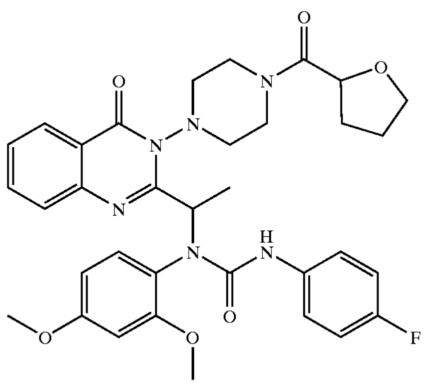 | 646 (M + H) | 32.4 | 4-fluorophenyl isocyanate; from free piperazine: tetrahydrofuran-2-carboxylic acid/EDC/DMF |
| 248 | 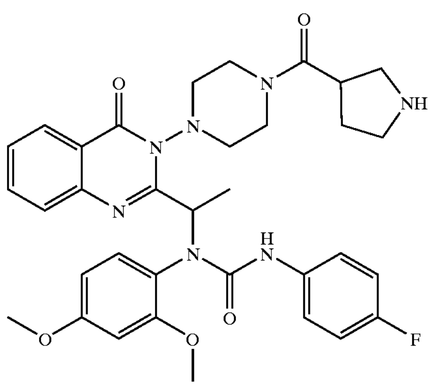 | 645 (M + H) | 25.4 | 4-fluorophenyl isocyanate; from free piperazine: Pyrrolidine-1,3-dicarboxylic acid 1-tert-butyl ester/EDC/DMF 3. TFA/dichloromethane |
| 249 | 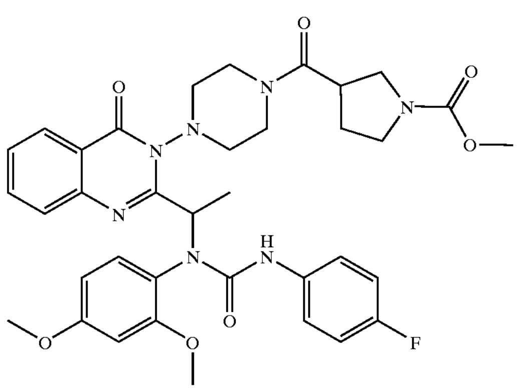 | 703 (M + H) | 32.5 | From compound 248; pyrrolidine acylated with methyl chloroformate |

TABLE 2-continued

| Cmpd | Structure | MS | RT (min) | Reagents, starting materials |
|---|---|---|---|---|
| 250 | 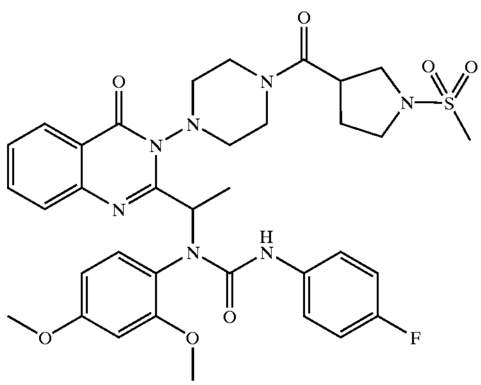 | 723 (M + H) | 32.6 | From compound 248; pyrrolidine acylated with methane sulfonyl chloride/tiethylamine/dichloromethane |
| 251 | 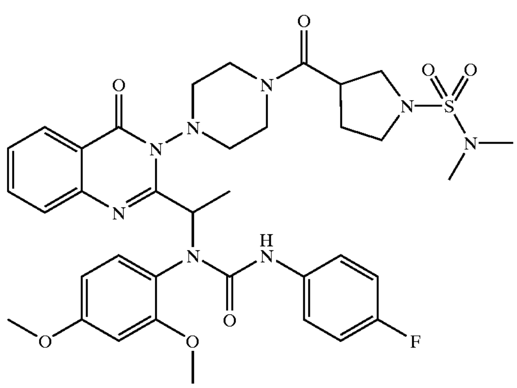 | 752 (M + H) | 34.6 | From compound 248; pyrrolidine acylated with dimethylsulfamoyl chloride/triethylamine/dichloromethane |
| 252 | 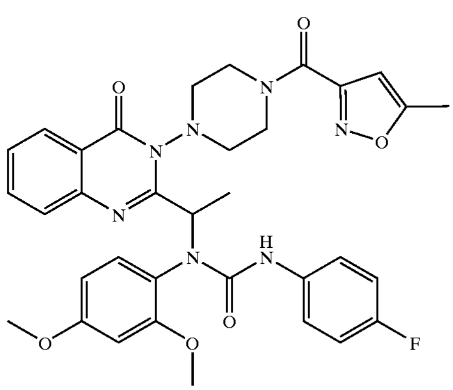 | 657 (M + H) | 36.0 | 4-fluorophenyl isocyanate; free piperazine acylated with 5-methyl-isoxazole-3-carboxylic acid/EDC/DMF |
| 253 | 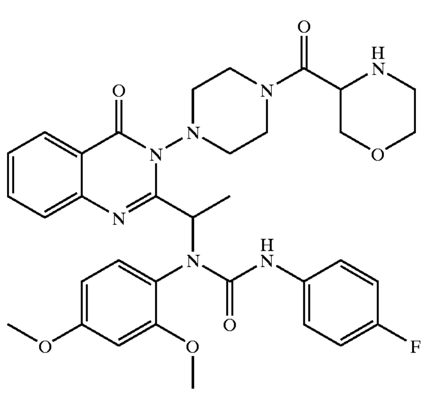 | 661 (M + H) | 27.6 | 4-fluorophenyl isocyanate; from free piperazine: 1. Morpholine-3,4-dicarboxylic acid 4-tert-butyl ester/EDC/DMF 2 TFA/dichloromethane |

TABLE 2-continued

| Cmpd | Structure | MS | RT (min) | Reagents, starting materials |
|---|---|---|---|---|
| 254 | 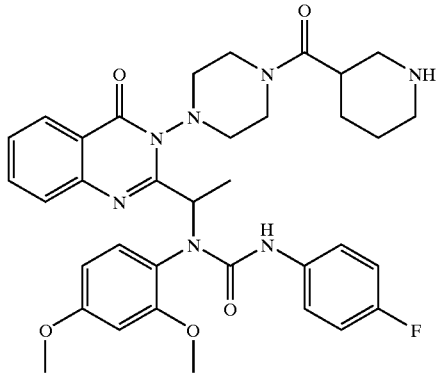 | 659 (M + H) | 26.0 | 4-fluorophenyl isocyanate; from free piperazine:<br>1. Piperidine-1,3-carboxylic acid 1-tert-butyl ester/EDC/DMF<br>2. TFA/dichloromethane |
| 255 | 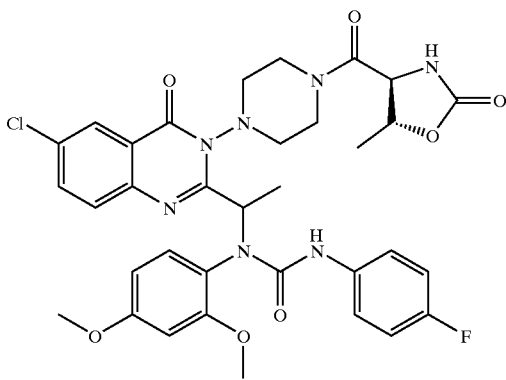 | 708/10 (M + H) | 33.4 | 2-amino-5-chloro-benzoic acid, 4-fluorophenyl isocyanate; from free piperazine:<br>1. N-(t-BOC) threonine/EDC/HOBT/DMF<br>2. TFA/dichloromethane<br>3. 1'1-carbonyldiimidazole/THF |
| 256 | 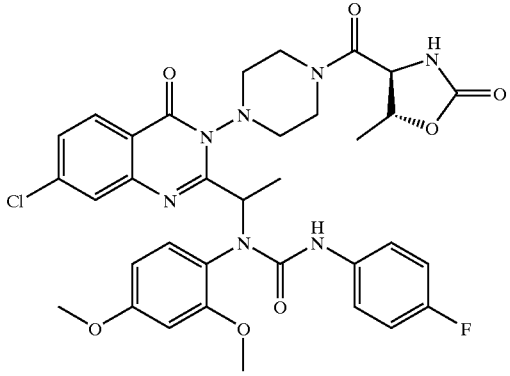 | 708/10 (M + H) | 33.9 | As compound 255, but starting from 2-amino-4-chloro-benzoic acid |
| 257 | 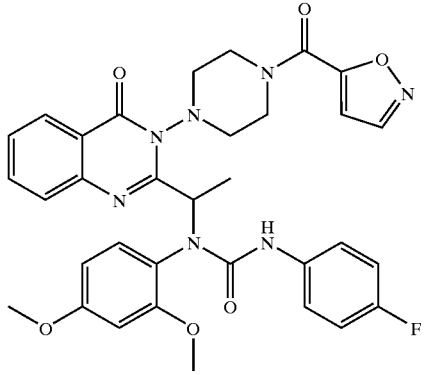 | 643 (M + H) | 34.2 | 4-fluorophenyl isocyanate; free piperazine acylated with isoxazole-5-carboxylic acid/EDC/DMF |

TABLE 2-continued

| Cmpd | Structure | MS | RT (min) | Reagents, starting materials |
|---|---|---|---|---|
| 258 | 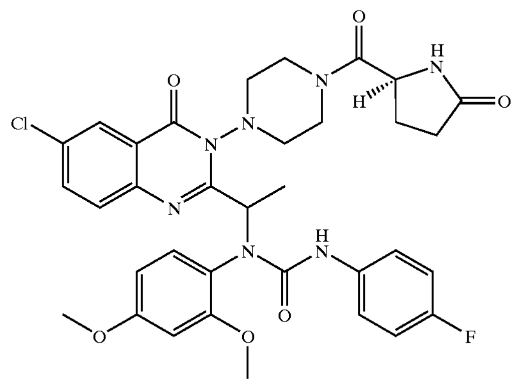 | 692/4 (M + H) | 30.7 | 2-amino-5-chloro-benzoic acid, 4-fluorophenyl isocyanate; free piperazine acylated with L-pyroglutamic acid/EDC/HOBT/DMF |
| 259 | 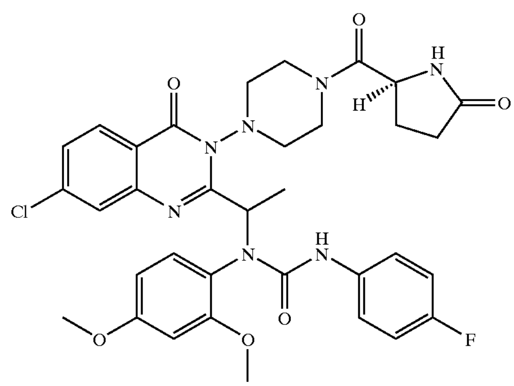 | 692/4 (M + H) | 31.4 | As compound 258, but starting from 2-amino-4-chloro-benzoic acid |
| 260 | 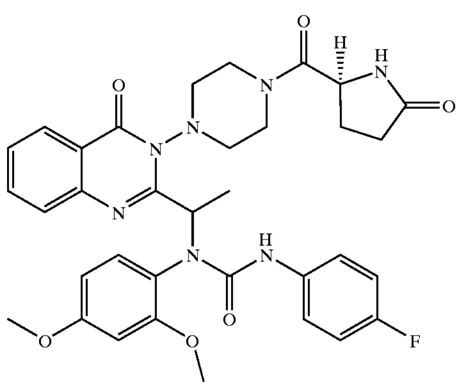 | 659 (M + H) | 27.7 | 4-fluorophenylisocyanate; free piperazine acylated with L-pyroglutamic acid/EDC/HOBT/DMF |
| 261 | 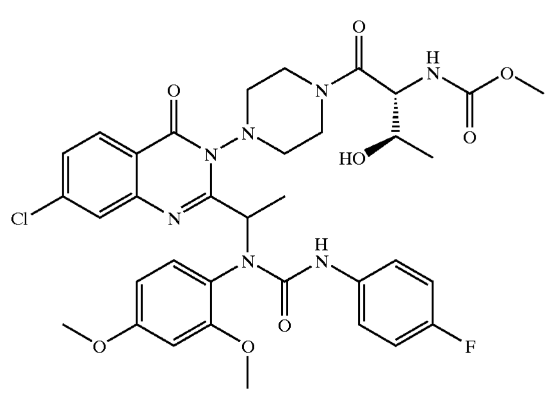 | 748/50 (M + H) | 33.8 | 2-amino-4-chloro-benzoic acid, 4-fluorophenyl isocyanate; from free piperazine: 4. N-(t-BOC)threonine/EDC/DMF 5. TFA/dichloromethane 6. Methyl chloroformate |

TABLE 2-continued

| Cmpd | Structure | MS | RT (min) | Reagents, starting materials |
|---|---|---|---|---|
| 262 | 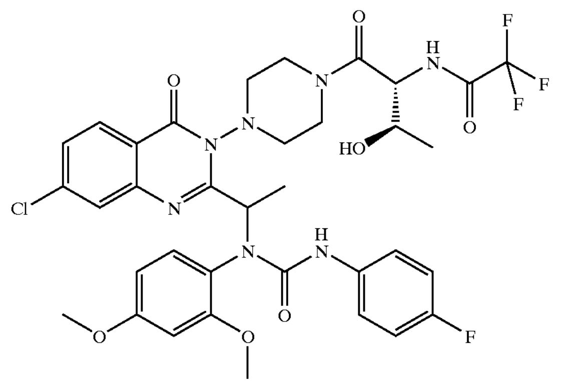 | 778/80 (M + H) | 37.6 | 2-amino-4-chloro-benzoic acid, 4-fluorophenyl isocyanate; from free piperazine:<br>1. N-(t-BOC)threonine/EDC/DMF<br>2. TFA/dichloromethane<br>3. Trifluoroacetic anhydride |
| 263 | 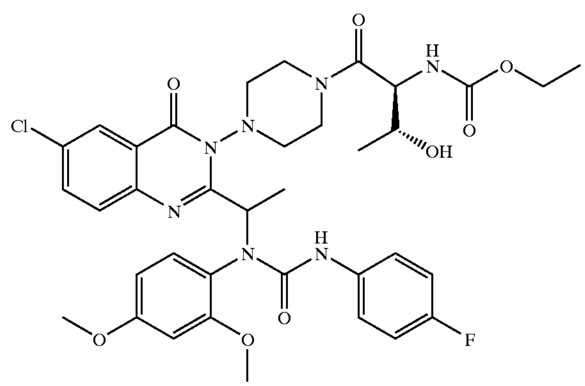 | 754/6 (M + H) | 34.6 | 2-amino-5-chloro-benzoic acid, 4-fluorophenyl isocyanate; from free piperazine:<br>1. N-(t-BOC)threonine/EDC/DMF<br>2. TFA/dichloromethane<br>3. Ethyl chloroformate |
| 264 | 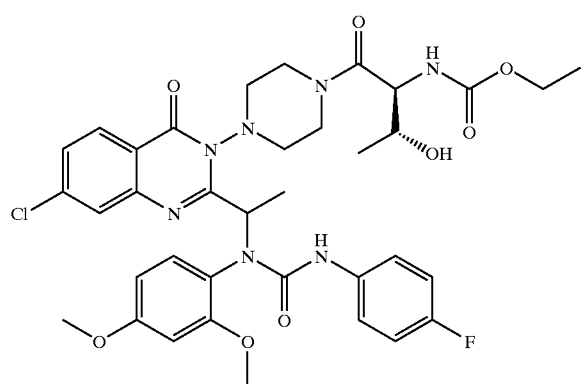 | 754/6 (M + H) | 35.2 | 2-amino-4-chloro-benzoic acid, 4-fluorophenyl isocyanate; from free piperazine:<br>1. N-(t-BOC)threonine/EDC/DMF<br>2. TFA/dichloromethane<br>3. Ethyl chloroformate |
| 265 | 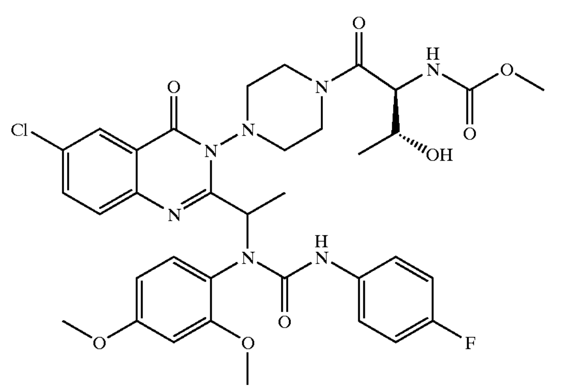 | 740/2 (M + H) | 33.0 | 2-amino-5-chloro-benzoic acid, 4-fluorophenyl isocyanate; from free piperazine:<br>1. N-(t-BOC)threonine/EDC/DMF<br>2. TFA/dichloromethane<br>3. Methyl chloroformate |

TABLE 2-continued

| Cmpd | Structure | MS | RT (min) | Reagents, starting materials |
|---|---|---|---|---|
| 266 | 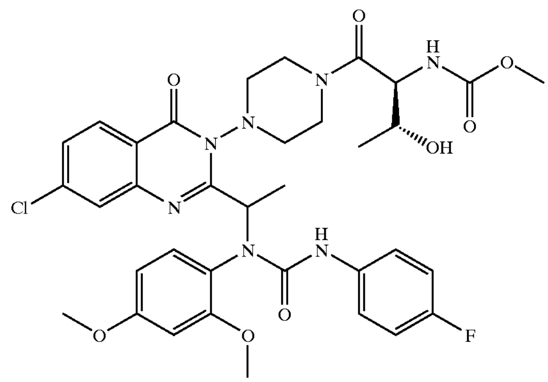 | 740/2 (M + H) | 33.6 | 2-amino-4-chloro-benzoic acid, 4-fluorophenyl isocyanate; from free piperazine: 1. N-(t-BOC)threonine/EDC/DMF 2. TFA/dichloromethane 3. Methyl chloroformate |
| 267 | 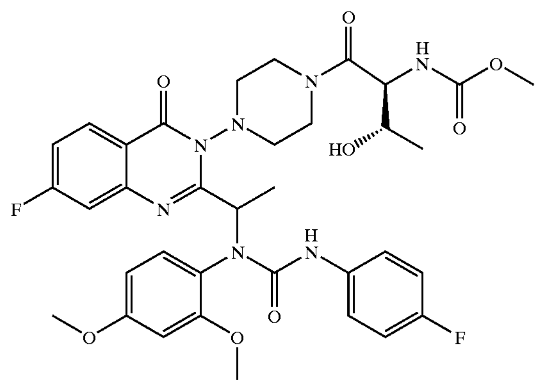 | 725 (M + H) | 31.0 | 2-amino-4-chloro-benzoic acid, 4-fluorophenyl isocyanate; from free piperazine: 1. N-(t-BOC)threonine/EDC/DMF 2. TFA/dichloromethane 3. Methyl chloroformate |
| 268 | 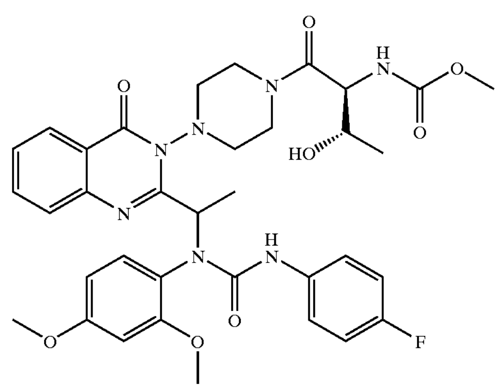 | 705 (M + H) | 29.7 | 4-fluorophenyl isocyanate; from free piperazine: 1. N-(t-BOC)threonine/EDC/DMF 2. TFA/dichloromethane 3. Methyl chloroformate |
| 269 | 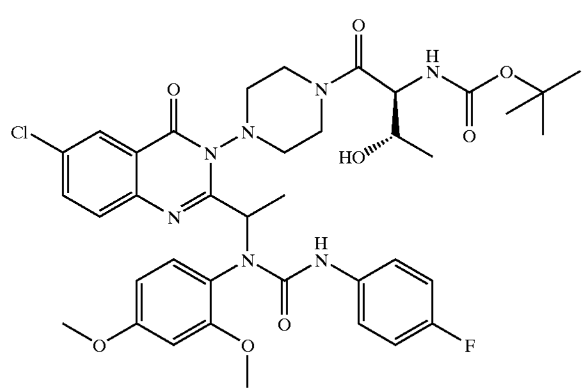 | 782/4 (M + H) | 38.2 | 2-amino-5-chloro-benzoic acid, 4-fluorophenyl isocyanate; from free piperazine: N-(t-BOC)-threonine/EDC/DMF |

TABLE 2-continued

| Cmpd | Structure | MS | RT (min) | Reagents, starting materials |
|---|---|---|---|---|
| 270 | 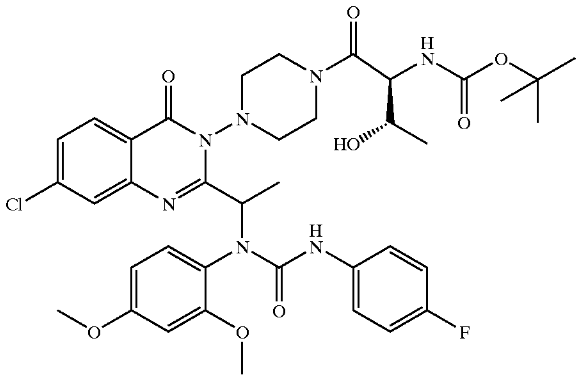 | 782/4 (M + H) | 38.6 | 2-amino-4-chloro-benzoic acid, 4-fluorophenyl isocyanate; from free piperazine: N-(t-BOC)-threonine/EDC/DMF |
| 271 | 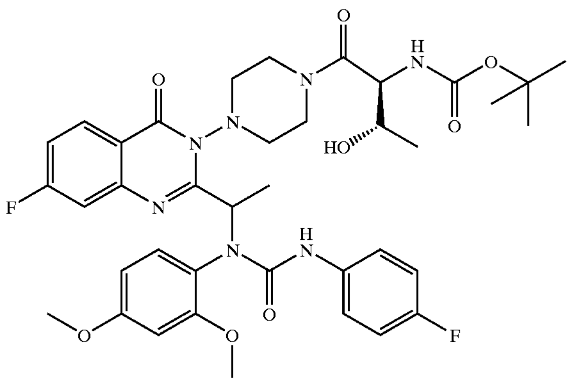 | 765 (M + H) | 36.0 | 2-amino-4-chloro-benzoic acid, 4-fluorophenyl isocyanate; from free piperazine: N-(t-BOC)-threonine/EDC/DMF |
| 272 | 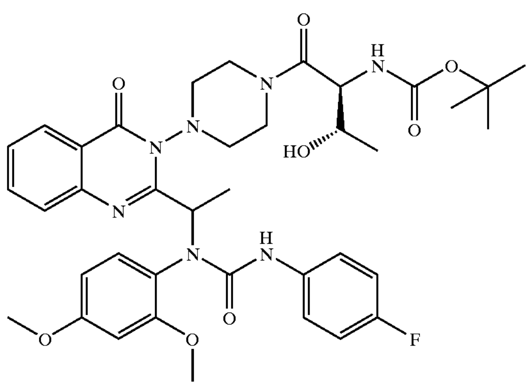 | 749 (M + H) | 35.0 | 4-fluorophenyl isocyanate; from free piperazine: N-(t-BOC)-threonine/EDC/DMF |
| 273 | 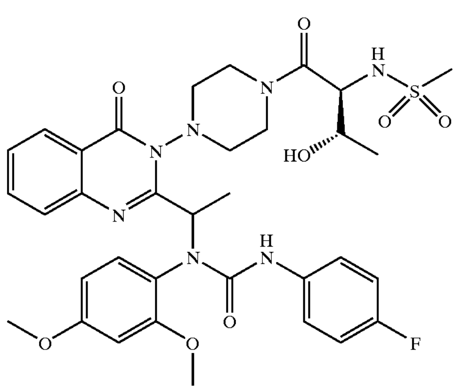 | 727 (M + H) | 29.5 | 4-fluorophenyl isocyanate; from free piperazine: 1. N-(t-BOC)-threonine/EDC/DMF 2. TFA/dichloromethane 3. Methanesulfonyl chloride/ triethylamine/dichloromethane |

TABLE 2-continued

| Cmpd | Structure | MS | RT (min) | Reagents, starting materials |
|---|---|---|---|---|
| 274 | 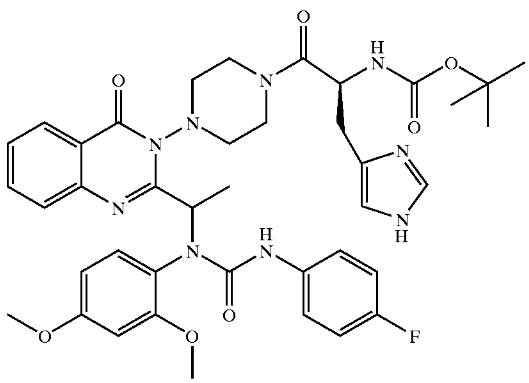 | 785 (M + H) | 31.0 | 4-fluorophenyl isocyanate; from free piperazine: N-(t-BOC)-histidine/EDC/DMF |
| 275 | 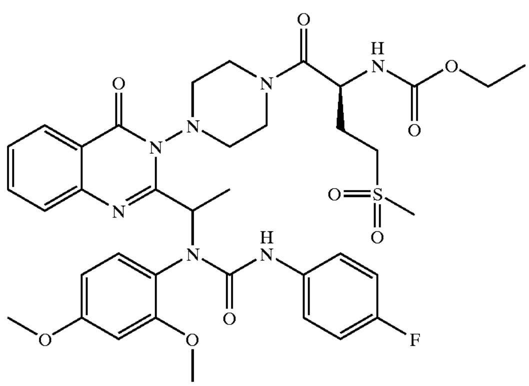 | 783 (M + H) | 32.0 | 4-fluorophenyl isocyanate; from free piperazine: 1. 2-tert-Butoxycarbonylamino-4-methanesulfonyl-butyric acid/EDC/DMF 2. TFA/dichloromethane 3. Ethyl chloroformate |
| 276 | 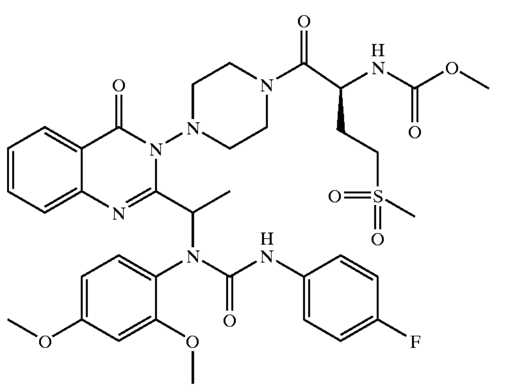 | 769 (M + H) | 30.6 | 4-fluorophenyl isocyanate; from free piperazine: 1. 2-tert-Butoxycarbonylamino-4-methanesulfonyl-butyric acid/EDC/DMF 2. TFA/dichloromethane 3. Methyl chloroformate |
| 277 | 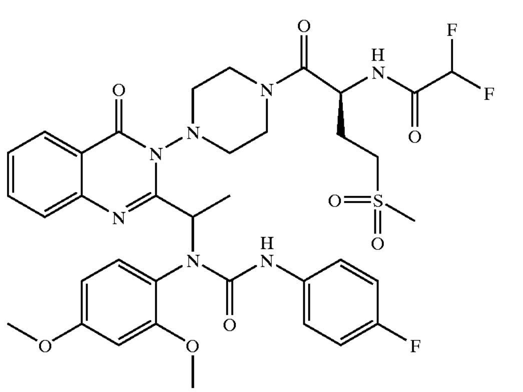 | 789 (M + H) | 31.9 | 4-fluorophenyl isocyanate; from free piperazine: 1. 2-tert-Butoxycarbonylamino-4-methanesulfonyl-butyric acid/EDC/DMF 2. TFA/dichloromethane 3. Methyl chloroformate, difluoroacetic acid, triethylamine, dichloromethane |

TABLE 2-continued

| Cmpd | Structure | MS | RT (min) | Reagents, starting materials |
|---|---|---|---|---|
| 278 | 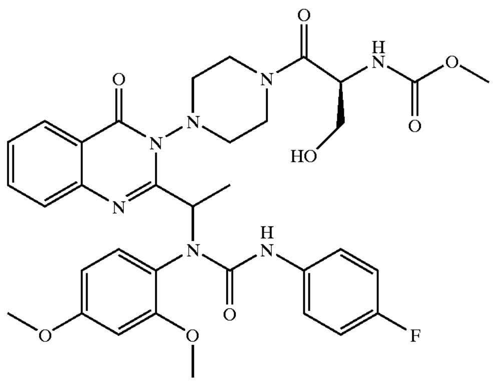 | 693 (M + H) | 28.8 | 4-fluorophenyl isocyanate; from free piperazine:<br>1. N-(t-BOC)-serine/EDC/DMF<br>2. TFA/dichloromethane<br>3. Methyl chloroformate |
| 279 | 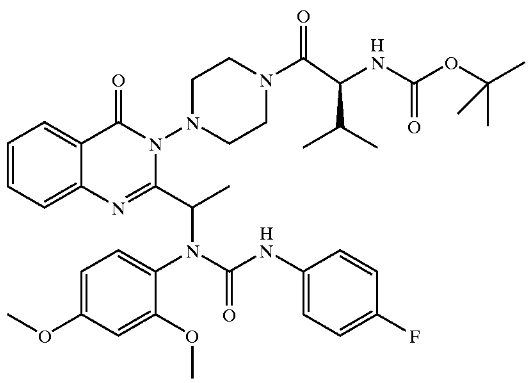 | 747 (M + H) | 40.7 | 4-fluorophenyl isocyanate; from free piperazine:<br>N-(t-BOC)-valine/EDC/DMF |
| 280 | 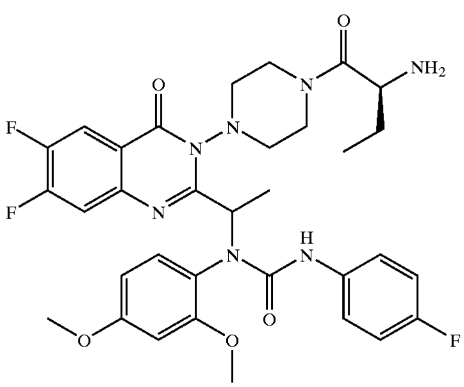 | 669 (M + H) | 28.5 | 2-amino-4,5-difluorobenzoic acid; 4-fluorophenyl isocyanate; from free piperazine:<br>1. (S)-2-tert-Butoxycarbonylamino-butyric acid/EDC/DMF<br>2. TFA/dichloromethane |
| 281 | 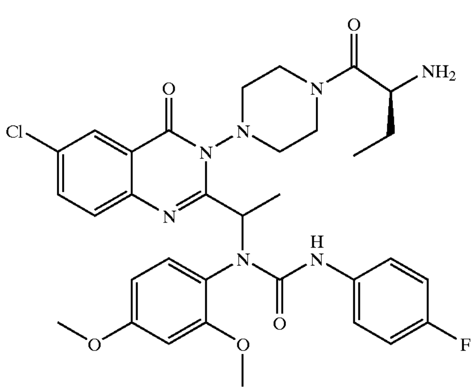 | 666/8 (M + H) | 29.0 | 2-amino-5-chlorobenzoic acid; 4-fluorophenyl isocyanate; from free piperazine:<br>1. (S)-2-tert-Butoxycarbonylamino-butyric acid/EDC/DMF<br>2. TFA/dichloromethane |

TABLE 2-continued

| Cmpd | Structure | MS | RT (min) | Reagents, starting materials |
|---|---|---|---|---|
| 282 | 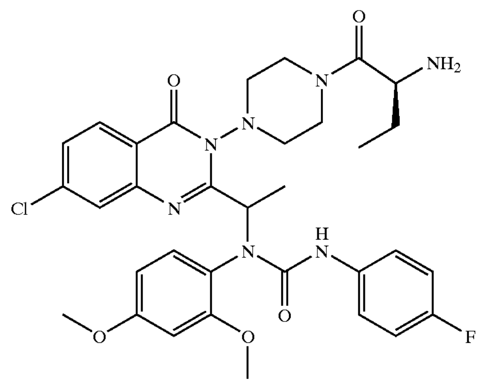 | 666/8 (M + H) | 29.5 | 2-amino-4-chlorobenzoic acid; 4-fluorophenyl isocyanate; from free piperazine: 1. (S)-2-tert-Butoxycarbonylamino-butyric acid/EDC/DMF 2. TFA/dichloromethane |
| 283 | 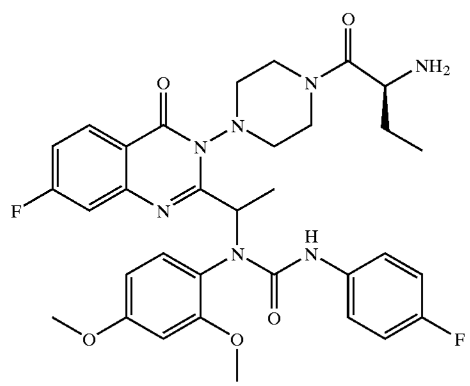 | 651 (M + H) | 27.4 | 2-amino-4-fluorobenzoic acid; 4-fluorophenyl isocyanate; from free piperazine: 1. (S)-2-tert-Butoxycarbonylamino-butyric acid/EDC/DMF 2. TFA/dichloromethane |
| 284 | 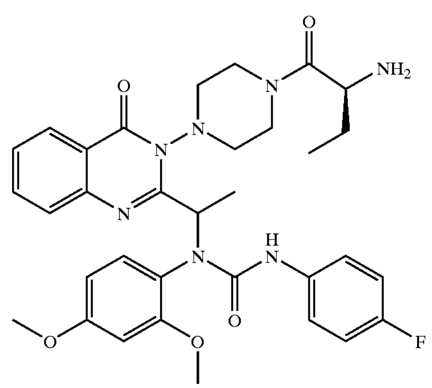 | 633 (M + H) | 25.9 | 4-fluorophenyl isocyanate; from free piperazine: 1. (S)-2-tert-Butoxycarbonylamino-butyric acid/EDC/DMF 2. TFA/dichloromethane |
| 285 | 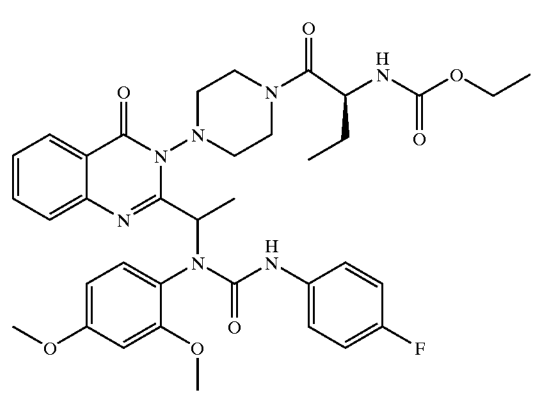 | 705 (M + H) | 35.2 | 4-fluorophenyl isocyanate; from free piperazine: 1. (S)-2-tert-Butoxycarbonylamino-butyric acid/EDC/DMF 2. TFA/dichloromethane 3. Ethyl chloroformate |

TABLE 2-continued

| Cmpd | Structure | MS | RT (min) | Reagents, starting materials |
|---|---|---|---|---|
| 286 | 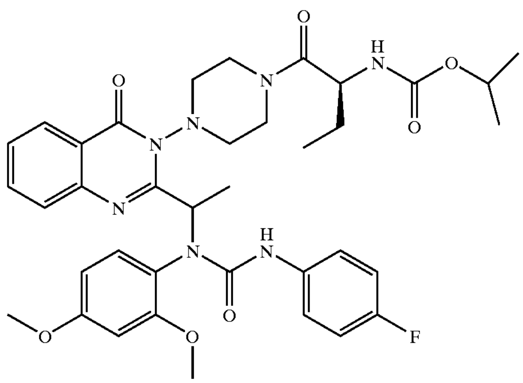 | 719 (M + H) | 36.7 | 4-fluorophenyl isocyanate; from free piperazine:<br>1. (S)-2-tert-Butoxycarbonylamino-butyric acid/EDC/DMF<br>2. TFA/dichloromethane<br>3. Isopropyl chloroformate |
| 287 | 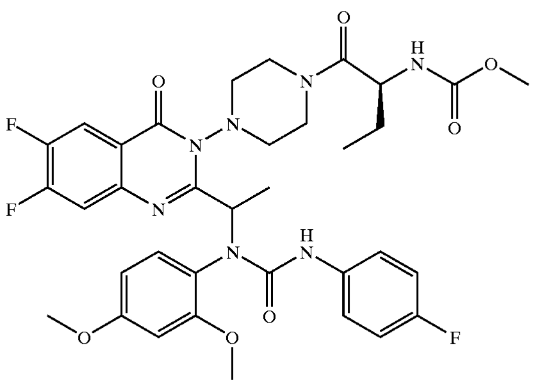 | 727 (M + H) | 36.1 | 2-amino-4,5-difluorobenzoic acid; 4-fluorophenyl isocyanate; from free piperazine:<br>1. 2-tert-Butoxycarbonylamino-butyric acid/EDC/DMF<br>2. TFA/dichloromethane<br>3. Methyl chloroformate |
| 288 | 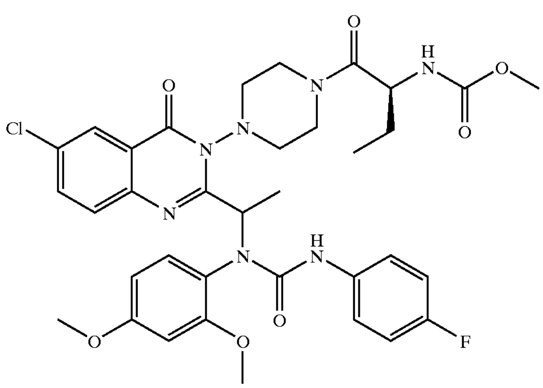 | 724/6 (M + H) | 36.9 | 2-amino-5-chlorobenzoic acid; 4-fluorophenyl isocyanate; from free piperazine:<br>1. (S)-2-tert-Butoxycarbonylamino-butyric acid/EDC/DMF<br>2. TFA/dichloromethane<br>3. Methyl chloroformate |
| 289 | 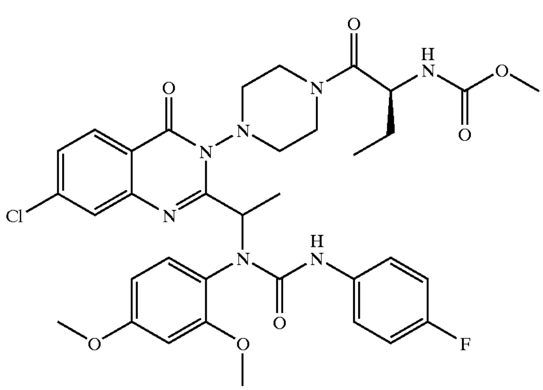 | 724/6 (M + H) | 37.4 | 2-amino-4-chlorobenzoic acid; 4-fluorophenyl isocyanate; from free piperazine:<br>1. (S)-2-tert-Butoxycarbonylamino-butyric acid/EDC/DMF<br>2. TFA/dichloromethane<br>3. Methyl chloroformate |

TABLE 2-continued

| Cmpd | Structure | MS | RT (min) | Reagents, starting materials |
|---|---|---|---|---|
| 290 | 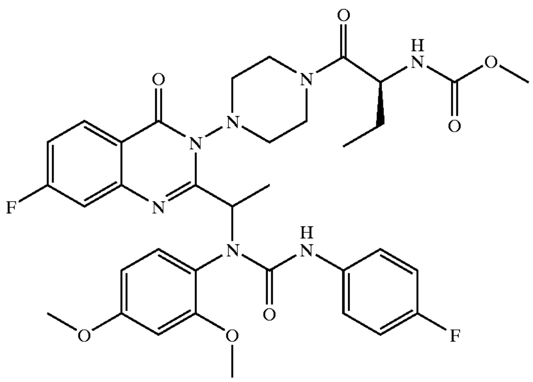 | 709 (M + H) | 35.1 | 2-amino-4-fluorobenzoic acid; 4-fluorophenyl isocyanate; from free piperazine:<br>1. (S)-2-tert-Butoxycarbonylamino-butyric acid/EDC/DMF<br>2. TFA/dichloromethane<br>3. Methyl chloroformate |
| 291 | 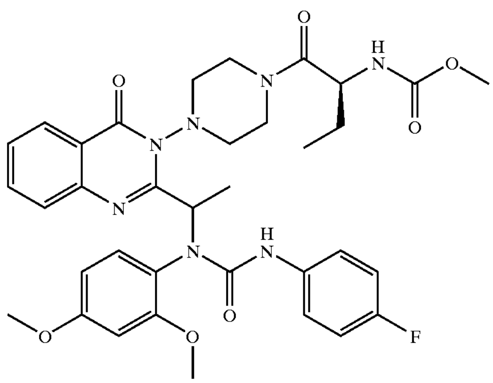 | 691 (M + H) | 33.4 | 4-fluorophenyl isocyanate; from free piperazine:<br>1. (S)-2-tert-Butoxycarbonylamino-butyric acid/EDC/DMF<br>2. TFA/dichloromethane<br>3. Methyl chloroformate |
| 292 | 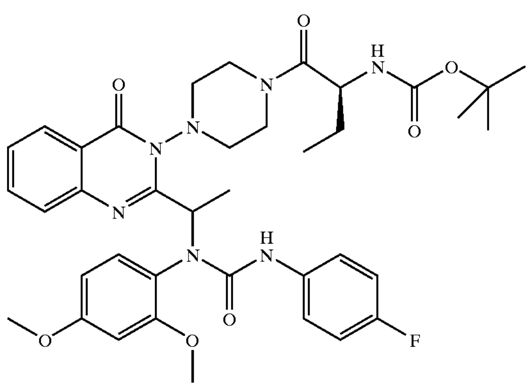 | 733 (M + H) | 38.8 | 4-fluorophenyl isocyanate; from free piperazine:<br>(S)-2-tert-Butoxycarbonylamino-butyric acid/EDC/DMF |
| 293 | 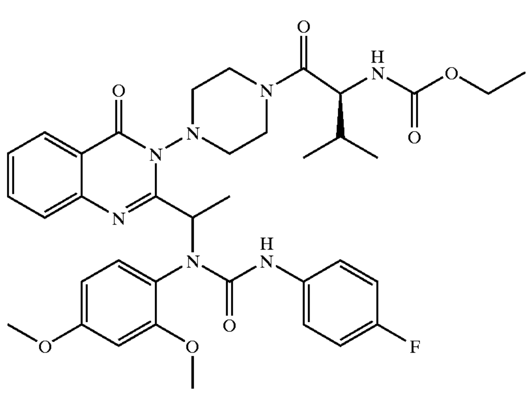 | 719 (M + H) | 37.0 | 4-fluorophenyl isocyanate; from free piperazine:<br>1. N-(t-BOC)-valine/EDC/DMF<br>2. TFA/dichloromethane<br>3. Ethyl chloroformate |

TABLE 2-continued

| Cmpd | Structure | MS | RT (min) | Reagents, starting materials |
|---|---|---|---|---|
| 294 | 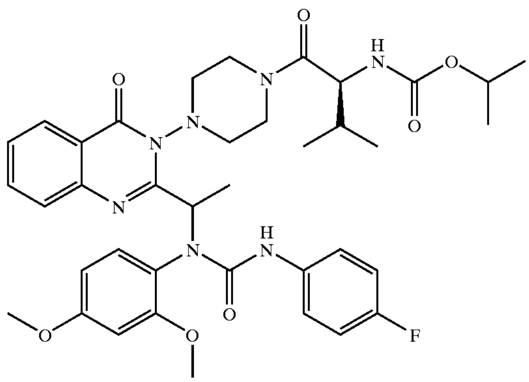 | 733 (M + H) | 38.3 | 4-fluorophenyl isocyanate; from free piperazine:<br>1. N-(t-BOC)-valine/EDC/DMF<br>2. TFA/dichloromethane<br>3. Isopropyl chloroformate |
| 295 | 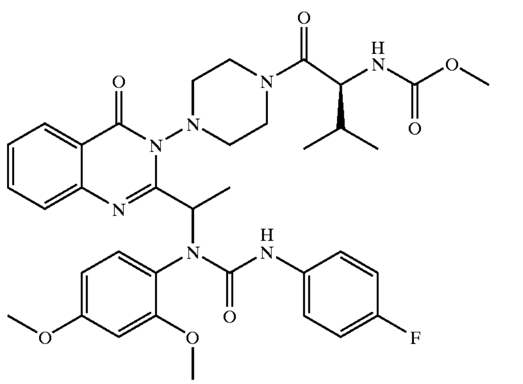 | 705 (M + H) | 34.8 | 4-fluorophenyl isocyanate; from free piperazine:<br>1. N-(t-BOC)-valine/EDC/DMF<br>2. TFA/dichloromethane<br>3. Methyl chloroformate |
| 296 | 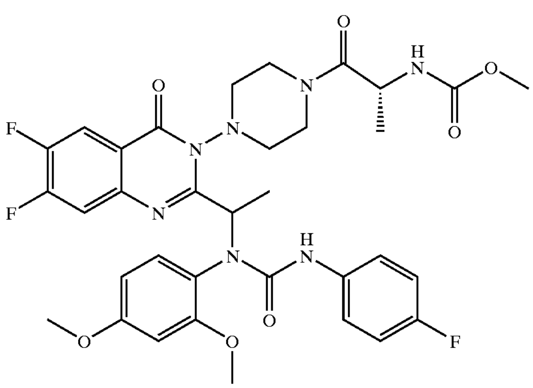 | 713 (M + H) | 34.9 | 2-amino-4,5-difluorobenzoic acid; 4-fluorophenyl isocyanate; from free piperazine:<br>1. N-(t-BOC)-(D)-alanine/EDC/DMF<br>2. TFA/dichloromethane<br>3. Methyl chloroformate |
| 297 | 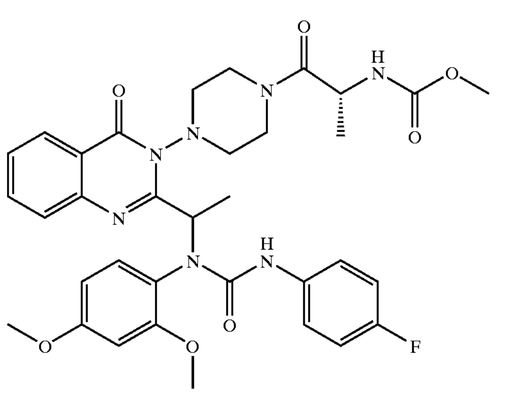 | 677 (M + H) | 32.1 | 4-fluorophenyl isocyanate; from free piperazine:<br>1. N-(t-BOC)-(D)-alanine/EDC/DMF<br>2. TFA/dichloromethane<br>3. Methyl chloroformate |

TABLE 2-continued

| Cmpd | Structure | MS | RT (min) | Reagents, starting materials |
|---|---|---|---|---|
| 298 | 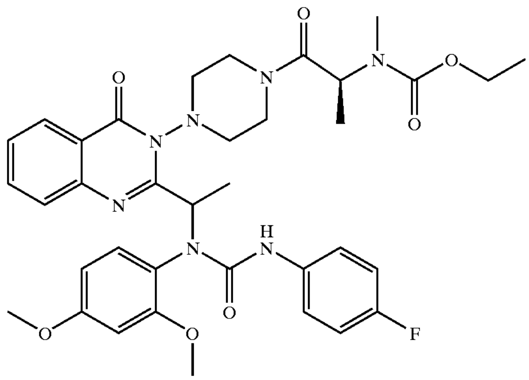 | 705 (M + H) | 36.7 | 4-fluorophenyl isocyanate; from free piperazine:<br>1. N-(t-BOC)-N-methyl-alanine/ EDC/DMF<br>2. TFA/dichloromethane<br>3. Ethyl chloroformate |
| 299 | 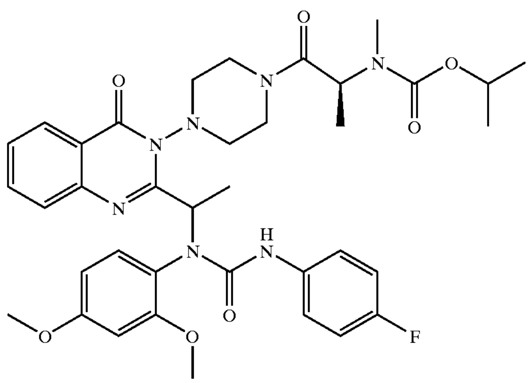 | 719 (M + H) | 37.1 | 4-fluorophenyl isocyanate; from free piperazine:<br>1. N-(t-BOC)-N-methyl-alanine/ EDC/DMF<br>2. TFA/dichloromethane<br>3. Isopropyl chloroformate |
| 300 | 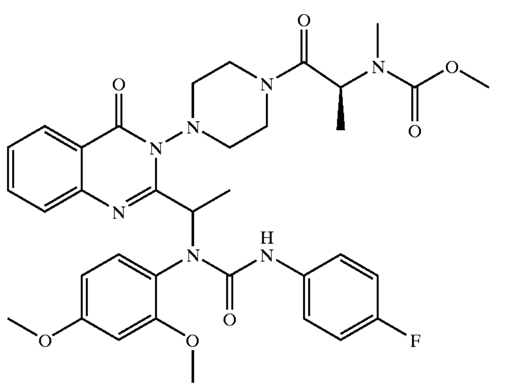 | 691 (M + H) | 33.9 | 4-fluorophenyl isocyanate; from free piperazine:<br>1. N-(t-BOC)-N-methyl-alanine/ EDC/DMF<br>2. TFA/dichloromethane<br>3. Methyl chloroformate |
| 301 | 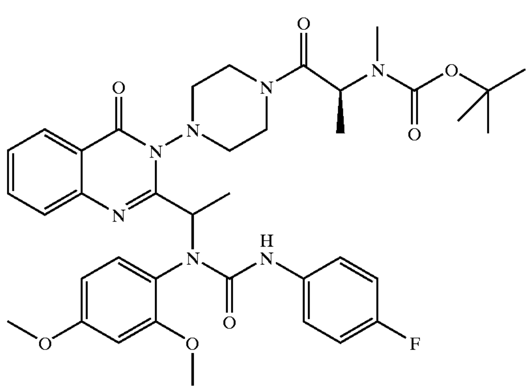 | 733 (M + H) | 39.0 | 4-fluorophenyl isocyanate; free piperazine acylated with N-(t-BOC)-N-methyl alanine/EDC/DMF |

TABLE 2-continued

| Cmpd | Structure | MS | RT (min) | Reagents, starting materials |
|---|---|---|---|---|
| 302 | 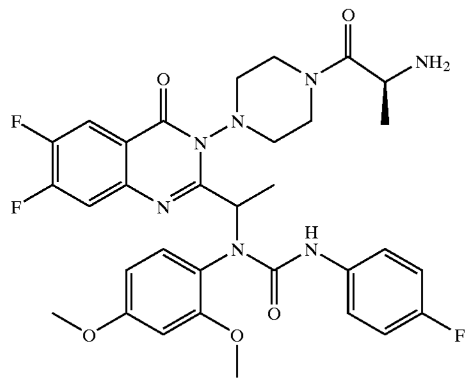 | 655 (M + H) | 27.7 | 2-amino-4,5-difluorobenzoic acid; 4-fluorophenyl isocyanate; from free piperazine: 1. N-(t-BOC)-alanine/EDC/DMF 2. TFA/dichloromethane |
| 303 | 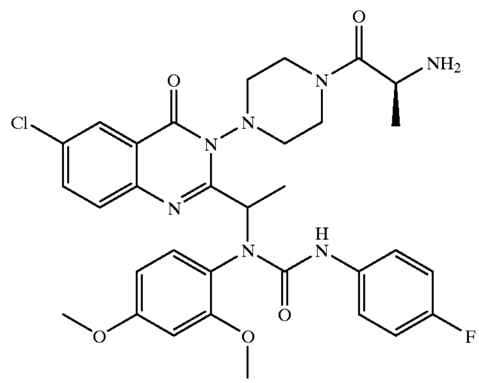 | 652/4 (M + H) | 27.9 | As compound 302, but starting from 2-amino-5-chlorobenzoic acid |
| 304 | 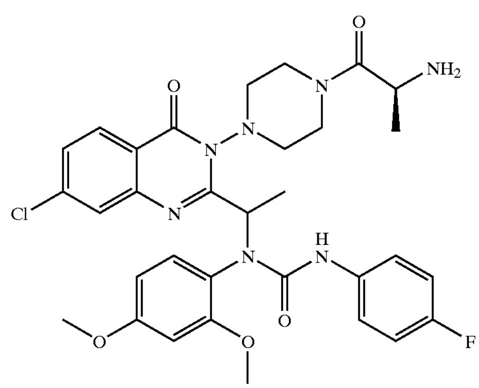 | 652/4 (M + H) | 28.4 | As compound 302, but starting from 2-amino-4-chlorobenzoic acid |
| 305 | 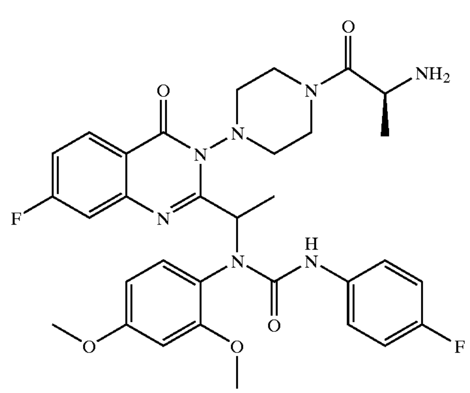 | 637 (M + H) | 26.3 | As compound 302, but starting from 2-amino-4-fluorobenzoic acid |

TABLE 2-continued

| Cmpd | Structure | MS | RT (min) | Reagents, starting materials |
|---|---|---|---|---|
| 306 | 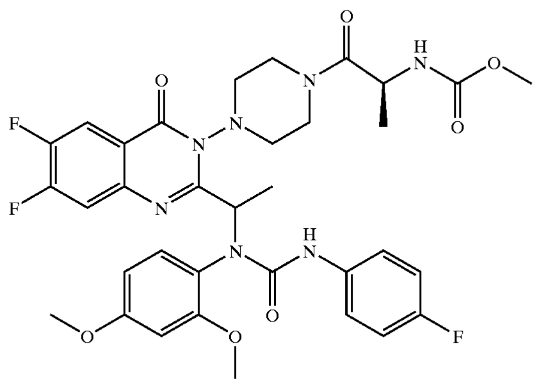 | 713 (M + H) | 34.8 | As compound 302, but using the (L)-alanine derived reagent |
| 307 | 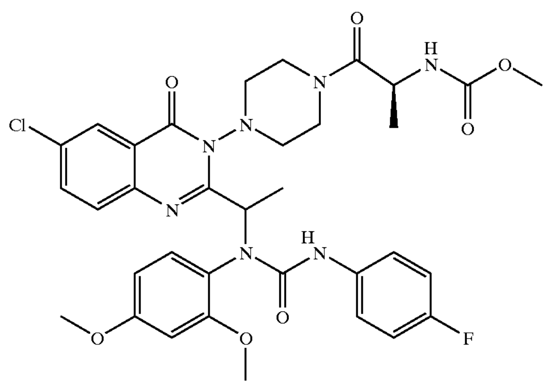 | 710/2 (M + H) | 35.6 | As compound 306, but starting from 2-amino-5-chlorobenzoic acid |
| 308 | 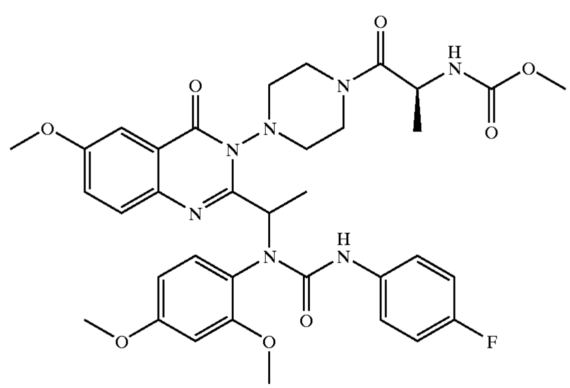 | 707 (M + H) | 32.6 | As compound 306, but starting from 2-amino-5-methoxybenzoic acid |
| 309 | 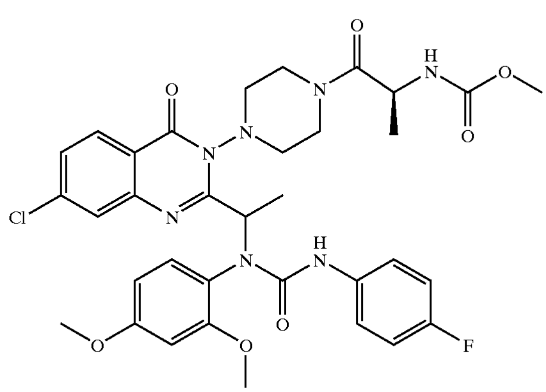 | 710/2 (M + H) | 36.0 | As compound 306, but starting from 2-amino-4-chlorobenzoic acid |

TABLE 2-continued

| Cmpd | Structure | MS | RT (min) | Reagents, starting materials |
|---|---|---|---|---|
| 310 | 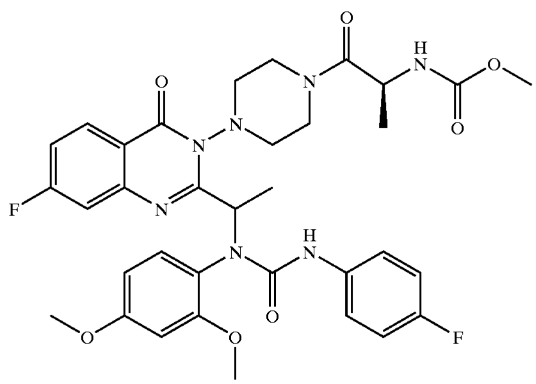 | 695 (M + H) | 33.5 | As compound 306, but starting from 2-amino-4-fluorobenzoic acid |
| 311 | 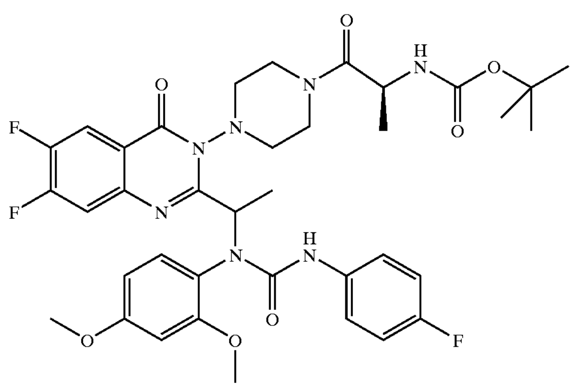 | 755 (M + H) | 40.0 | 2-amino-4,5-difluorobenzoic acid; 4-fluorophenyl isocyanate; from free piperazine: N-(t-BOC)-alanine/EDC/DMF |
| 312 | 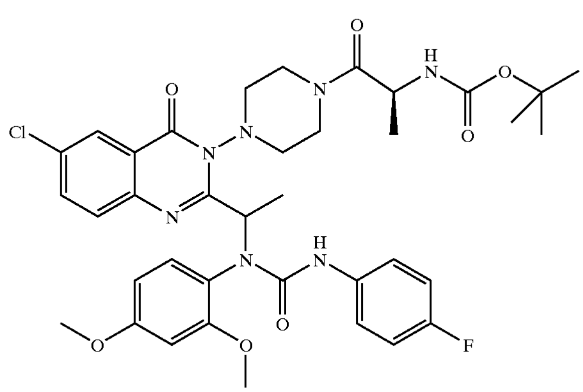 | 752/4 (M + H) | 41.0 | As compound 311, but starting from 2-amino-5-chlorobenzoic acid |
| 313 | 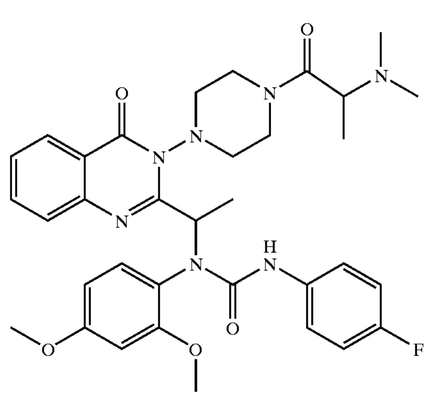 | 647 (M + H) | 26.9 | 4-fluorophenyl isocyanate; from free piperazine: 1. 2-chloropropyionyl chloride, triethylamine dichloromethane 2. dimethylamine, ethanol |

TABLE 2-continued

| Cmpd | Structure | MS | RT (min) | Reagents, starting materials |
|---|---|---|---|---|
| 314 | 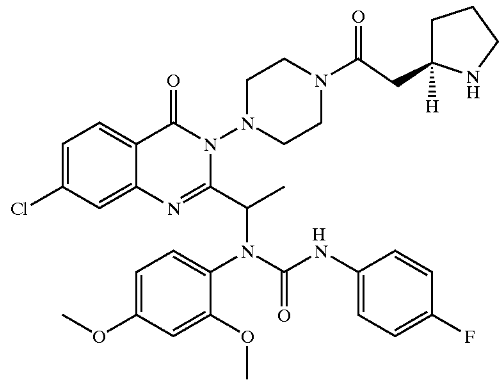 | 692/4 (M + H) | 29.6 | 2-amino-4-chlorobenzoic acid; 4-fluorophenyl isocyanate; from free piperazine: 1. (R)-2-carboxymethyl-pyrrolidine-1-carboxylic acid tert-butyl ester d/EDC/DMF 2. TFA/dichloromethane |
| 315 | 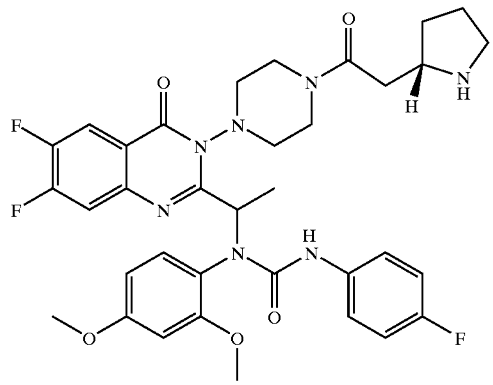 | 695 (M + H) | 28.6 | 2-amino-4,5-difluorobenzoic acid; 4-fluorophenyl isocyanate; from free piperazine: 1. (S)-2-carboxymethyl-pyrrolidine-1-carboxylic acid tert-butyl ester d/EDC/DMF 2. TFA/dichloromethane |
| 316 | 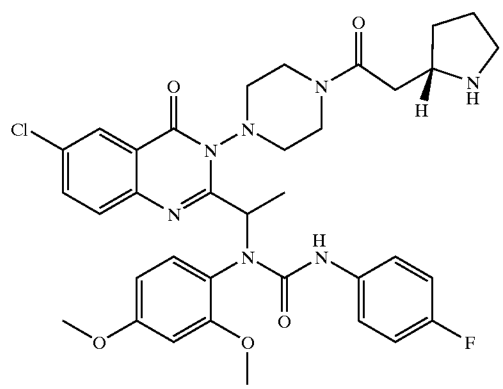 | 692/4 (M + H) | 29.0 | As compound 315, but starting from 2-amino-5-chlorobenzoic acid |
| 317 | 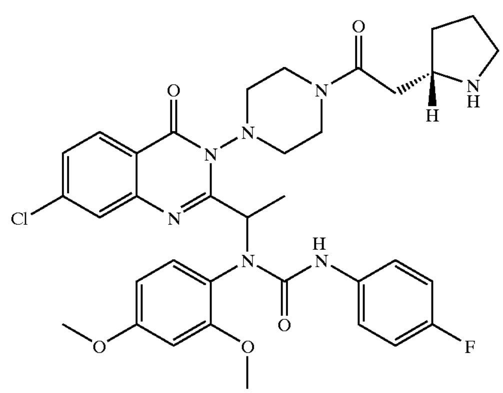 | 692/4 (M + H) | 29.6 | As compound 315, but starting from 2-amino-5-chlorobenzoic acid |

TABLE 2-continued

| Cmpd | Structure | MS | RT (min) | Reagents, starting materials |
|---|---|---|---|---|
| 318 | 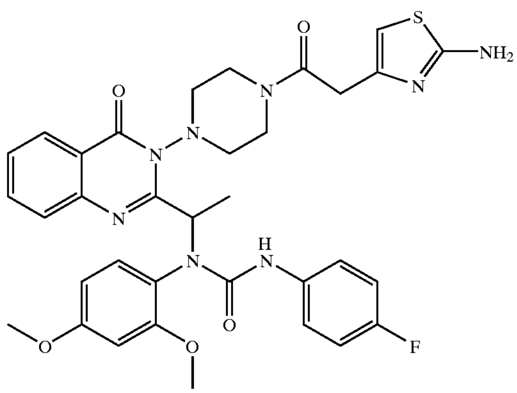 | 688 (M + H) | 30.0 | 4-fluorophenyl isocyanate; from free piperazine: (2-amino-thiazol-4-yl)-acetic acid/EDC/DMF |
| 319 | 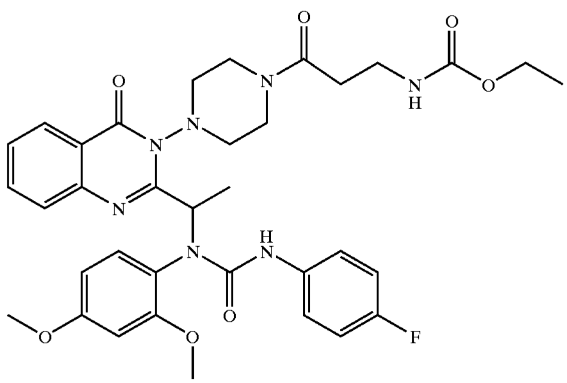 | 691 (M + H) | 32.6 | 4-fluorophenyl isocyanate; from free piperazine: 1. N-(t-BOC)-β-alanine/EDC/DMF 2. TFA/dichloromethane 3. Ethyl chloroformate |
| 320 | 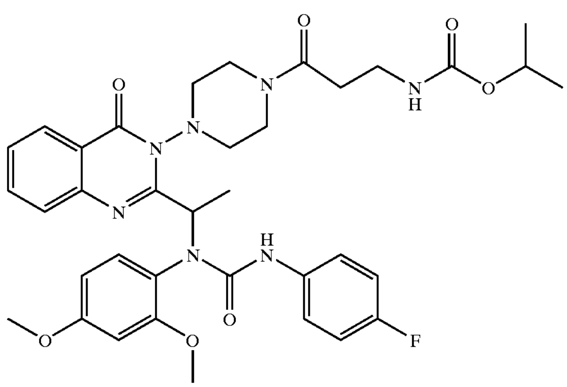 | 705 (M + H) | 34.2 | 4-fluorophenyl isocyanate; from free piperazine: 1. N-(t-BOC)-β-alanine/EDC/DMF 2. TFA/dichloromethane 3. Isopropyl chloroformate |
| 321 | 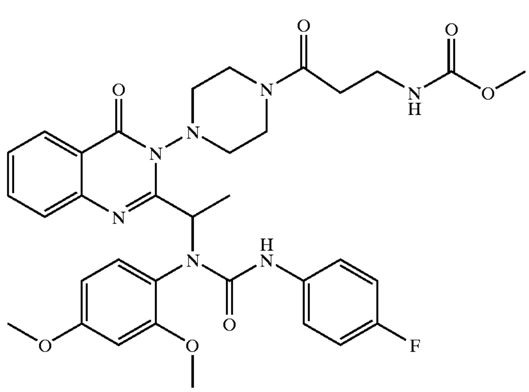 | 677 (M + H) | 31.0 | 4-fluorophenyl isocyanate; from free piperazine: 1. N-(t-BOC)-β-alanine/EDC/DMF 2. TFA/dichloromethane 3. Methyl chloroformate |

TABLE 2-continued

| Cmpd | Structure | MS | RT (min) | Reagents, starting materials |
|---|---|---|---|---|
| 322 | 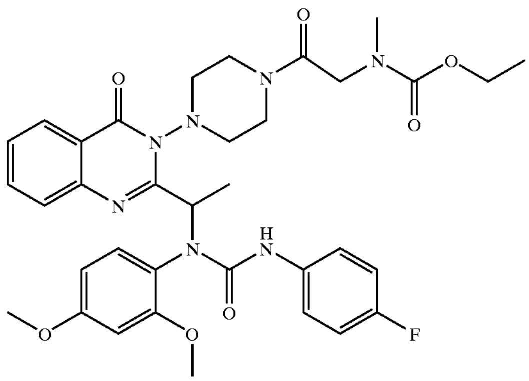 | 691 (M + H) | 33.6 | 4-fluorophenyl isocyanate; from free piperazine: 1. N-(t-BOC)-SAR-OH/EDC/DMF 2. TFA/dichloromethane 3. Ethyl chloroformate |
| 323 | 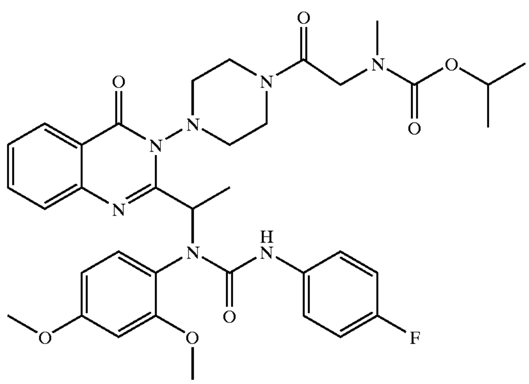 | 705 (M + H) | 35.3 | 4-fluorophenyl isocyanate; from free piperazine: 1. N-(t-BOC)-SAR-OH/EDC/DMF 2. TFA/dichloromethane 3. Isopropyl chloroformate |
| 324 | 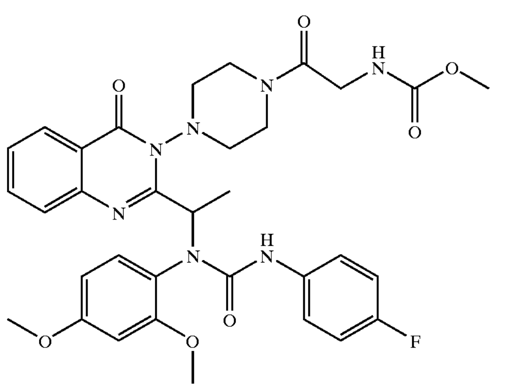 | 663 (M + H) | 31.0 | 4-fluorophenyl isocyanate; from free piperazine: 1. N-(t-BOC)-glycine/EDC/DMF 2. TFA/dichloromethane 3. Methyl chloroformate |
| 325 | 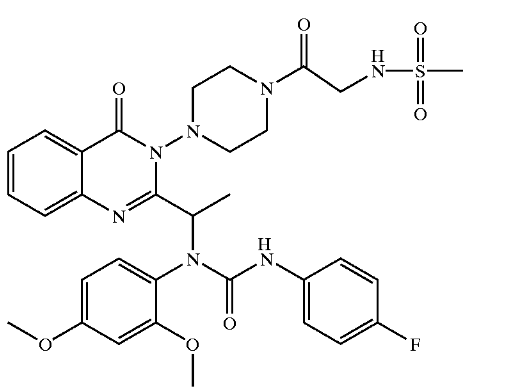 | 683 (M + H) | 31.0 | 4-fluorophenyl isocyanate; from free piperazine: 1. N-(t-BOC)-glycine/EDC/DMF 2. TFA/dichloromethane 3. Methanesulfonyl |

TABLE 2-continued

| Cmpd | Structure | MS | RT (min) | Reagents, starting materials |
|---|---|---|---|---|
| 326 | 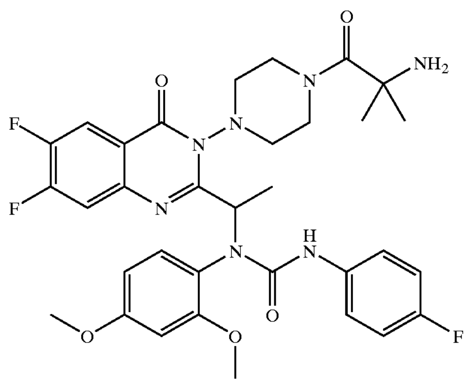 | 669 (M + H) | 28.1 | 2-amino-4,5-difluorobenzoic acid; 4-fluorophenyl isocyanate; from free piperazine: 1. 2-tert-butoxycarbonylamino-2-methyl-propionic acid/EDC/DMF 2. TFA/dichloromethane |
| 327 | 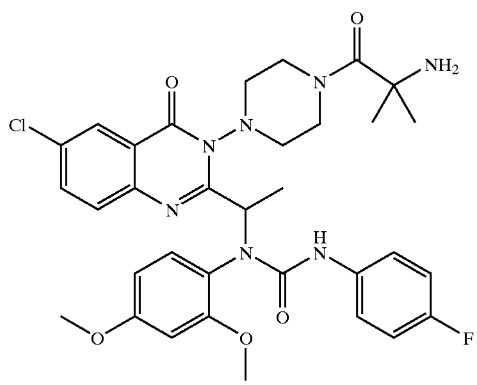 | 666/8 (M + H) | 28.4 | As compound 326, but starting from 2-amino-5-chlorobenzoic acid |
| 328 | 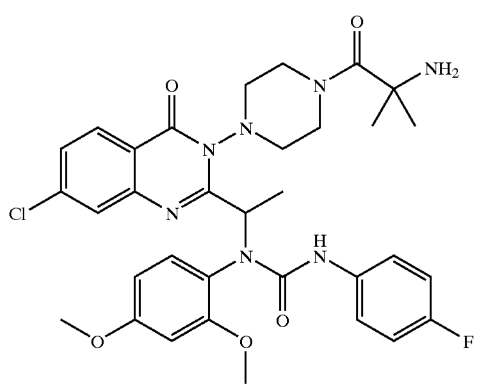 | 666/8 (M + H) | 29.0 | As compound 326, but starting from 2-amino-4-chlorobenzoic acid |
| 329 | 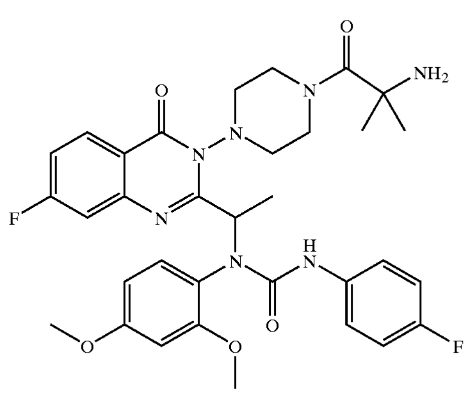 | 651 (M + H) | 26.9 | As compound 326, but starting from 2-amino-4-fluorobenzoic acid |

TABLE 2-continued

| Cmpd | Structure | MS | RT (min) | Reagents, starting materials |
|---|---|---|---|---|
| 330 | 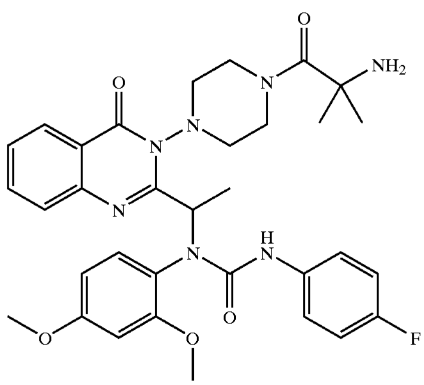 | 633 (M + H) | 25.5 | As compound 326, but starting from 2-aminobenzoic acid |
| 331 | 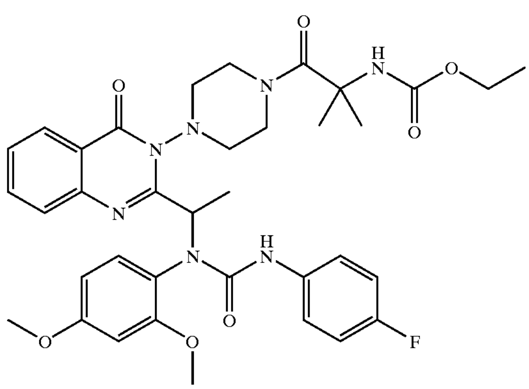 | 705 (M + H) | 32.9 | From compound 330, acylating with ethyl chloroformate |
| 332 | 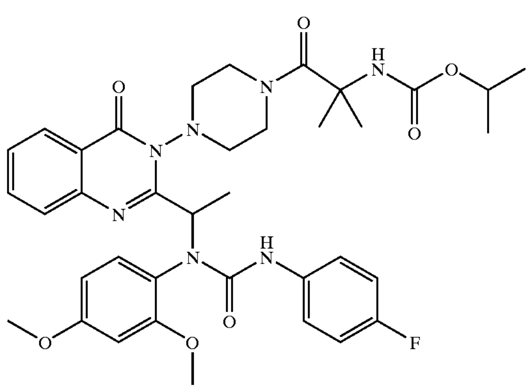 | 719 (M + H) | 34.4 | From compound 330, acylating with isopropyl chloroformate |
| 333 | 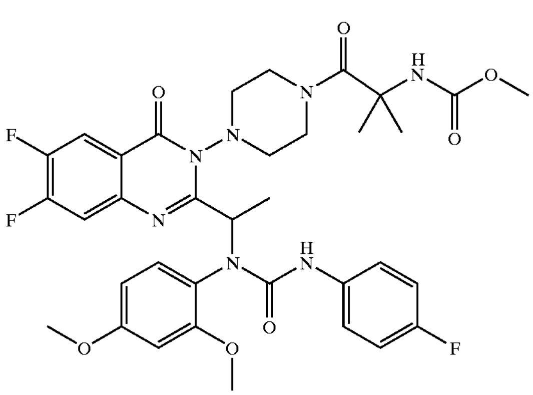 | 727 (M + H) | 34.3 | From compound 326, acylating with methyl chloroformate |

TABLE 2-continued

| Cmpd | Structure | MS | RT (min) | Reagents, starting materials |
|---|---|---|---|---|
| 334 | 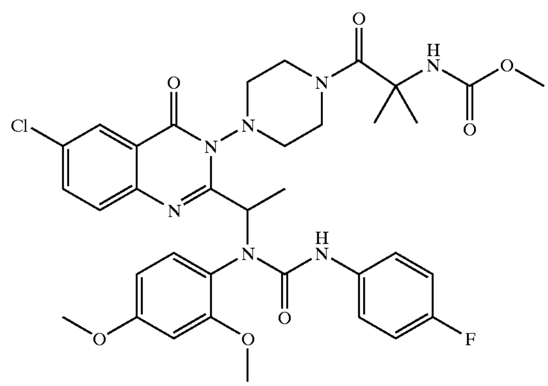 | 724/6 (M + H) | 34.9 | As for compound 333, but starting from 2-amino-5-chlorobenzoic acid |
| 335 | 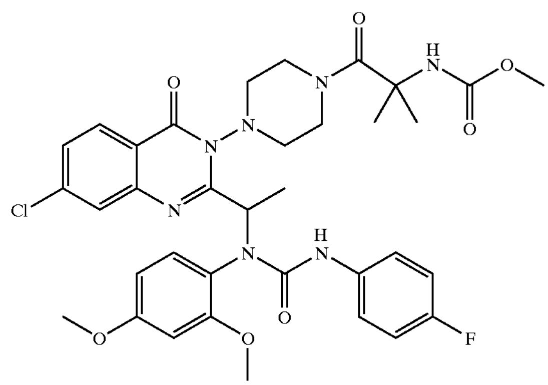 | 724/6 (M + H) | 35.3 | As for compound 333, but starting from 2-amino-4-chlorobenzoic acid |
| 336 | 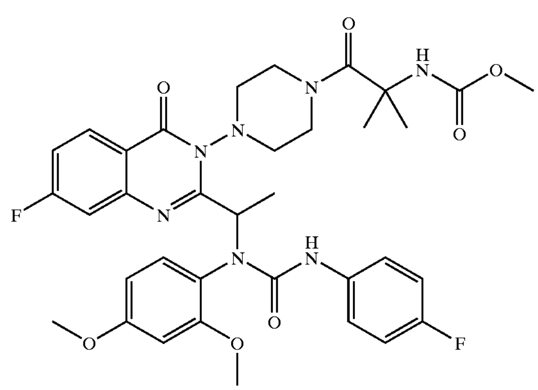 | 709 (M + H) | 33.0 | As for compound 333, but starting from 2-amino-4-fluorobenzoic acid |
| 337 | 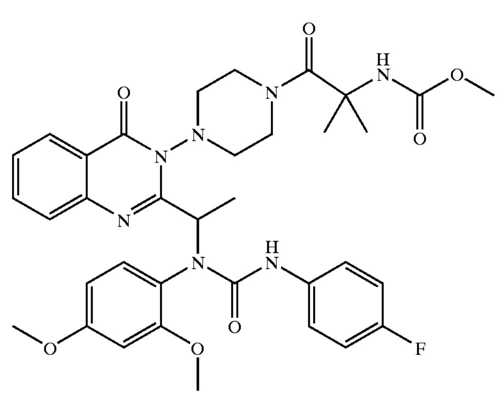 | 691 (M + H) | 31.4 | As for compound 333, but starting from 2-aminobenzoic acid |

TABLE 2-continued

| Cmpd | Structure | MS | RT (min) | Reagents, starting materials |
|---|---|---|---|---|
| 338 | 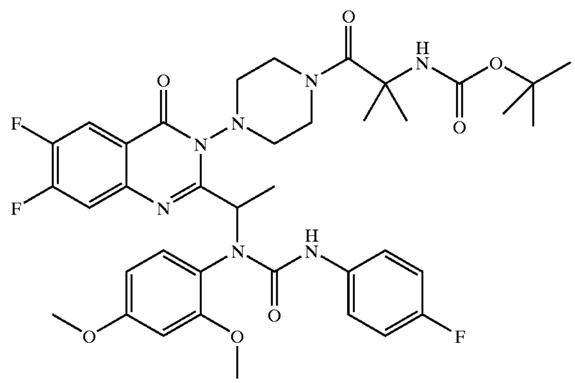 | 769 (M + H) | 38.8 | 2-amino-4,5-difluorobenzoic acid; 4-fluorophenyl isocyanate; from free piperazine: 2-tert-butoxycarbonylamino-2-methyl-propionic acid/EDC/DMF |
| 339 | 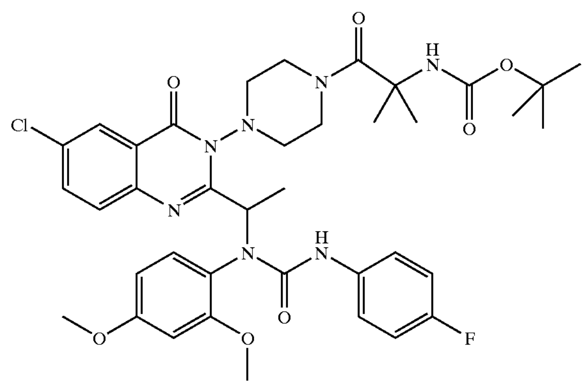 | 766/8 (M + H) | 39.7 | As for compound 338, but starting from 2-amino-5-chloro-benzoic acid |
| 340 | 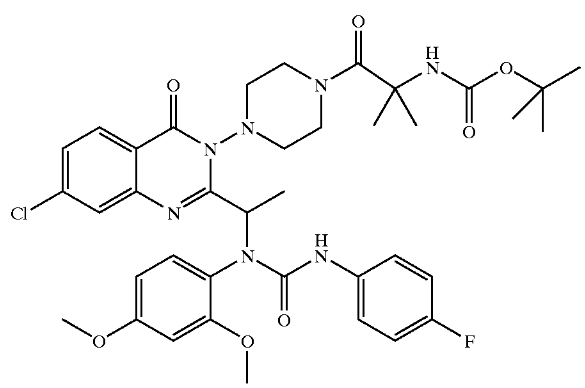 | 766/8 (M + H) | 40.2 | As for compound 338, but starting from 2-amino-4-chloro-benzoic acid |
| 341 | 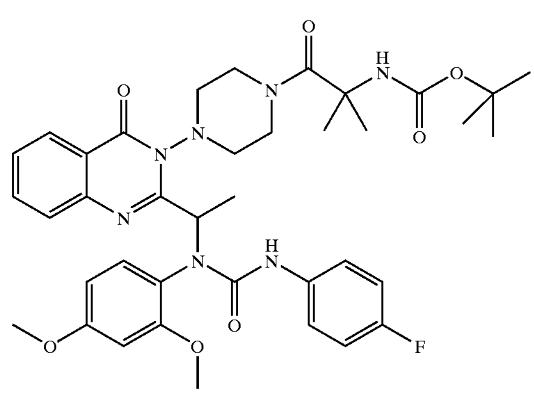 | 733 (M + H) | 36.1 | As for compound 338, but starting from 2-aminobenzoic acid |

… TABLE 2-continued

| Cmpd | Structure | MS | RT (min) | Reagents, starting materials |
|---|---|---|---|---|
| 342 | 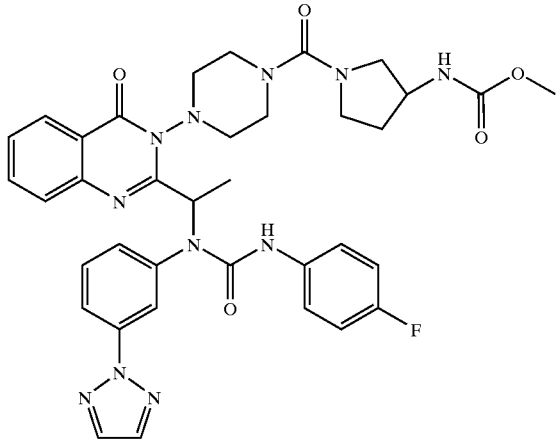 | 725 (M + H) | 31.5 | 3-[1,2,3]triazol-2-yl-phenylamine; 4-fluorophenyl isocyanate; from free piperazine: 1. triphosgene, triethylamine, 1,2-dichloroethane, RT; 2. 3-(t-butoxycarbonylamino)pyrrolidine; 3. TFA, dichloromethane 4. methyl chloroformate |
| 343 | 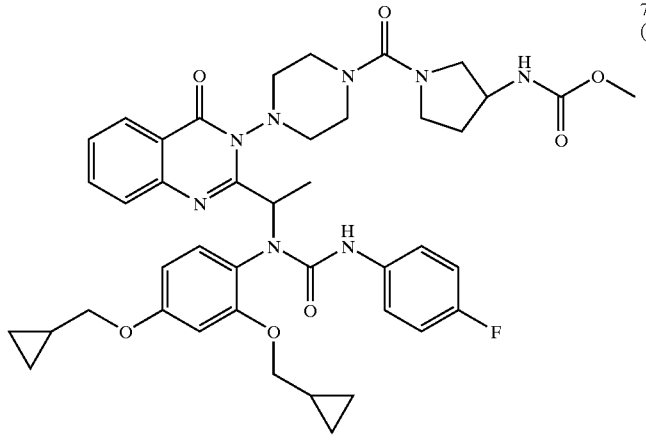 | 798 (M + H) | 38.6 | As for compound 342, but replacing 3-[1,2,3]triazol-2-yl-phenylamine with 2,4-dicyclopropoxy-phenylamine |
| 344 | 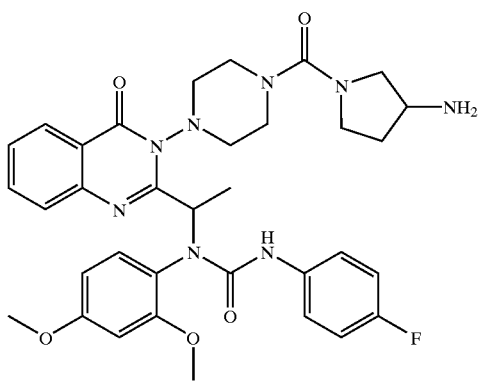 | 661 (M + H) | 25.7 | 2,6-dimethoxy-pyridin-3-ylamine; 4-fluorophenyl isocyanate; from free piperazine: 1. triphosgene, triethylamine, 1,2-dichloroethane, RT; 2. 3-(t-butoxycarbonylamino)pyrrolidine; 3. TFA, dichloromethane |

TABLE 2-continued

| Cmpd | Structure | MS | RT (min) | Reagents, starting materials |
|---|---|---|---|---|
| 345 | 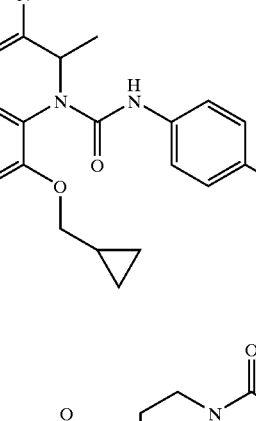 | 655 (M + H) | 29.2 | As for compound 238, starting from 2-aminobenzoic acid and replacing 2,4-dimethoxyaniline with 2-cyclopropoxyaniline |
| 346 | 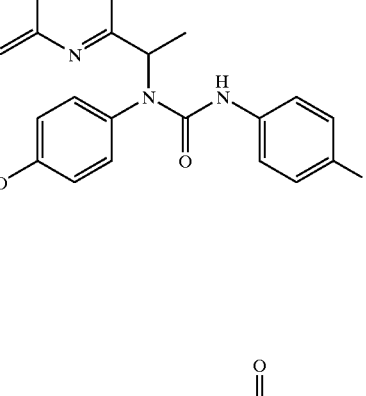 | 655 (M + H) | 30.7 | As for compound 238, starting from 2-aminobenzoic acid and replacing 2,4-dimethoxyaniline with 4-cyclopropoxyaniline |
| 347 | 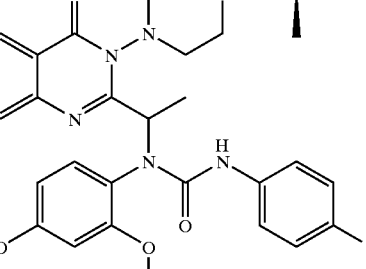 | 699 (M + H) | 32.0 | As for compound 302, starting from 2-aminobenzoic acid and replacing 2,4-dimethoxyaniline with 2,4-dicyclopropoxy-phenylamine |

TABLE 2-continued

| Cmpd | Structure | MS | RT (min) | Reagents, starting materials |
|---|---|---|---|---|
| 348 | 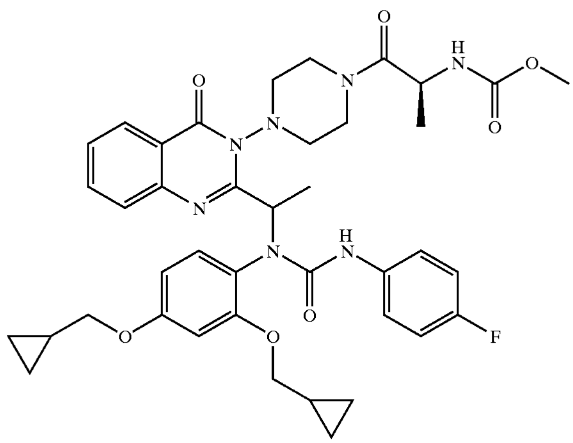 | 757 (M + H) | 39.3 | As for compound 306, starting from 2-aminobenzoic acid and replacing 2,4-dimethoxyaniline with 2,4-dicyclopropoxy-phenylamine |
| 349 | 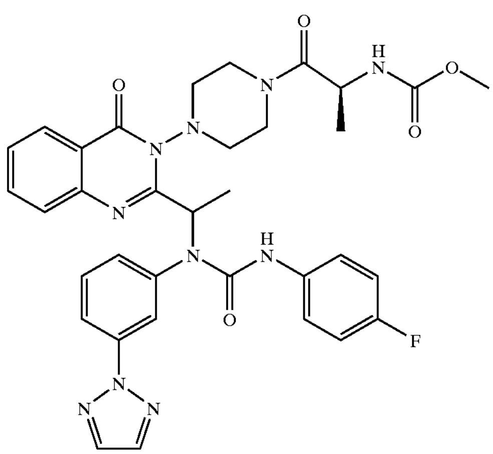 | 684 (M + H) | 33.4 | As for compound 306, starting from 2-aminobenzoic acid and replacing 2,4-dimethoxyaniline with 3-[1,2,3]triazol-2-yl-phenylamine |
| 350 | 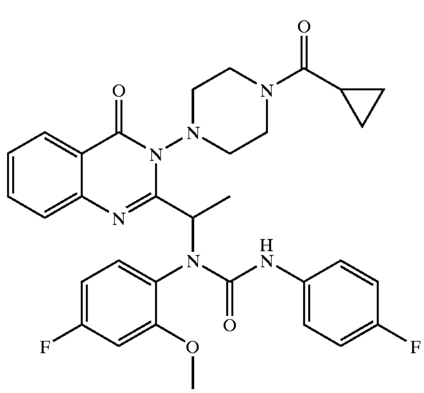 | 604 (M + H) | 34.9 | As for compound 229, replacing 2,4-dimethoxyaniline with 4-fluoro-2-methoxyaniline and acylating the free piperazine with cyclopropane carbonyl chloride |

TABLE 2-continued
| Cmpd | Structure | MS | RT (min) | Reagents, starting materials |
|---|---|---|---|---|
| 351 | 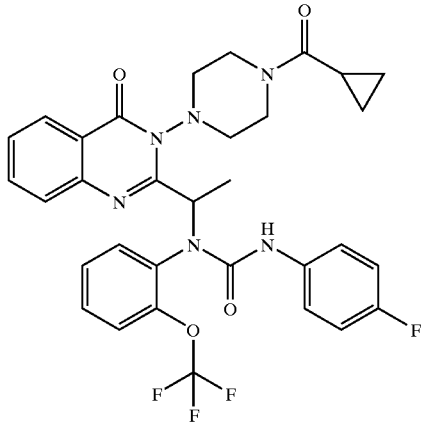 | 634 (M + H) | 37.2 | As for compound 350, replacing 2,4-dimethoxyaniline with 2-trifluoromethoxyaniline |
| 352 | 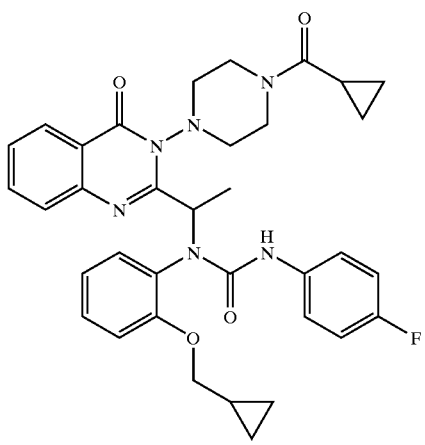 | 626 (M + H) | 37.6 | As for compound 350, replacing 2,4-dimethoxyaniline with 2-cyclopropoxyaniline |
| 353 | 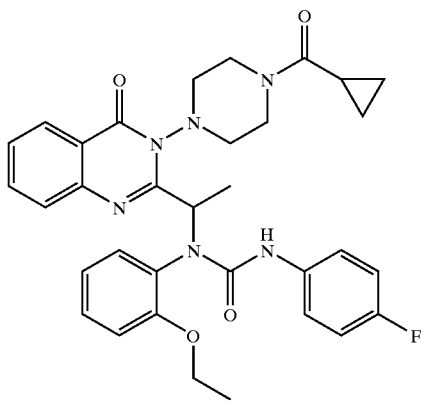 | 600 (M + H) | 35.7 | As for compound 350, replacing 2,4-dimethoxyaniline with 2-ethoxyaniline |

GM for Enantiomerically Enriched Compounds
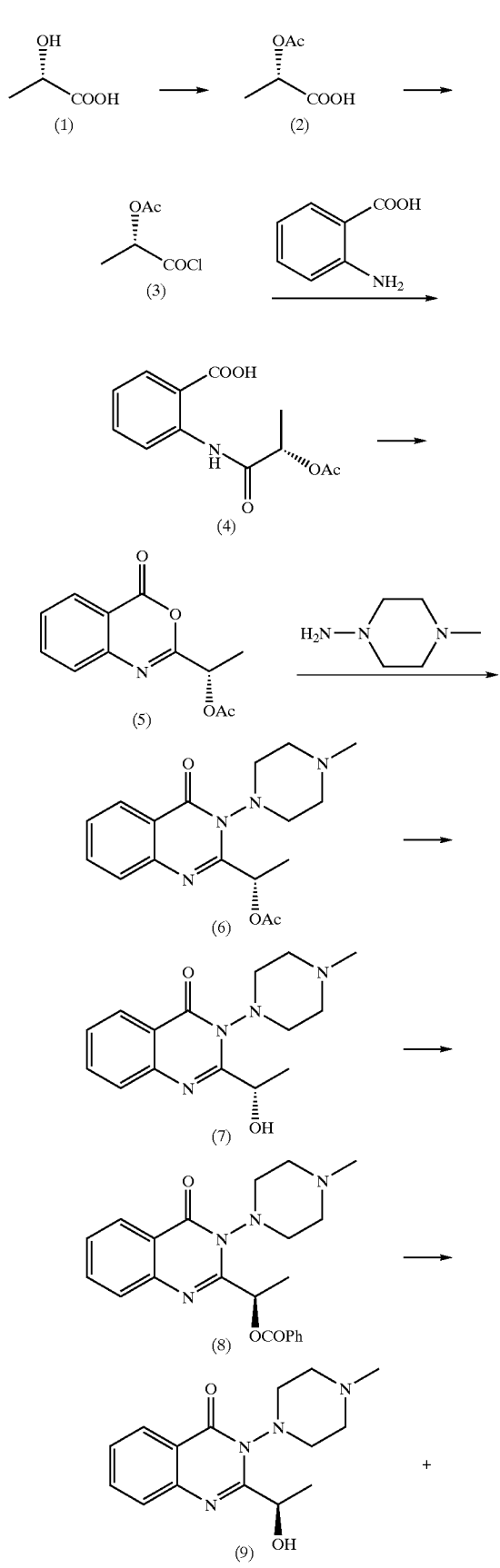
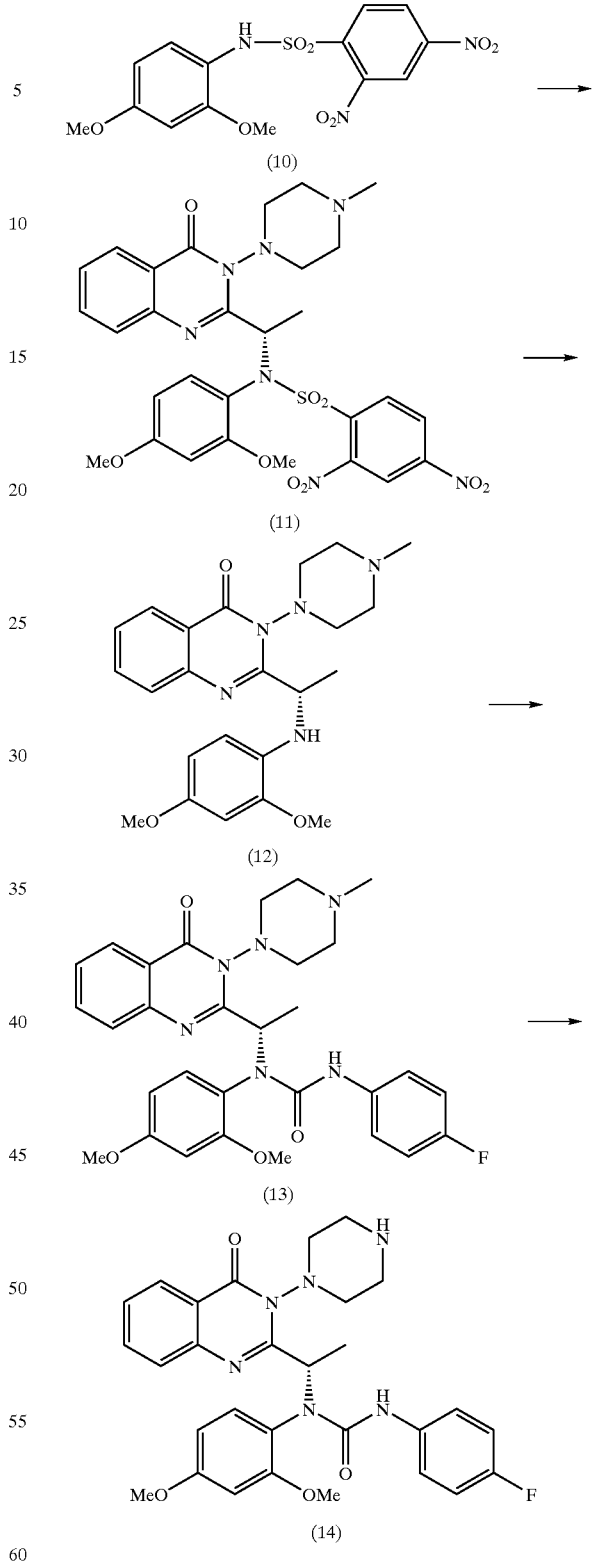
A mixture of L-Lactic acid (1, 85% solution in water; 23.5 ml), glacial acetic (89 ml), benzene (18 ml) and concentrated sulfuric acid (0.05ml) were heated at reflux with the continuous removal of water. After 24 hours the mixture was neutralized with sodium acetate (220 mg) and distilled in vacuo (100° C./1 mm Hg) to give 19.94 gm of 2.

Compound 2 (19.94 gm) was heated with thionyl chloride (12 ml) gradually for two hours to a final temperature of 95° C., followed by distillation in vacuo (50° C./5 mm Hg) to give 18.17 gm of 3.

Anthranilic acid (11.0 gm, 0.080 mol) in dry toluene (400 ml) was cooled to 0° C. Triethylamine (33.64 ml, 0.24 mol) was added. A solution of 3 (18.17 gm, 0.121 mol) in toluene (10 ml) was added slowly to the reaction mixture over 30 min. After stirring at room temperature for 1 hour, the resulting precipitate was removed by filtration and the filtrate was concentrated in vacuo. The residue was taken up in dichloromethane (300 ml), washed with water (50 ml), 1M HCl (50 ml), and brine (50 ml), dried over anhydrous magnesium sulfate, and concentrated in vacuo to give a 19.98 gm of a mixture of 4 and 5.

The mixture of 4 and 5 (19.98 gm) was heated with acetic anhydride (100 ml) at 95° C. for 2 hours. The solvent was removed in vacuo. Toluene (10 ml) was added and the mixture was again concentrated in vacuo to give 19.45 gm of product.

A solution of the above product (19.45 gm, 0.083 mol) in acetic acid (50 ml) was cooled to 0° C. 1-Amino-4-methylpiperazine (10 ml, 0.083 mol) was added over 15 minutes. The reaction mixture was heated at 90° C. for 18 hours and then cooled to room temperature. The solvent was removed in vacuo. Toluene (20 ml) was added and the mixture was again concentrated in vacuo. The residue was diluted with water (25 ml) and the pH adjusted to 3 with 1M HCl. The aqueous phase was extracted with ether (2×30 ml) and ether extract was discarded. The aqueous phase was then cooled in an ice bath and the pH was adjusted to 11 with 2M NaOH. This was then extracted with dichloromethane (2×40 ml), and the combined extracts were washed with brine (30 ml), dried over anhydrous magnesium sulfate and concentrated in vacuo to give 17.96 gm of a mixture of 6 and 7.

A solution of the above mixture of 6 and 7 (17.96 gm) in methanol (200 ml) was treated with aqueous potassium carbonate (20 gm in 100 ml of water), and the mixture was stirred at room temperature for 1 hour. The solvents were evaporated, and the residue was extracted with dichloromethane (3×30 ml). The combined extracts were washed with brine (30 ml), dried over anhydrous magnesium sulfate, and concentrated in vacua. The residue was purified by flash chromatography on silica gel, eluting with 3% MeOH/dichloromethane to give 15 gm of 7.

A solution of 7 (15 gm, 0.052 mol), triphenylphosphine (27.27 gm, 0.104 mol) and benzoic acid (12.7 gm, 0.104 mol) in dry THF (250 ml) was cooled to 0° C. Diisopropyl azodicarboxylate (21 gm, 0.104 mol) was added dropwise over 30 minutes, the mixture was allowed to warm to room temperature and the it was stirred overnight. The solvent was evaporated and the residue was dissolved in dichloromethane (300 ml), washed with 10% sodium carbonate (100 ml) and brine (100 ml), dried over anhydrous magnesium sulfate and concentrated in vacuo. The residue was purified by flash chromatography on silica gel, eluting with 4% MeOH/dichloromethane to give 15 gm of 8.

A solution of 8 (15 gm) in methanol (200 ml) was treated with aqueous potassium carbonate (17 gm in 100 ml of water), and the mixture was stirred at room temperature for 18 hours. The solvents were evaporated, and the residue was extracted with dichloromethane (3×50 ml). The combined extracts were washed with brine (50 ml), dried over anhydrous magnesium sulfate and concentrated in vacuo. The residue was purified by flash chromatography on silica gel, eluting with 5% MeOH/dichloromethane. to give 10 gm of 9.

A solution of 2,4-dimethoxyaniline (1.0 gm, 0.00653 mol) in dry dichloromethane (50 ml) was added dry pyridine (0.516 gm, 0.00653 mol, 1 eq) and 2,4-dinitrobenzenesulfonylchloride (1.74 gm, 0.00653 mol, 1 eq). The mixture was stirred at room temperature for 2 hours, washed with water (20 ml), 10% aqueous potassium carbonate (20 ml), and brine (20 ml), dried over anhydrous $MgSO_4$ and concentrated in vacua. The residue was purified by flash chromatography on silica gel, eluting with dichloromethane to give 1.7 gm of 10.

To a solution of 9 (10 gm, 0.034 mol), and triphenylphosphine (17.83 gm, 0.068 mol) and 10 (26.0 gm, 0.068 mol) in dry THF (1100 ml) was added diisopropyl azodicarboxylate (13.75 gm, 0.068 mol), dropwise over 30 minutes, at room temperature. The resulting mixture was stirred overnight, and concentrated in vacuo. The residue was dissolved in dichloromethane (1500 ml), washed with 10% sodium carbonate (400 ml) and brine (400 ml), dried over anhydrous magnesium sulfate and partially concentrated in vacuo. The precipitate that formed was isolated by filtration to give 10, which can be reused. The filtrate was concentrated and the residue purified by flash chromatography on silica gel, eluting with 6% MeOH/ethyl acetate to give 19.5 gm of 11.

To a solution of 11 (19.5 gm, 0.029 mol) in dichloromethane (500 ml) was added triethylamine (8.06 ml, 0.058 mol) and mercaptoacetic acid (6.73 ml, 0.087 mol) at room temperature. After stirring for 3 hours, the solution was diluted with dichloromethane (500 ml) and washed with 10% potassium carbonate (200 ml) and brine (200 ml), dried over anhydrous magnesium sulfate, and concentrated in vacuo. The residue was purified by flash chromatography on silica gel, eluting with 6% MeOH/ethyl acetate to give 12 gm of 12.

To a solution of 12 (12.0 gm, 0.028 mol) in dichloromethane (200 ml) was added 4-fluorophenyl isocyanate (5.82 gm, 0.042 mol), and the mixture was stirred at room temperature for 18 hours. The precipitate that formed was filtered and the filtrate was concentrated in vacuo. The residue was purified by flash chromatography on silica gel, eluting with 3% MeOH/dichloromethane to give 14.5 gm of 13.

To a solution of 13 (400 mg, 0.672 mmol) in anhydrous chloroform (20 mL) was added diisopropylethylamine (585 uL, 3.36 mmol, 5 equivalents) followed by 1-chloroethyl chloroformate (290 uL, 2.69 mmol, 4 equivalents). The mixture was refluxed for 1 hour, cooled to room temperature and concentrated in vacuo. The residue was dissolved in ethyl acetate and washed with brine. The aqueous layer was extracted with ethyl acetate and the combined organic phases were dried over sodium sulfate and concentrated to give a brown solid, which was then suspended in MeOH (20 ml) and treated with 6N HCl (20 drops). The mixture was heated at 65° C. for 10 minutes, whereupon it became homogeneous. After cooling to room temperature, the reaction was quenched by the addition of a saturated aqueous sodium bicarbonate until the solution was basic (pH=8 to 9). After extraction with ethyl acetate (3×100 mL), the combined organic layers were dried over anhydrous sodium sulfate and concentrated to dryness to give 200 mg 14 as a brown solid.

Compound 14 was then reacted with the appropriate reagents to give the compounds of this invention shown in Table 3.

Methods for the stereoselective synthesis ab initio of other compounds of this invention will become apparent to those skilled in the art based on the disclosures herein. Such enantiomerically pure compounds are within the scope of this invention.

TABLE 3

| Cmpd | Structure | MS | RT (min) | Reagents, starting materials |
|------|-----------|-----|----------|------------------------------|
| 354 | 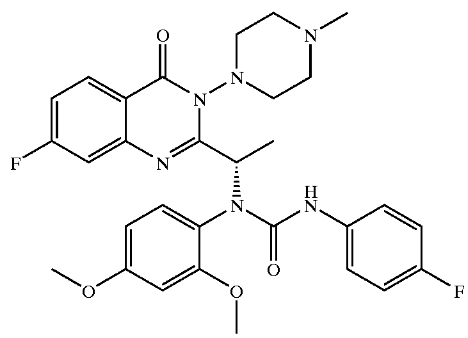 | 580 (M + H) | 29.9 | 2-amino-4-fluorobenzoic acid; 4-fluorophenyl isocyanate |
| 355 | 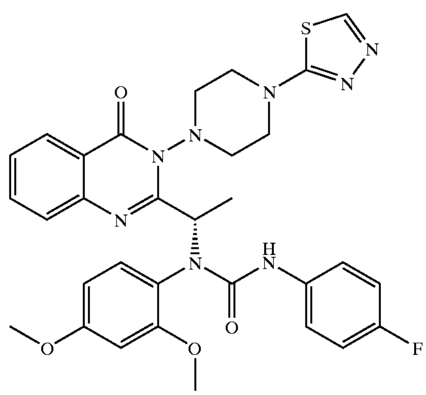 | 632 (M + H) | 32.9 | See compound 229 |
| 356 | 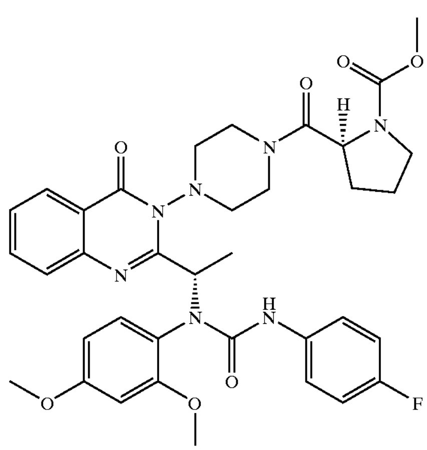 | 703 (M + H) | 32.1 | See compound 244 |

TABLE 3-continued

| Cmpd | Structure | MS | RT (min) | Reagents, starting materials |
|---|---|---|---|---|
| 357 | 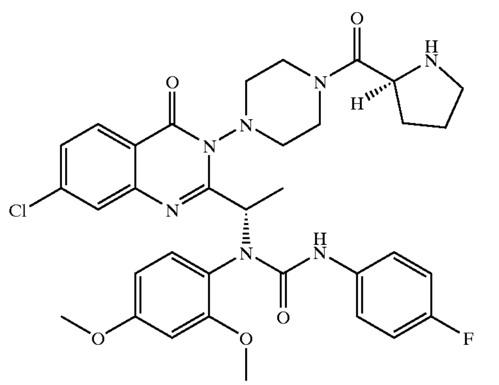 | 678/80 (M + H) | 29.6 | See compound 239 |
| 358 | 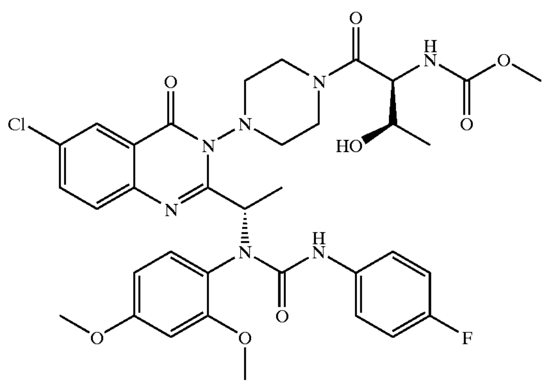 | 740/2 (M + H) | 32.9 | See compound 265 |
| 359 | 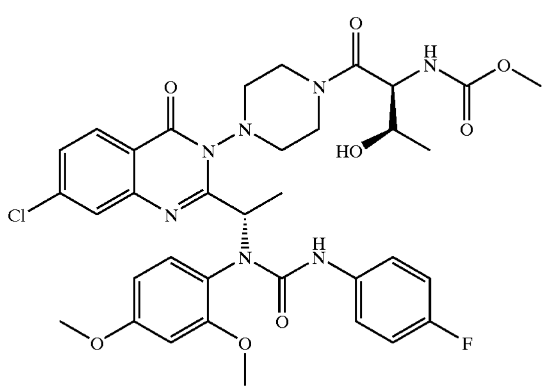 | 740/2 (M + H) | 33.2 | See compound 266 |
| 360 | 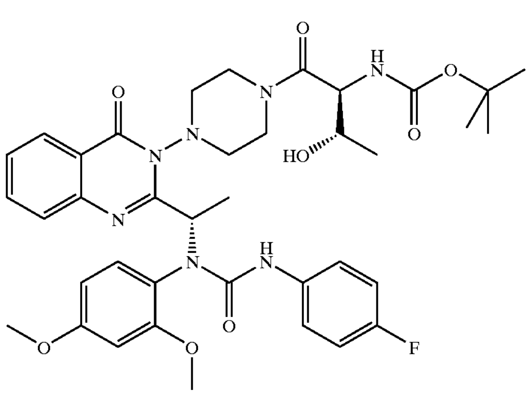 | 749 (M + H) | 35.0 | See compound 272 |

TABLE 3-continued

| Cmpd | Structure | MS | RT (min) | Reagents, starting materials |
|------|-----------|----|----|----|
| 361 | 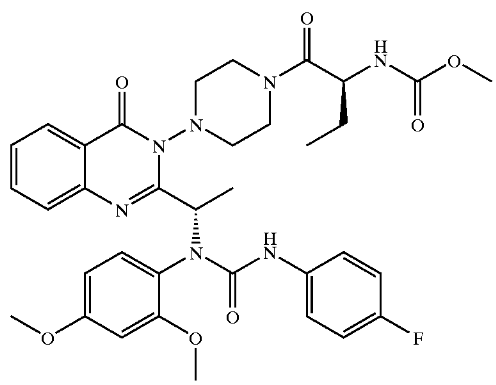 | 691 (M + H) | 33.6 | See compound 291 |
| 362 | 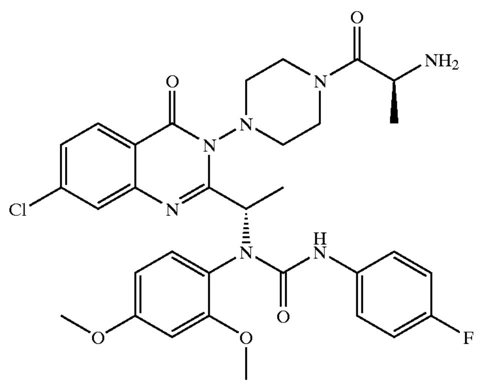 | 652/4 (M + H) | 28.5 | See compound 304 |
| 363 | 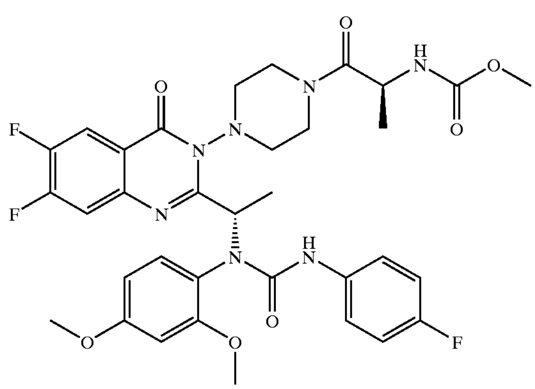 | 713 (M + H) | 34.5 | See compound 306 |
| 364 | 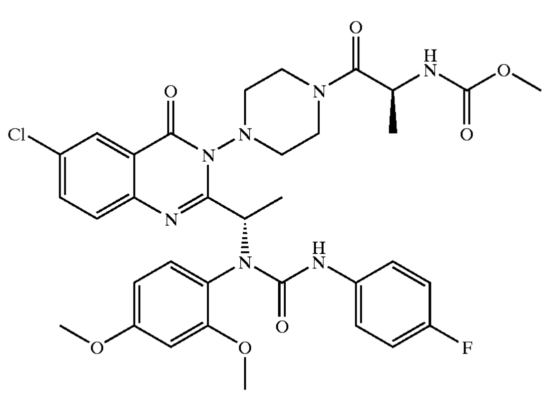 | 710/2 (M + H) | 35.6 | See compound 307 |

TABLE 3-continued

| Cmpd | Structure | MS | RT (min) | Reagents, starting materials |
|---|---|---|---|---|
| 365 | 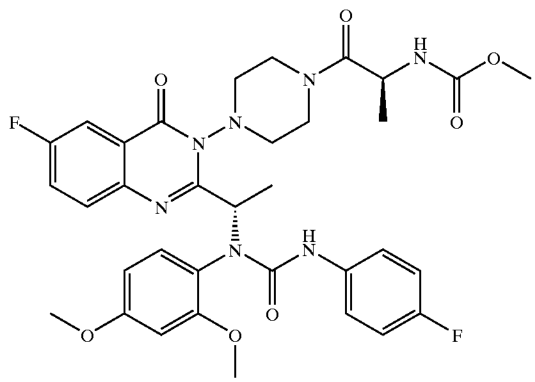 | 695 (M + H) | 32.9 | As compound 364, but starting from 2-amino-5-fluorobenzoic acid |
| 366 | 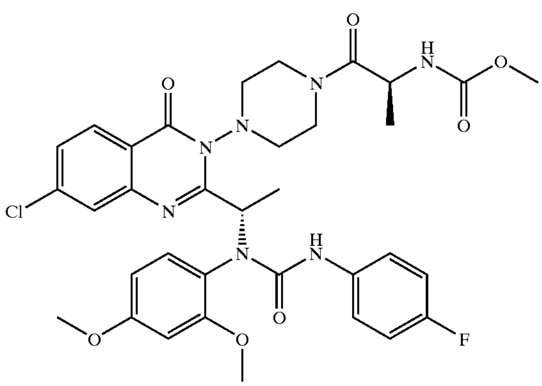 | 710/2 (M + H) | 36.0 | See compound 309 |
| 367 | 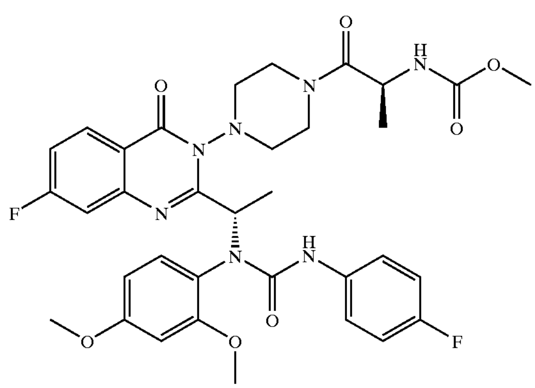 | 695 (M + H) | 33.0 | See compound 310 |
| 368 | 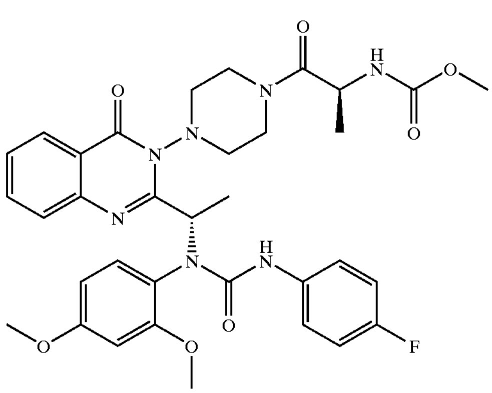 | 677 (M + H) | 32.0 | As compound 364, but starting from 2-aminobenzoic acid |

TABLE 3-continued

| Cmpd | Structure | MS | RT (min) | Reagents, starting materials |
|---|---|---|---|---|
| 369 | 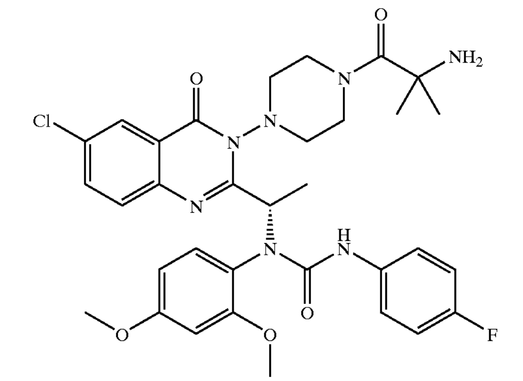 | 666/8 (M + H) | 28.0 | See compound 327 |
| 370 | 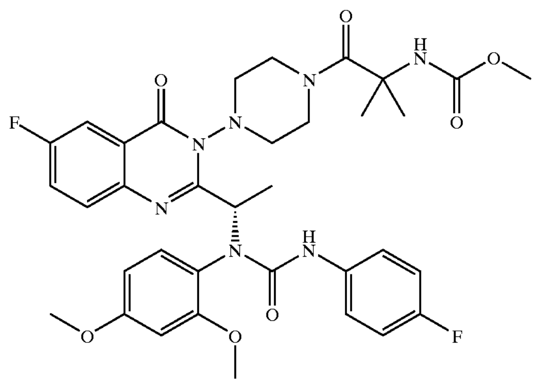 | 709 (M + H) | 32.3 | As compound 337, but starting from 2-amino-5-fluorobenzoic acid |
| 371 | 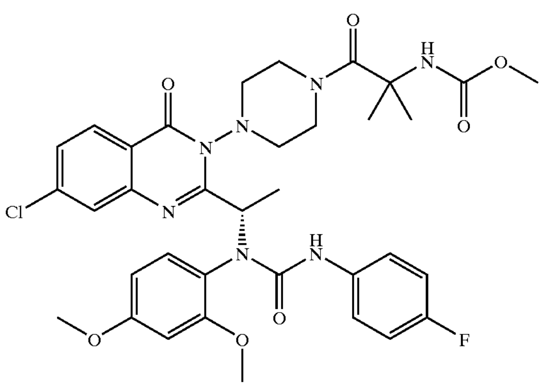 | 724/6 (M + H) | 35.0 | See compound 335 |
| 372 | 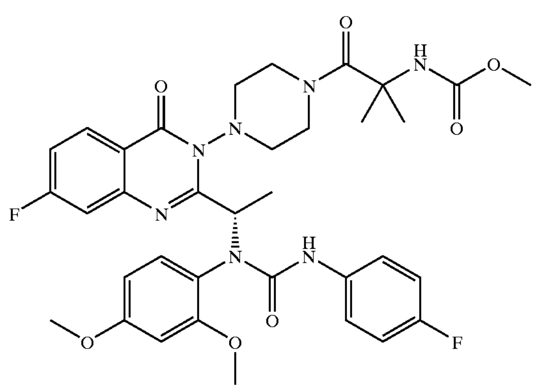 | 709 (M + H) | 33.7 | See compound 336 |

TABLE 3-continued

| Cmpd | Structure | MS | RT (min) | Reagents, starting materials |
|---|---|---|---|---|
| 373 | 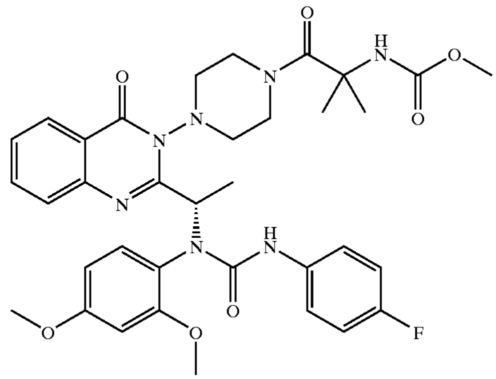 | 691 (M + H) | 31.5 | See compound 337 |

Pharmaceutical Compositions and Modes of Administration

An efflux pump inhibitory compound, or salt of prodrug thereof, and an anti-fungal agent may be administered to a patient serially or simultaneously. If serial administration is contemplated, the presently preferred approach is to administer the compound of this invention first. This permits the compound to inhibit the efflux pump(s) of the target fungal cells before the anti-fungal agent is administered, which should result in a substantially lower dosage of the anti-fungal agent being required since the fungal cells will not be able to excrete the agent. By "simultaneous" administration is meant that a compound of this invention and an anti-fungal agent are administered to a patient at essentially the same time. This can be accomplished by administering the compound herein and the anti-fungal agent separately, as in the case of two separate tablets or capsules, separate I.V. drips, or separate injections administered one immediately after the other, which, as used herein, constitutes "simultaneously." In a presently preferred embodiment, "simultaneously" means that the compound of this invention is prepared as a homogeneous composition with an anti-fungal agent and that composition is administered to the patient. In the alternative, a compound of this invention may be administered to a patient first and then, after it has had the opportunity to inhibit the efflux pump of the fungicidal cells, the anti-fungal agent is administered. Since the fungal cells will no longer be able to excrete the anti-fungal agent via the effluix pump, the agent will accumulate in the cells in sufficient concentration to inhibit the cells and treat the infection.

A compound of the present invention, a prodrug thereof or a physiologically acceptable salt of either the compound or its prodrug, can be administered as such to a patient or as a pharmaceutical compositions in which the compounds are mixed with suitable carriers or excipient(s). Techniques for formulation and administration of drugs may be found in *Remington's Pharmacological Sciences,* Mack Publishing Co., Easton, Pa., latest edition.

Suitable routes of administration include, without limitation, oral, rectal, vaginal, transmucosal, intramuscular, subcutaneous, intramedullary, intrathecal, direct intraventricular, intravenous, intravitreal, intraperitoneal, intranasal, or intraocular. The presently preferred routes of administration are oral and parenteral.

Alternatively, one may administer the compound in a localized topical rather than systemic manner. That is, the homogeneous composition of a compound herein and an anti-fungal agent can be applied directly to the surface of an infected area or injected directly into the infection.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Such pharmaceutical compositions are formulated in conventional manner and may include one or more pharmaceutically acceptable carriers, excipients and/or auxiliaries which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hanks' solution, Ringer's solution, or physiological saline buffer.

For transmucosal administration, penetrants appropriate to the barrier to be permeated are used in the formulation. Such penetrants are generally known in the art.

For oral administration, the compounds can be formulated by combining the active ingredients with pharmaceutically acceptable carriers well known in the art. Such carriers enable the compounds of the invention to be formulated as tablets, pills, lozenges, dragees, capsules, liquids, gels, syrups, slurries, suspensions and the like, suitable for oral ingestion. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethylcellulose, sodium carboxymethylcellulose, and/or polyvinylpyrrolidone (PVP). Disintegrating agents may also be added, such as cross-linked polyvinyl pyrrolidone, agar, or alginic acid. A salt such as sodium alginate may also be used.

Dragee cores are often provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings to identify the particular compounds in that composition and/or their dosages.

Pharmaceutical formulations which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage may be controlled by providing a valve that delivers a metered amount. Capsules and cartridges of, for example, gelatin for use in an inhaler or insufflator may be formulated containing a powder mix of the compound and a suitable powder base such as lactose or starch.

The compounds may also be formulated for parenteral administration. Formulations for parenteral injection may be in unit dosage form, e.g., in single-dose ampoules, or in multi-dose containers. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Or, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water.

The compounds may also be formulated in rectal compositions such as suppositories or retention enemas, using, e.g., conventional suppository bases such as cocoa butter or other glycerides.

The compounds may also be formulated as depot preparations. Such long acting formulations may be administered by implantation (for example, subcutaneously or intramuscularly) or by intramuscular injection. A compound of this invention may be formulated for this route of administration with suitable hydrophobic materials (for instance, in an emulsion with a pharmacologically acceptable oil), with ion exchange resins, or as a sparingly soluble derivative such as, without limitation, a sparingly soluble salt.

Delivery systems for hydrophobic pharmaceutical compounds include, without limitation, liposomes and emulsions. These are well known examples of delivery vehicles or carriers for hydrophobic drugs. In addition, certain organic solvents such as dimethylsulfoxide may be employed, although often at the cost of greater toxicity.

The compounds may be delivered using a sustained-release system, such as semipermeable matrices of solid hydrophobic polymers. Sustained-release materials and methods are well known to those skilled in the art. Sustained-release capsules may, depending on their chemical nature, release the compounds for a relatively short period of time, a few days perhaps even a few hours, or over very long periods of time such as 100 days or more.

The pharmaceutical compositions herein may comprise suitable solid or gel phase carriers or excipients. Examples of such carriers or excipients include,. but are not limited to, calcium carbonate, calcium phosphate, various sugars, starches, cellulose derivatives, gelatin, and polymers such as polyethylene glycols.

Dosage

Determination of a dosage that will result in a therapeutically effective amount of a fungal agent and compound of this invention being delivered to a patient will require assessment of such parameters as, without limitation, the age, gender, weight and physical condition of the patient as well as the severity of the infection, route of administration and response to previous treatments, if any. All of these are well within the knowledge and expertise of the treating physician.

In addition to the above considerations, it will be understood that the maximum permissible dose of known anti-fungal agents can be readily found in the pharmacological literature. The effect of various quantities of a compound of this invention on the amount of two conventional anti-fungal agents required to treat a fungal infection are disclosed herein. If other anti-fungal agents and/or other compounds are selected for use, the effect of various quantities of the compound on the efficacy of the anti-fungal agent can be determined without undue experimentation using the methods described herein.

While it may on occasion be desirable, even necessary, to treat a patient with massive doses of an anti-fungal agent and a compound of this invention, generally, it is preferred to use the least amount of the anti-fungal compound and of the compound herein that achieves the desired therapeutic or prophylactic effect. This determination is likewise well within the capability of the treating physician.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a fungal infections caused by particular species of fungus and the like.

Biological Activity

It is well-known that compounds having at least one asymmetric carbon, and therefore being either R or S at each such carbon as determined by the C-I-P rules, may display different biological activities depending on the absolute stereochemistry at one or more of the asymmetric carbons. In fact, in some instances, only one particular stereochemical configuration may have any biological activity at all. In the compounds of this invention, the carbon to which $R^2$ is bonded (the starred (*) carbon) is asymmetric. The presently preferred absolute stereochemistry at this carbon is S insofar as fungal efflux pump inhibition is concerned. In fact, without being bound to the theory, it is presently believed that only the S configuration has fungal efflux pump inhibitory activity and that activity shown below by racemic mixtures may actually reflect the activity of the S component. No preference is made or suggested regarding the relative or absolute stereochemistry of a compound of this invention when it is used to affect a biological function other than fungal efflux pump inhibition.

In addition to absolute stereochemistry, due to the size of the quinazolinone, piperazine and two benzene rings, the compounds of this invention also exhibit atropisomerism in relation to the single bond between the quinazolinone ring and the carbon to which $R^2$ is bonded, to the single bond between the carbon to which $R^2$ is bonded and the nitrogen of the urea group and to the single bond between the benzene ring to which $R^4$ and $R^6$ are bonded and the urea nitrogen. Again, without being bound to any particular theory, it is believed, similarly to the case of biological preference for a particular absolute and sometimes relative stereochemistry, that one of more of the possible atropisomers of the compounds of this invention may be more active as an efflux pump inhibitor than the others. Thus, the scope of this invention extends to each atropisomer individually as well as to any mixtures thereof.

The activity of test compounds of this invention in combination with an anti-fungal were assessed using a checkerboard assay and the broth microdilution protocol recommended by NCCLS Documents M27-A, Vol.17, No. 9, June 1997, entitled, "Reference Method for Broth Dilution Anti-fungal Susceptibility Testing of Yeasts, Approved Standard," and NCCLS Document M38-P, Vol. 18, No. 13, November 1998, entitled, "Reference Method for Broth Dilution Anti-fungal Susceptibility Testing of Conidiun—Forming Filamentous Fungi; Proposed Standard." The test organisms used are *Candida albicans* YEM15 (over-expressing the CDR1 and CDR2 pumps) and *C. glabrata* YEM19 (over-expressing the CgCDR1 and CgCDR2 pumps).

Multiple dilutions of a known antifungal and a compound of this invention, are tested alone and in combination at concentrations equal to, above and below the MIC, minimum inhibitory concentration, of the anti-fungal. Unless specifically stated to be otherwise, MIC's are usually reported as the amount of a compound necessary to achieve 80% of the maximum effect possible with that compound. Thus, for example, for an antifungal agent it would be the concentration of the agent that inhibits 80% of the fungal cells contacted. For instance, the MICs of fluconazole against YEM15 and YEM19 are 64 and 128 ug/ml respectively. The compounds of this invention, most of which are shown to have little or no intrinsic anti-fungal activity, are tested at concentration of from about 4 to about 32 µg/ml.

Stock solutions of the test compounds are prepared at a concentration of 64–128 µg/ml. Stock solutions are then diluted, according to the needs of a particular assay, in RPMI-1640 with MOPS buffer at 165 mM L-glutamine (Angus Buffers & Biochemicals, catalog no. R63165). Stock solutions can be stored at 4° C. Fluconazole is solubilized according to the instructions of the manufacturers, at a concentration of 10 mg/ml in 100% DMSO. It is then further diluted in RPMI.

The checkerboard assay is normally performed on microtiter plates. Serial dilutions of the anti-fungal are placed in wells horizontally across the plate resulting in each well in any column of wells having the same concentration of the anti-fungal. The test compound is serially diluted in each column of wells resulting in the rows of wells each containing the same concentration of the test compound. Thus, each well in the array contains a unique combination of anti-fungal and test compound concentrations. Test compounds are examined one per plate.

The assay is performed in RPMI using a final fungal inoculum of 1 to $5\times10^3$ CFU/ml (from an early-log phase culture). Microtiter plates are incubated for 48 h at 35° C. and are read using a microtiter plate reader (Molecular Devices) at 650 nm.

Tables 4 and 5 show potentiation of an anti-fungal agent, as manifested by a reduction in the MIC of the anti-fungal, in the presence, as contrasted to the absence, of an efflux pump inhibitor of this invention.

TABLE 4

Potentiation of fluconazole vs. *C. albicans*\*

| Example Number | MIC (µg/ml) | $MPC_8$ (µg/ml)\*\* |
|---|---|---|
| 215 | >32 | 1 |
| 216 | >32 | 0.5 |
| 217 | >32 | 4 |
| 218 | >32 | 4 |
| 219 | >32 | 8 |
| 220 | >32 | 0.25 |
| 221 | >32 | 0.125 |
| 222 | 16 | 0.5 |
| 223 | 16 | 1 |
| 224 | >32 | 1 |
| 225 | 32 | 1 |
| 226 | >32 | 1 |
| 227 | >32 | 1 |
| 228 | >32 | 4 |
| 229 | >32 | 0.125 |
| 230 | >32 | 2 |
| 232 | >32 | 0.5 |
| 234 | >32 | 2 |
| 235 | >32 | 0.25 |
| 236 | >32 | 0.5 |
| 237 | >32 | 4 |
| 239 | >32 | 8 |
| 241 | >32 | 0.5 |
| 242 | >32 | 16 |
| 243 | >32 | 16 |
| 244 | >32 | 4 |
| 245 | >32 | 1 |
| 247 | >32 | 0.5 |
| 249 | >32 | 2 |
| 250 | >32 | 8 |
| 251 | >32 | 8 |

TABLE 4-continued

Potentiation of fluconazole vs. *C. albicans**

| Example Number | MIC (μg/ml) | MPC$_8$ (μg/ml)** |
|---|---|---|
| 252 | >32 | 0.25 |
| 253 | >32 | 16 |
| 255 | >32 | 4 |
| 256 | >32 | 4 |
| 257 | >32 | 0.5 |
| 258 | >32 | 8 |
| 259 | >32 | 16 |
| 261 | >32 | 2 |
| 262 | >32 | 2 |
| 263 | >32 | 1 |
| 264 | >32 | 2 |
| 265 | >32 | 2 |
| 266 | >32 | 2 |
| 267 | >32 | 16 |
| 269 | >32 | 0.5 |
| 270 | >32 | 1 |
| 271 | >32 | 1 |
| 272 | >32 | 2 |
| 279 | >32 | 1 |
| 280 | >32 | 8 |
| 281 | >32 | 8 |
| 282 | >32 | 8 |
| 285 | >32 | 2 |
| 286 | >32 | 2 |
| 287 | >32 | 0.5 |
| 288 | >32 | 0.5 |
| 289 | >32 | 1 |
| 290 | >32 | 1 |
| 291 | >32 | 2 |
| 292 | >32 | 2 |
| 293 | >32 | 1 |
| 294 | >32 | 2 |
| 295 | >32 | 1 |
| 296 | >32 | 0.25 |
| 297 | >32 | 4 |
| 298 | >32 | 0.5 |
| 299 | >32 | 2 |
| 300 | >32 | 0.5 |
| 301 | >32 | 2 |
| 302 | >32 | 8 |
| 303 | >32 | 1 |
| 304 | >32 | 2 |
| 305 | >32 | 16 |
| 306 | >32 | 0.25 |
| 307 | >32 | 0.125 |
| 308 | >32 | 2 |
| 309 | >32 | 0.5 |
| 310 | >32 | 2 |
| 311 | >32 | 0.5 |
| 312 | >32 | 0.5 |
| 313 | >32 | 4 |
| 315 | >32 | 16 |
| 316 | >32 | 16 |
| 317 | >32 | 16 |
| 318 | >32 | 0.5 |
| 319 | >32 | 1 |
| 320 | >32 | 1 |
| 321 | >32 | 1 |
| 322 | >32 | 1 |
| 323 | >32 | 4 |
| 327 | >32 | 2 |
| 328 | >32 | 16 |
| 329 | >32 | 16 |
| 331 | >32 | 0.5 |
| 332 | >32 | 1 |
| 333 | >32 | 2 |
| 334 | >32 | 0.25 |
| 335 | >32 | 1 |
| 336 | >32 | 4 |
| 337 | >32 | 1 |
| 338 | >32 | 0.5 |
| 339 | >32 | 0.5 |
| 340 | >32 | 2 |
| 341 | >32 | 0.5 |
| 342 | >32 | 8 |
| 343 | >32 | 8 |
| 349 | >32 | 4 |
| 350 | >32 | 2 |
| 351 | >32 | 4 |
| 352 | >32 | 2 |
| 353 | >32 | 4 |
| 354 | >32 | 0.25 |
| 355 | >32 | 0.25 |
| 356 | >32 | 2 |
| 357 | >32 | 8 |
| 358 | >32 | 2 |
| 359 | >32 | 2 |
| 360 | >32 | 1 |
| 361 | >32 | 0.5 |
| 362 | >32 | 4 |
| 363 | >32 | 0.25 |
| 364 | >32 | 0.125 |
| 365 | >32 | 0.25 |
| 366 | >32 | 0.25 |
| 367 | >32 | 0.5 |
| 368 | >32 | 0.5 |
| 369 | >32 | 4 |
| 370 | >32 | 0.5 |
| 371 | >32 | 0.5 |
| 372 | >32 | 2 |
| 373 | >32 | 0.5 |

*Strain YEM15, over-expressing CDR1 and CDR2 efflux pumps
**MPC$_8$ = concentration of efflux pump inhibitor necessary to reduce the fluconazole MIC 8-fold

TABLE 5

Potentiation of fluconazole vs. *C. glabrata**

| Compound Number | MIC (μg/ml) | MPC$_8$ (μg/ml) |
|---|---|---|
| 213 | >32 | 16 |
| 214 | >32 | 16 |
| 215 | >32 | 2 |
| 216 | >32 | 0.5 |
| 217 | >32 | 4 |
| 218 | >32 | 4 |
| 219 | >32 | 8 |
| 220 | >32 | 0.5 |
| 221 | >32 | 0.5 |
| 222 | 16 | 0.5 |
| 223 | 32 | 0.25 |
| 224 | >32 | 1 |
| 225 | 32 | 1 |
| 226 | >32 | 2 |
| 227 | >32 | 1 |
| 228 | >32 | 1 |
| 229 | >32 | 2 |
| 230 | >32 | 4 |
| 231 | >32 | 2 |
| 232 | >32 | 0.25 |
| 233 | >32 | 4 |
| 234 | >32 | 0.5 |
| 235 | >32 | 0.5 |
| 236 | >32 | 0.25 |
| 237 | >32 | 0.25 |
| 238 | >32 | 2 |
| 239 | >32 | 1 |
| 240 | >32 | 2 |
| 241 | >32 | 0.125 |
| 242 | >32 | 4 |
| 243 | 16 | 2 |
| 244 | >32 | 0.5 |
| 245 | >32 | 0.25 |

TABLE 5-continued

Potentiation of fluconazole vs. *C. glabrata**

| Compound Number | MIC ($\mu$g/ml) | MPC$_8$ ($\mu$g/ml) |
|---|---|---|
| 246 | >32 | 2 |
| 247 | >32 | 0.125 |
| 248 | >32 | 8 |
| 249 | >32 | 0.5 |
| 250 | >32 | 1 |
| 251 | >32 | 1 |
| 252 | >32 | 0.125 |
| 253 | >32 | 4 |
| 254 | >32 | 4 |
| 255 | >32 | 8 |
| 256 | >32 | 4 |
| 257 | >32 | 0.5 |
| 258 | >32 | 8 |
| 259 | >32 | 1 |
| 260 | >32 | 8 |
| 261 | >32 | 2 |
| 262 | >32 | 1 |
| 263 | >32 | 2 |
| 264 | >32 | 1 |
| 265 | >32 | 2 |
| 266 | >32 | 0.5 |
| 267 | >32 | 2 |
| 268 | >32 | 4 |
| 269 | >32 | 2 |
| 270 | >32 | 2 |
| 271 | >32 | 2 |
| 272 | >32 | 2 |
| 273 | >32 | 16 |
| 274 | >32 | 4 |
| 275 | >32 | 4 |
| 276 | >32 | 16 |
| 277 | >32 | 16 |
| 278 | >32 | 8 |
| 279 | >32 | 2 |
| 280 | >32 | 2 |
| 281 | >32 | 4 |
| 282 | >32 | 1 |
| 283 | >32 | 4 |
| 284 | >32 | 4 |
| 285 | >32 | 1 |
| 286 | >32 | 1 |
| 287 | >32 | 0.25 |
| 288 | >32 | 0.25 |
| 289 | >32 | 0.125 |
| 290 | >32 | 0.25 |
| 291 | >32 | 0.5 |
| 292 | >32 | 2 |
| 293 | >32 | 1 |
| 294 | >32 | 2 |
| 295 | >32 | 2 |
| 296 | >32 | 0.125 |
| 297 | >32 | 0.5 |
| 298 | >32 | 0.5 |
| 299 | >32 | 1 |
| 300 | >32 | 0.5 |
| 301 | >32 | 2 |
| 302 | >32 | 2 |
| 303 | >32 | 4 |
| 304 | >32 | 1 |
| 305 | >32 | 4 |
| 306 | >32 | 0.0625 |
| 307 | >32 | 0.125 |
| 308 | >32 | 1 |
| 309 | >32 | 0.029 |
| 310 | >32 | 0.125 |
| 311 | >32 | 1 |
| 312 | >32 | 1 |
| 313 | >32 | 1 |
| 314 | >32 | 2 |
| 315 | >32 | 4 |
| 316 | >32 | 4 |
| 317 | >32 | 0.5 |
| 318 | >32 | 1 |
| 319 | >32 | 0.5 |
| 320 | >32 | 1 |
| 321 | >32 | 0.5 |
| 322 | >32 | 1 |
| 323 | >32 | 0.5 |
| 324 | >32 | 2 |
| 325 | >32 | 4 |
| 326 | >32 | 4 |
| 327 | >32 | 2 |
| 328 | >32 | 2 |
| 329 | >32 | 1 |
| 330 | >32 | 2 |
| 331 | >32 | 2 |
| 332 | >32 | 4 |
| 333 | >32 | 0.25 |
| 334 | >32 | 0.5 |
| 335 | >32 | 0.125 |
| 336 | >32 | 0.5 |
| 337 | >32 | 2 |
| 338 | >32 | 0.5 |
| 339 | >32 | 2 |
| 340 | >32 | 1 |
| 341 | >32 | 2 |
| 342 | >32 | 4 |
| 343 | >32 | 2 |
| 344 | >32 | 8 |
| 345 | >32 | 8 |
| 346 | >32 | 16 |
| 347 | >32 | 2 |
| 348 | >32 | 1 |
| 349 | >32 | 2 |
| 350 | >32 | 1 |
| 351 | >32 | 8 |
| 352 | >32 | 1 |
| 353 | >32 | 8 |
| 354 | >32 | 0.5 |
| 355 | >32 | 2 |
| 356 | >32 | 0.25 |
| 357 | >32 | 1 |
| 358 | >32 | 0.5 |
| 359 | >32 | 0.25 |
| 360 | >32 | 1 |
| 361 | >32 | 0.125 |
| 362 | >32 | 0.5 |
| 363 | >32 | 0.029 |
| 364 | >32 | 0.0625 |
| 365 | >32 | 0.0625 |
| 366 | >32 | 0.125 |
| 367 | >32 | 0.0625 |
| 368 | >32 | 0.25 |
| 369 | >32 | 1 |
| 370 | >32 | 0.25 |
| 371 | >32 | 0.0625 |
| 372 | >32 | 0.125 |
| 373 | >32 | 0.5 |

*Strain YEM19, over-expressing CgCDR1 and CgCDR2 efflux pumps

Conclusion

The patents and publications referenced herein are indicative of the level of skill of those skilled in the art to which this invention pertains. All such patents and publications are incorporated by reference to the same extent as if each had been separately incorporated by reference.

While the above description describes particular embodiments and examples illustrating the invention, those skilled in the art will recognize that the invention may be practiced in a variety of alternative ways, for example, by potentiating a variety of other anti-fungal agents that exhibit an efflux pump resistance mechanism. All such variations are within the scope of this invention.

Other embodiments of this invention are contained in the following claims.

What is claimed:
1. A compound having the chemical formula:

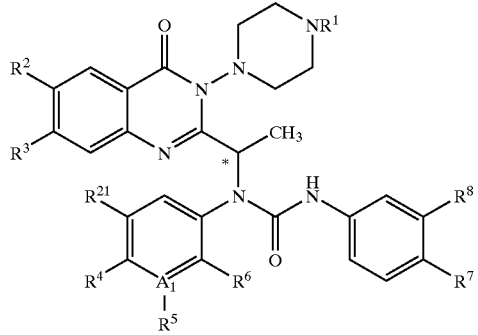

or a pharmaceutically acceptable salt thereof, wherein:

$A_1$ is carbon or nitrogen, provided that when $A_1$ is nitrogen, $R^5$ does not exist;

$R^2$ and $R^3$ are independently selected from the group consisting of hydrogen, halo and —O(1C–4C)alkyl;

$R^4$ and $R^6$ are independently selected from the group consisting of hydrogen, halo, —O(1C–4C)alkyl, —OCF$_3$, and O—CH$_2$(3C–6C)cycloalkyl;

$R^5$ is selected from the group consisting of hydrogen and

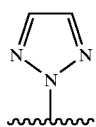

$R^7$ and $R^8$ are independently selected from the group consisting of hydrogen, halo, —C≡N, —O(1C–4C) alkyl, —OCHF$_2$, —OCF$_3$ and, taken together, —OCH$_2$O—;

$R^1$ is selected from the group consisting of -(1C–4C) alkyl, -(3C–6C)cycloalkyl, —CH$_2$(3C–6C)alkyl and

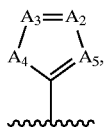

wherein:

$A_4$ is selected from the group consisting of —NH, oxygen and sulfur;

$A_2$, $A_3$ and $A_5$ are independently selected from the group consisting of carbon and nitrogen provided that no more than two of $A_2$, $A_3$ and $A_5$ are nitrogen at the same time;

or, $R_1$ is —C(O)(CH$_2$)$_n$(R$^{22}$)R$^9$, wherein, n is 0, 1, 2 or 3;

$R^9$ is selected from the group consisting of hydrogen, —OH, —(1C–4C)alkyl, -(3C–6C)cycloalkyl, —CH$_2$(3C–6C)cycloalkyl,

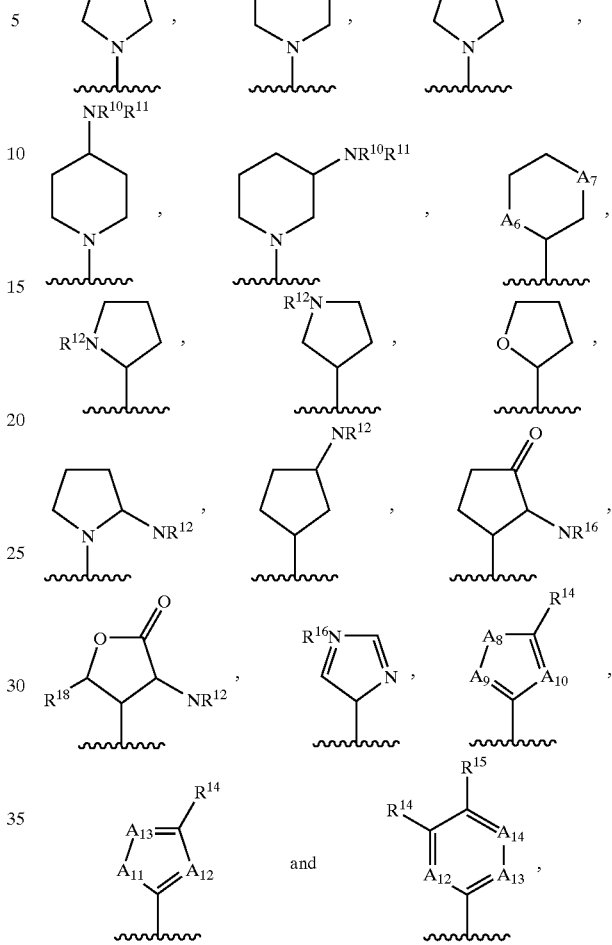

wherein:

$A_6$, $A_7$ and $A_8$ are independently selected from the group consisting of carbon, oxygen, sulfur and NR$^{15}$;

$A_9$, $A_{10}$ and $A_{11}$ are independently selected from the group consisting of carbon and nitrogen;

$R^{10}$ and $R^{11}$ are independently selected from the group consisting of hydrogen, -(1C–4C)alkyl, —SO$_2$R$^{16}$, —C(O)R$^{16}$ and —C(O)OR$^{16}$, wherein:

$R^{16}$ is selected from the group consisting of hydrogen and -(1C–4C)alkyl wherein the alkyl group may be substituted with 1, 2, 3, or 4 fluorines;

$R^{12}$ is selected from the group consisting of hydrogen, -(1C–4C)alkyl, -(3C–6C)cycloalkyl, —CH$_2$(3C–6C) cycloalkyl, —C(O)O-(1C–4C)alkyl, —SO$_2$R$^{17}$ and —SO$_2$NR$^{18}$R$^{19}$, wherein, $R^{17}$, $R^{18}$ and $R^{19}$ are independently selected from the group consisting of hydrogen and -(1C–4C)alkyl;

$R^{14}$ and $R^{15}$ are independently selected from the group consisting of hydrogen, -(1C–4C)alky and —NR$^{10}$R$^{11}$;

$R^{22}$ is selected from the group consisting of hydrogen and (1C–4C)alkyl;

or, $R^9$ is —C(R$^{16}$)(R$^{20}$)(CH$_2$)$_p$NR$^{10}$R$^{11}$, wherein:

p is 0, 1 or 2;

$R^{20}$ is selected from the group consisting of hydrogen and -(1C–4C)alkyl, the alkyl group being optionally substituted with an entity selected from the group consisting of —OH, —O(1C–4C)alkyl, —C≡N, —SO$_2$(1C–4C)alkyl and

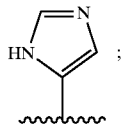

;

and, the compound comprises a racemic mixture, a pure enantiomer or a pure atropisomer of either the racemic mixture or the pure enantiomer.

2. The compound of claim 1, wherein the compound is in the S absolute configuration at the starred carbon.

3. The compound of claim 2, wherein:

A$_1$ is carbon; and,

R$^{22}$ is selected from the group consisting of hydrogen and —CH$_3$.

4. The compound or salt of claim 3, wherein R$^4$ and R$^6$ are independently selected from the group consisting of —O(1C–4C)alkyl and —OCH$_2$(3C–6C)cycloalkyl.

5. The compound or salt of claim 4, wherein R$^4$ and R$^6$ are OCH$_3$.

6. The compound or salt of claim 4, wherein R$^4$ and R$^6$ are

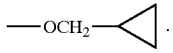

.

7. The compound of salt of claim 5, wherein:

R$^7$ is selected from the group consisting of hydrogen and halogen; and,

R$^8$ is hydrogen.

8. The compound of salt of claim 7, wherein R$^7$ is fluorine.

9. The compound or salt of claim 2, wherein A$_1$ is nitrogen.

10. The compound or salt of claim 9, wherein R$^4$ and R$^6$ are independently selected from the group consisting of -O(1C–4Calkyl) and —OCH$_2$(3C–6C)cycloalkyl.

11. The compound or salt of claim 10, wherein R$^4$ and R$^6$ are OCH$_3$.

12. The compound or salt of claim 11, wherein R$^7$ is selected from the group consisting of hydrogen and fluorine.

13. The compound or salt of claim 3, wherein:

R$^6$ is selected from the group consisting of —OCH$_3$ and

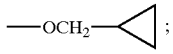

;

and, R$^7$ is F.

14. The compound or salt of claim 3, wherein:

R$^6$ is selected from the group consisting of —OCH$_3$ and

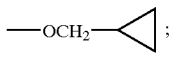

;

and, R$^5$ is —C(O)CH$_3$.

15. The compound or salt of claim 3, wherein R$^4$ and R$^6$ are

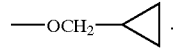

.

16. The compound or salt of claim 3, wherein R$^{21}$ is —NHSO$_2$CH$_3$.

17. The compound of salt of claim 3, wherein R$^5$ is

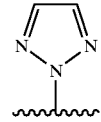

18. A pharmaceutical composition, comprising:
a pharmaceutically acceptable carrier or excipient; and,
a compound of any one of claims 1–17.

19. The pharmaceutical composition of claim 18, further comprising a therapeutically effective amount of an anti-fungal agent.

20. The pharmaceutical composition of claim 19, wherein the anti-fungal agent is an azole anti-fungal agent.

21. The pharmaceutical composition of claim 20, wherein the azole anti-fungal agent is fluconazole or posaconazole.

22. A method for inhibiting a fungal cell that employs an efflux pump resistance mechanism, comprising contacting the cell with an anti-fungal agent and a compound of any one of claims 2–17.

23. The method of claim 22, wherein the anti-fungal agent is an azole anti-fungal agent.

24. The method of claim 23, wherein the azole fungicide is selected from the group consisting of fluconazole and posaconazole.

25. The method of claim 22, wherein the fungal cell is first contacted with the compound and then with the anti-fungal agent.

26. The method of claim 22, wherein the fungal cell is contacted with the compound and the anti-fungal agent simultaneously.

27. The method of claim 22, wherein the fungal cell is a genus Candida cell.

28. The method of claim 27, wherein the genus Candida cell is selected from the group consisting of *C. albicans, C. krusei, C. tropicalis, C. parapsilosis* and *C. glabrata*.

29. The method of claim 22, wherein the fungal cell is a genus Aspergillus cell.

30. The method of claim 29, wherein the genus Aspergillus cell is an *Aspergillus fumigatus* cell.

31. A method for treating an infection caused by a fungus that employs an efflux pump resistance mechanism, comprising administering to a patient in need thereof a therapeutically effective amount of an anti-fungal agent and a compound of any one of claims 2–17.

32. The method of claim 31, wherein the infection is caused by a genus Candida fungus.

33. The method of claim 32, wherein the Candida fungus is *C albicans, C. krusei, C. tropicalis, C. parapsilosis* or *C. glabrata*.

34. The method of claim 31, wherein the infection is caused by a genus Aspergillus fungus.

35. The method of claim 31, wherein the genus Aspergillus fungus is *Aspergillus fumigatus*.

36. The method of claim 31, wherein the compound and the anti-fungal agent are administered simultaneously.

37. The method of claim 31, wherein the compound is administered first followed by administration of the anti-fungal agent.

* * * * *